US006174883B1

(12) United States Patent
Ehrgott et al.

(10) Patent No.: US 6,174,883 B1
(45) Date of Patent: Jan. 16, 2001

(54) 3-SUBSTITUTED-2-OXINDOLES DERIVATIVES

(75) Inventors: Frederick J. Ehrgott; Carl J. Goddard; Gary R. Schulte, all of Groton, CT (US)

(73) Assignee: Pfizer Inc., New York, NY (US)

( * ) Notice: Under 35 U.S.C. 154(b), the term of this patent shall be extended for 0 days.

(21) Appl. No.: 08/477,729

(22) Filed: Jun. 7, 1995

Related U.S. Application Data

(62) Division of application No. 08/148,764, filed on Nov. 4, 1993, now Pat. No. 5,919,809, which is a division of application No. 07/712,169, filed on Jun. 5, 1991, now Pat. No. 5,290,802, which is a division of application No. 07/473,266, filed on Jan. 31, 1990, now Pat. No. 5,047,554, which is a continuation-in-part of application No. 07/340,113, filed on Apr. 18, 1989, now abandoned.

(51) Int. Cl.[7] ..................... C07D 409/06; C07D 409/13; A61K 31/403; A61P 19/02

(52) U.S. Cl. ..................... 514/228.2; 514/235.2; 514/252; 514/255; 514/256; 514/323; 514/339; 514/361; 514/363; 514/365; 514/372; 514/374; 514/378; 514/381; 514/383; 514/385; 514/396; 514/403; 514/418; 544/62; 544/153; 544/238; 544/333; 544/336; 544/366; 544/367; 544/369; 544/370; 544/371; 544/373; 546/201; 546/273; 548/136; 548/143; 548/181; 548/235; 548/253; 548/266.2; 548/312.1; 548/335.1; 548/364.7; 548/374.1; 548/376.1; 548/486

(58) Field of Search ............................. 514/228.2, 235.2, 514/252, 255, 256, 323, 339, 361, 363, 365, 372, 374, 378, 381, 383, 385, 396, 403, 418; 544/62, 153, 238, 333, 336, 366, 367, 369, 370, 371, 373; 546/201, 273; 548/136, 143, 181, 235, 253, 266.2, 312.1, 335.1, 364.7, 374.1, 376.1, 486

(56) References Cited

U.S. PATENT DOCUMENTS

| | | | |
|---|---|---|---|
| 3,634,453 | 1/1972 | McManus et al. | 260/325 |
| 3,900,563 | 8/1975 | Allen, Jr. et al. | 424/250 |
| 4,556,672 | 12/1985 | Kadin | 514/414 |
| 4,569,942 | 2/1986 | Kadin | 514/414 |
| 4,690,943 | 9/1987 | Kadin | 514/418 |
| 4,695,571 | 9/1987 | Melvin | 514/275 |
| 4,721,712 | 1/1988 | Kadin | 514/253 |
| 4,752,609 | 6/1988 | Kadin | 514/339 |
| 4,808,601 | 2/1989 | Kadin | 514/374 |
| 4,861,794 | 8/1989 | Otterness | 514/414 |
| 4,962,117 | 10/1990 | Young et al. | 514/365 |
| 5,290,802 | * 3/1994 | Ehrgott et al. | 514/414 |

FOREIGN PATENT DOCUMENTS

| | | | |
|---|---|---|---|
| 0014667 | 2/1973 | (JP) | 548/486 |
| 8803658 | 5/1990 | (WO) . | |

OTHER PUBLICATIONS

Carpenter, A.J. et al., Regioselective alpha–and beta–Metallations of Thiophene Derivatives Bearing the 4,4–Dimethyloxazolin–2–yl Group. Application of the Method to Syntheses of 2,3–and 2,5–Disubstituted Thiophene Derivatives, J. Chem. Soc. Perkin Trans 1:173–181 (1985) (Carpenter I), 1985.

Carpenter, A. J. et al., The Scope and Limitations of Carboxamide–induced beta–Directed Metalation of 2–Substituted Furan, Thiophene, and 1–Methylpyrrole Derivatives. Application of the Method to Syntheses of 2,3–Disubstituted Thiophene and Furans, J. Org. Chem. 50:4362–4368 (1985) (Carpenter II), 1985.

2–Mercaptothiazol–4–ylthiophenecarboxylic acids, Chem. Abstr. 103:22580m (1985).

2–Azolyl–5–oxadiazolylthiophenes, Chem. Abstr. 63, column 4432 (1965).

(List continued on next page.)

* cited by examiner

*Primary Examiner*—John M. Ford
*Assistant Examiner*—Thomas McKenzie
(74) *Attorney, Agent, or Firm*—Peter C. Richardson; Gregg C. Benson

(57) ABSTRACT

This invention relates to novel 3-substituted-2-oxindole derivatives of the formula (I)

and the phamaceutically-accepted salts thereof which are inhibitors of prostaglandin $H_2$ synthase, 5-lipoxygenase and interleukin-1 biosynthesis. The compounds of the invention are useful as inhibitors of prostaglandin $H_2$ synthase and interleukin-1 biosynthesis, per se, and as analgesic, antiinflammatory and antiarthritic agents in the treatment of chronic inflammatory diseases. This invention also relates to pharmaceutical compositions comprising said 3-substituted-2-oxindole derivatives; to methods of inhibiting prostaglandin $H_2$ synthase and biosynthesis of interleukin-1; and to treating chronic inflammatory diseases in a mammal with said compounds. Further, this invention relates to certain novel carboxylic acids useful as intermediates in the preparation of the 3-substituted-2-oxindole derivatives of this invention and to a process for the preparation of the 3-substituted-2-oxindole derivatives.

93 Claims, No Drawings

OTHER PUBLICATIONS

Benkeser, R. A. et al. Selective Reduction of Aromatic Carboxyl Groups to Methyl in the Presence of Ester Functionality. A New Procedure for the Preparation of Ester–Containing Organosilanes, J. Org. Chem. 38:3660–3661 (1973).

Chem. Abstr. 49 columns 2233–2236 (1955).

Brooks, D. W. et al., C–Acylation under Virtually Neutral Conditions, Angew. Chem. Int. Ed. Engl. 18:72–74 (1979).

Staab, H. A.,, Aregewande Chem. 17:415 part e (1962) (Angew. Chem. Internat. Edit. 1(7):351–367 (1962)).

Baker, D. C., C–Acylation of Nitromethane, A Synthetic Route to alpha–Nitroketones. Synthesis (1978) p. 478–479.

Otterness, I. G. et al., Effects of CP–66,248 on IL–1 Synthesis by Murine Peritoneal Macrophages, Arthritis & Rheumatism 31 No. 4 (Supplement):S90 Abstract C55 (1988).

Davis, J. S. et al., Clinical Efficacy of CP–66,248 [5–Chloro–2, 3–dihydro–2–oxo–3–(2–thienylcarbonyl)–indole–1–carbox amide]in Osteoarthritis, Arthritis & Rheumatism 31 No. 4 (Supplement):S72 Abstract B78 (1988).

"Three Pfizer Drugs Promising; FDA Okay to be Sought in '89", Chemical Marketing Reporter, Sep. 14, 1987, p.7.

FDC Reports "The Pink Sheet"®, Sep. 14, 1987, p. 2.

FDC Reports "The Pink Sheet"®, Sep. 28, 1987, p. 11.

Kobayashi, Goro et al., Chem. Abst. 69 (13):4854 (No. 52001v), Sep. 23, 1968.

Oki, Sadao et al., Chem. Abst. 78 (21):363 (No. 136057s), May 28, 1973.

Chem. Abst. 98 (21):659 (No. 179366x), May 23, 1983.

3-SUBSTITUTED-2-OXINDOLES DERIVATIVES

CROSS REFERENCE TO RELATED APPLICATIONS

This is a division of application Ser. No. 08/148,764, filed Nov. 4, 1993, now U.S. Pat. No. 5,919,809 which is a division of application Ser. No. 07/712,169, filed Jun. 5, 1991, now U.S. Pat. No. 5,290,802, which is a division of Ser. No. 07/473,266, filed Jan. 31, 1990, now U.S. Pat. No. 5,047,554, which application is a continuation-in-part of application Ser. No. 07/340,113, filed Apr. 18, 1989 now abandoned.

TECHNICAL FIELD

This invention relates to novel 3-substituted-2-oxindole derivatives which are inhibitors of prostaglandin $H_2$ synthase, 5-lipoxygenase and interleukin-1 biosynthesis. The compounds of the invention are useful as inhibitors of prostaglandin $H_2$ synthase and interleukin-1 biosynthesis, per se, and as analgesic, antiinflammatory and antiarthritic agents in the treatment of chronic inflammatory diseases. This invention also relates to pharmaceutical compositions comprising said 3-substituted-2-oxindole derivatives; to methods of inhibiting prostaglandin $H_2$ synthase and biosynthesis of interleukin-1; and to treating chronic inflammatory diseases in a mammal with said compounds. Further, this invention relates to certain novel carboxylic acids useful as intermediates in the preparation of the 3-substituted-2-oxindole derivatives of this invention and to a process for the preparation of the 3-substituted-2-oxindole derivatives.

BACKGROUND ART

U.S. Pat. No. 4,569,942 discloses certain 2-oxindole-1-carboxamides of the formula

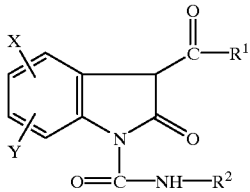

wherein, inter alia, X is H, fluoro, chloro, bromo, $(C_1-C_4)$ alkyl, $(C_3-C_7)$cycloalkyl, $(C_1-C_4)$alkoxy, $(C_1-C_4)$alkylthio, trifluoromethyl, $(C_1-C_4)$alkylsulfinyl, $(C_1-C_4)$alkylsulfonyl, nitro, phenyl, $(C_2-C_4)$-alkanoyl, benzoyl, thenoyl, $(C_1-C_4)$alkanamido, benzamido or N,N-dialkylsulfamoyl having 1 to 3 carbons in each of said alkyls; Y is, H, fluoro, chloro, bromo, $(C_1-C_4)$alkyl, $(C_3-C_7)$ cycloalkyl, $(C_1-C_4)$ alkoxy, $(C_1-C_4)$alkylthio and trifluoromethyl; $R^1$ is $(C_1-C_6)$-alkyl, $(C_3-C_7)$cycloalkyl, $(C_4-C_7)$ cycloalkenyl, phenyl, substituted phenyl, phenylalkyl having 1 to 3 carbons in said alkyl, (substituted phenyl)alkyl having 1 to 3 carbons in said alkyl, (substituted phenoxy) alkyl having 1 to 3 carbons in said alkyl, (thiophenoxy)alkyl having 1 to 3 carbons in said alkyl, naphthyl, bicyclo-[2.2.1] hept-2-yl, bicyclo[2.2.1]hept-5-en-2-yl or —$(CH_2)_n$—Q—$R^0$; n is zero, 1 or 2; Q is a divalent radical derived from furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]-thiophene; $R^0$ is H or $(C_1-C_3)$alkyl; and $R^2$ is $(C_1-C_6)$alkyl, $(C_3-C_7)$cycloalkyl, benzyl, furyl, thienyl, pyridyl or

where $R^3$ and $R^4$ are each H, fluoro, chloro, $(C_1-C_4)$-alkyl, $(C_1-C_4)$alkoxy or trifluoromethyl.

That patent also discloses that said 2-oxindole-1-carboxamides are inhibitors of cyclooxygenase and lipoxygenase, possess analgesic activity in mammals and are useful in treatment of pain and alleviation of symptoms of chronic diseases such as inflammation and pain associated with rheumatoid arthritis and osteoarthritis.

U.S. Pat. No. 4,556,672 discloses certain 3-acyl substituted-2-oxindole-1-carboxamides of the formula

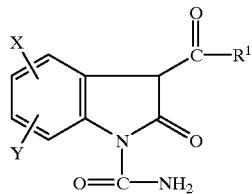

wherein X, Y and $R^1$ are as described above for the compounds of U.S. Pat. No. 4,569,942. The compounds of U.S. Pat. No. 4,556,672 are disclosed as having the same activity as the compounds of U.S. Pat. No. 4,569,942 discussed above.

U.S. Pat. No. 4,861,794 discloses the use of compounds of the formula

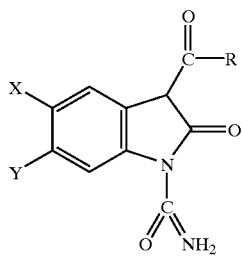

and the pharmaceutically-acceptable base salts thereof wherein X is H, Cl or F, Y is H or Cl and R is benzyl or thienyl to inhibit biosynthesis of interleukin-1 (IL-1) and to treat IL-1 mediated disorders and dysfunctions.

PCT patent application Ser. No. PCT/US88/03658, filed Oct. 18, 1988, describes non-steroidal antiinflammatory agents of the formula

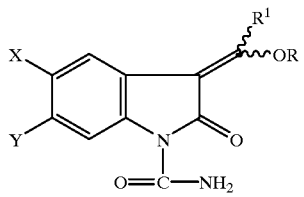

wherein each of X and Y is hydrogen, fluoro or chloro; $R^1$ is 2-thienyl or benzyl; and R is alkanoyl, cycloalkylcarbonyl, phenylalkanoyl, benzoyl and certain substituted benzoyl groups, thenoyl, omega-alkoxycarbonylalkanoyl, alkoxycarbonyl, phenoxycarbonyl, 1-alkoxycarbonyloxy, alkylsulfonyl, methylphenylsulfonyl and dialkyl phosphonate.

Interleukin-1 (IL-1) has been reported to stimulate bone resorption both in vitro and in vivo. Hayward, M. and Fiedler-Nagy, Ch., Agents and Actions, 22, 251–254 (1987). It is also reported therein that IL-1, inter alia, induces the production of prostaglandin $E_2$ ($PGE_2$). $PGE_2$ is a stimulator of bone resorption and has been implicated in bone loss. See Hayward, M. A. and Caggiano, T. J., Annual Reports in Medicinal Chemistry, 22, Sect. IV, Chapter 17, 169–178 (1987). Osteoporosis is defined as a debilitory loss of bone mineral which results in higher fracture rates. See Hayward, M. A. and Caggiano, T. J., supra, and references cited therein.

Interleukin-1 has been reported to be involved in the pathogenesis of many diseases. See Dinarello, C. A., J. Clin. Immunol., 5, 287–297 (1985), the teachings of which are incorporated herein by reference. Further still, elevated levels of IL-1 like material have been found to be associated with psoriasis. Camp, R. D., et al., J. Immunol., 137, 3469–3474 (1986).

DISCLOSURE OF THE INVENTION

The present invention provides novel 3-substituted-2-oxindole compounds of the formula

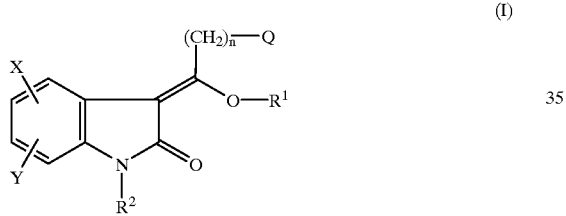

(I)

and the pharmaceutically-acceptable salts thereof, wherein

X is H, F, Cl, Br, ($C_1$–$C_6$)alkyl, ($C_3$–$C_8$)cycloalkyl, $NO_2$, $CF_3$, CN, SH, $S(O)_m R^3$, $OR^4$, $COR^4$ or $CONR^4 R^5$;

Y is H, F, Cl, Br, ($C_1$–$C_6$)alkyl, ($C_3$–$C_8$)cycloalkyl, $NO_2$, $CF_3$, CN, SH, $S(O)_q R^{17}$, $COR^{18}$ $OR^{18}$ or $CONR^{18} R^{19}$;

$R^1$ is H, alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omega-alkoxycarbonylalkanoyl, said alkoxy having one to three carbon atoms and said alkanoyl having three to five carbon atoms, alkoxy carbonyl of two to ten carbon atoms, phenoxycarbonyl, 1-(acyloxv)alkyl wherein acyl has one to four carbon atoms and said alkyl has two to four carbon atoms, 1-(alkoxycarbonyloxy)alkyl wherein said alkoxy has two to five carbon atoms and said alkyl has one to four carbon atoms, alkyl of one to three carbon atoms, alkylsulfonyl of one to three carbon atoms, methylphenylsulfonyl or dialkylphosphonate wherein each of said alkyl is one to three carbon atoms;

$R^2$ is $COR^6$, $CONR^7 R^8$, ($C_1$–$C_6$)alkyl, ($C_3$–$C_8$) cycloalkyl, phenyl or mono- or disubstituted phenyl wherein the substituent or substituents are each Cl, F, Br, ($C_1$–$C_6$)alkyl, ($C_1$–$C_6$)alkoxy or $CF_3$;

Q is

or
$Q^2$-$A^1$;

A is H, F, Cl, Br, I, $CF_3$, $OR^9$, $S(O)_p R^{10}$, $COOR^{11}$, $CONR^9 R^{11}$, CN, $NO_2$, $COR^{10}$, $CH_2 OR^{11}$, $OCOR^{10}$, $NR^9 R^{11}$, $N(R^9)COR^{11}$, $SO_2 NR^9 R^{11}$,

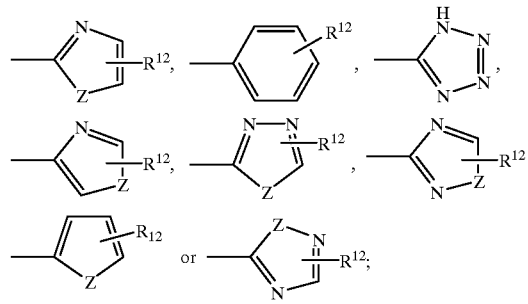

B is H, F, Cl, Br, I, $CF_3$, $OR^{13}$, $S(O)_t R^{14}$, $COOR^{15}$, $CONR^{13} R^{15}$, CN, $NO_2$, $COR^{14}$, $CH_2 OR^{15}$, $OCOR^{14}$, $NR^{13} R^{15}$, $N(R^{13})COR^{15}$ or $SO_2 NR^{13} R^{15}$;
provided that A and B cannot both be H; or A and B are taken together, bonded to the same ring carbon of $Q^1$ and equal oxo, or when A is not H, B is as defined above or ($C_1$–$C_4$)alkyl;

$A^1$ is F, Cl, Br, I, $CF_3$, $OR^9$, $S(O)_p R^{10}$, $COOR^{11}$, $CONR^9 R^{11}$, CN, $NO_2$, $COR^{10}$, $CH_2 OR^{11}$, $OCOR^{10}$, $NR^9 R^{11}$, $N(R^9)COR^{11}$ or $SO_2 NR^9 R^{11}$;

$Q^1$ is

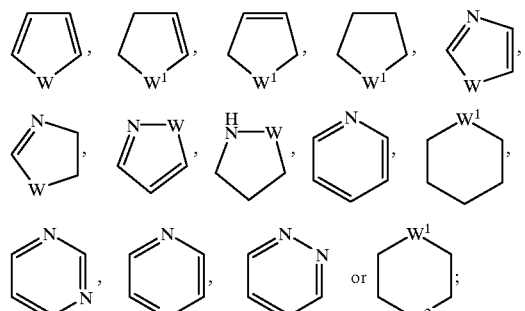

$Q^2$ is

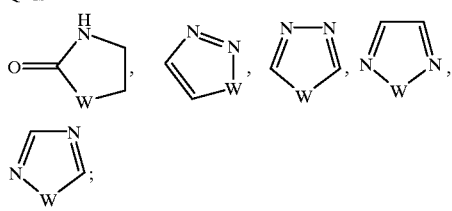

m, n, p, q and t are each zero, one or two;
W and Z are each O, S or $NR^{11}$;
$W^1$ and $W^2$ are each O, S or $NR^{10}$ provided that when one of $W^1$ or $W^2$ is O, S or $NR^{10}$, the other is O or S;
$R^3$, $R^6$, $R^{10}$, $R^{14}$ and $R^{17}$ are each ($C_1$–$C_6$)alkyl or phenyl; $R^5$, $R^8$, $R^{11}$, $R^{15}$ and $R^{19}$ are each H, $(C_1-C_6)$alkyl or phenyl; $R^4$, $R^7$, $R^9$, $R^{13}$ and $R^{18}$ are each H or $(C_1-C_6)$alkyl; and $R^{12}$ is H, F, Cl, Br, $CF_3$ or $(C_1-C_6)$alkyl.

While the compounds of formula I, above, are shown as enols, enol ethers and esters, it is to be understood that when $R^1$ is H the compounds of formula I can assume their tautomeric form of a ketone. That is,

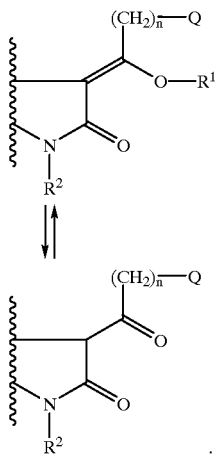

All such tautomeric forms are within the scope of this invention and the appendant claims, and are deemed to be depicted by formula I. Further, the substituents on the exocyclic double bond at the 3-position of the compounds for formula I can be syn, anti or a mixture of both. Thus, the compounds of formula I having the structures

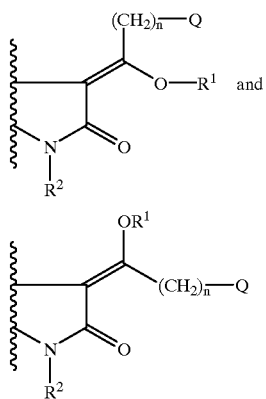

and mixtures thereof are within the scope of this invention and all such isomers are deemed to be depicted by formula I and within the scope of the appendant claims.

The compounds of formula I wherein $R^1$ is other than H are prodrugs of the compounds of formula I wherein $R^1$ is H and the salts thereof.

The term "prodrug" refers to compounds which are drug precursors which, following administration to and absorption by a mammal, release the drug in vivo via some metabolic process.

After gastrointestinal absorption, the prodrugs are hydrolyzed in vivo to the corresponding compounds of formula I where R is H, or a salt thereof. Since the prodrugs of the invention are not enolic acids, exposure of the gastrointestinal tract to the acidic parent compound is thereby minimized.

A preferred group of compounds of this invention is those of formula I, above, wherein $R^1$ is H. Another preferred group of compounds is those of formula I wherein X and Y are each H, F, Cl, $NO_2$, $(C_1-C_3)$alkyl or $CF_3$. Yet another preferred group of compounds is those wherein $R^2$ is $COR^6$, $CONR^7R^8$ or $(C_1-C_6)$alkyl where $R^6$, $R^7$ and $R^8$ are as defined above. Another preferred group of compounds of this invention is those of formula I wherein Q is $Q^1$ where $Q^1$ is

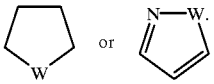

Further preferred compounds are those of formula I wherein Q is $Q^1$ where $Q^1$ is

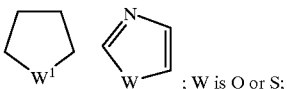; W is O or S;

and $W^1$ is O or S. Another group of preferred compounds is those wherein Q is $Q^2$ where $Q^2$ is

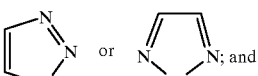; and

W is S.

A more preferred group of compounds is those wherein Q is $Q^1$ where $Q^1$ is

and W is O or S. Particularly preferred compounds are those wherein $R^1$ is H; X and Y are each H, F, Cl, $NO_2$, $(C_1-C_3)$alkyl or $CF_3$; $R^2$ is $COR^6$, $CONR^7R^8$ or $(C_1-C_6)$alkyl where $R^6$, $R^7$ and $R^8$ are as defined above; and Q is $Q^1$ where $Q^1$ is

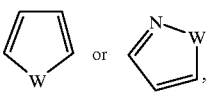, where W is as defined above, or Q is $Q^1$ where $Q^1$ is

where W is O or S, or Q is $Q^1$ where $Q^1$ is

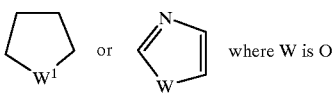 where W is O or S and $W^1$ is O or S, or Q is $Q^2$ where $Q^2$ is

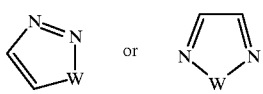

where W is S. Still more preferred compounds are those immediately above wherein W is S, $R^2$ is $CONR^7R^8$ and $R^7$ and $R^8$ are H. Even more preferred are said compounds wherein X is H, Cl or $CF_3$; Y is H, Cl or F; A is Cl, Br, F, $CF_3$, $SCH_3$, $OCH_3$, $COCH_3$ or $CH_2OCH_3$; and B is H, Cl, Br or CH. Other particularly preferred compounds are said compounds wherein n is zero or 1 with n as zero being even more particularly preferred.

Still other preferred groups of compounds are those of formula I and those identified above as preferred, more preferred or particularly preferred wherein A is H, F, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, where $R^9$, $R^{10}$, $R^{11}$, $R^{13}$, $R^{14}$ and $R^{15}$ are as defined above, or A and B are taken together, bonded to the same ring carbon of $Q^1$ and equal oxo or when A is not H, B is as defined above or $(C_1-C_3)$alkyl; and $A^1$ is F with even more preferred compounds being such compounds wherein $R^6$ is $CH_3$; $R^7$ is H and $R^8$ is H or $(C_1-C_4)$alkyl.

The compounds of formula I, above, wherein $R^1$ is H are active as inhibitors of prostaglandin $H_2$ synthase (cyclooxygenase), as inhibitors of 5-lipoxygenase and as inhibitors of interleukin-1 (IL-1) biosynthesis in a mammal. Thus, the compounds of formula I are useful for inhibition of prostaglandin $H_2$ synthase and IL-1 biosynthesis in a mammal. The compounds of formula I, in addition to their usefulness as such inhibitors, per se, are useful as analgesic, antiinflammatory and antiarthritic agents in the treatment of chronic inflammatory diseases in mammals.

The present invention also provides pharmaceutical compositions comprising compounds of formula I. Further, methods of inhibiting prostaglandin $H_2$ synthase and biosynthesis of interleukin-1 in a mammal by administering an effective amount of a compound of formula I to said mammal are provided by this invention. Also provided by the present invention are methods of treating interleukin-1 mediated disorders and immune dysfunctions and/or chronic inflammatory diseases in mammal by administering to said mammal an effective amount of a compound of formula I. Such chronic inflammatory diseases within the scope of this invention include, but are not limited to, psoriasis, rheumatoid arthritis and osteoarthritis.

Further, still, the present invention provides novel carboxylic acids of the formula (II')

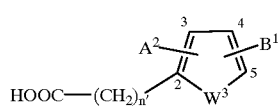

and the salts thereof wherein $A^2$ is H; $B^1$ is at the 4 position and is $S(O)_p$, $R^{16}$ or $COOCH_3$, or $B^1$ is at the 5 position and is $SO_2NHCH_3$ or $B^1$ is at the 4 or 5 position and is $CON(CH_3)_2$,

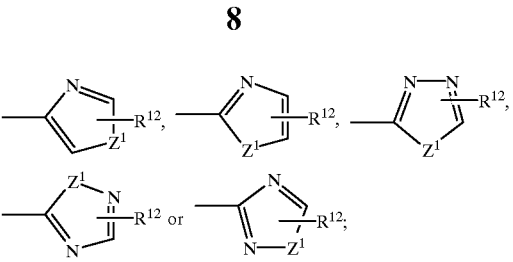

n' is zero; p' is one;

$W^3$ is S; $Z^1$ is O or S; $R^{12}$ is H, F, Cl, Br, $CF_3$ or $(C_1-C_6)$alkyl; and $R^{16}$ is $(C_1-C_4)$alkyl.

The compounds of formula II' are useful as intermediates in the preparation of certain compounds of formula I.

The present invention further provides a novel process for producing certain compounds of formula I, above, wherein $R^1$ is H and $R^2$ is $R^{20}$ as defined below, which comprises reacting a compound of the formula $$Q-(CH_2)_nCOOH \qquad (II)$$

wherein Q and n are as defined above for compounds of formula I, with a molar excess of 1,1'-carbonyldiimidazole in a reaction inert solvent under an inert atmosphere and reacting the product thereof in the presence of a basic agent with a 2-oxindole derivative of the formula (IV')

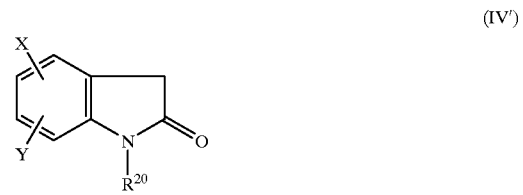

wherein X and Y are as defined above for compounds of formula I and $R^{20}$ is $COR^6$, $CONR^7R^8$, phenyl or mono- or disubstituted phenyl wherein the substituent or substituents are each Cl, F, Br, $(C_1-C_6)$alkyl, $(C_1-C_6)$alkoxy or $CF_3$ where $R^6$, $R^7$ and $R^8$ are as defined above for compounds of formula I, at about 0–50° C., in a reaction inert solvent under an inert atmosphere.

DETAILED DESCRIPTION

REACTION SCHEME A

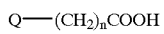

(II)

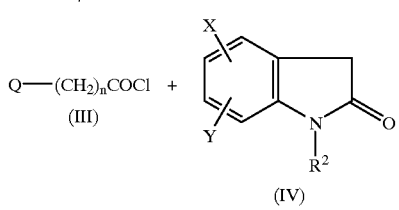

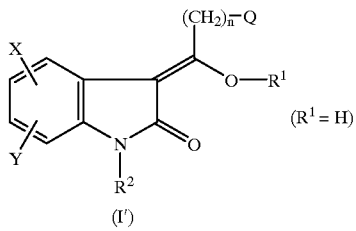

(I')

A method for preparation of compounds of formula I wherein R¹ is H is shown in Reaction Scheme A, above, and is described as follows. The substituted 2-oxindole compounds of formula IV are prepared according to the methods disclosed in U.S. Pat. No. 3,634,453, U.S. Pat. No. 4,556,672, U.S. Pat. No. 4,569,942, U.S. Pat. No. 4,695,571, EP 175551 and the references cited therein. The teachings thereof are incorporated herein by reference. The carboxylic acid compounds of formula II are prepared as described below and are activated by reacting the compound of formula II with a molar excess of thionyl chloride, optionally in the presence of a reaction inert solvent. Appropriate reaction inert solvents are those which will at least partially dissolve one or all of the reactants and will not adversely interact with either the reactants or the product. The resulting carbonyl chloride compound of formula III is dissolved in a reaction inert solvent and slowly added to a solution, cooled to about 0° C., comprising approximately an equimolar amount of the substituted 2-oxindole of formula IV and a molar excess of a basic agent in a reaction inert solvent. The reaction inert solvent is as described above but, in practice, a polar aprotic solvent, such as N,N-dimethylformamide, N,N-dimethylacetamide, N-methylpyrrolidone, or dimethyl sulfoxide, is commonly used. A preferred solvent is N,N-dimethylformamide. A wide variety of basic agents can be used in the reaction between a carbonyl chloride compound of formula III and a substituted 2-oxindole compound of formula IV. However, preferred basic agents are tertiary amines, such as trimethylamine, triethylamine, tributylamine, N-methylmorpholine, N-methylpiperidine, pyridine and 4-(N,N-dimethylamino)pyridine, with a particularly preferred basic agent being 4-(N,N-dimethylamino)pyridine. Following addition of the carbonyl chloride compound of formula III to the substituted 2-oxindole compound of formula IV, the reaction is permitted to warm to about 25° C. and permitted to continue at that temperature. Reaction times of about 30 minutes to two hours are common. At the end of the reaction, the reaction mixture is acidified and then the product is recovered such as by filtration. The product can then be washed, dried and further purified by standard methods such as recrystallization.

REACTION SCHEME B

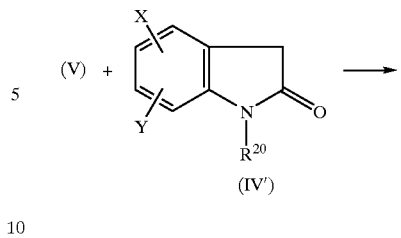

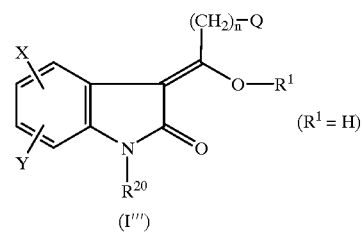

(V) +

(IV')

(I''')

Alternatively, the compounds of formula I wherein R¹ is H can be prepared by the novel process of this invention shown in Reaction Scheme B, above, and described below. A carboxylic acid compound of formula II, prepared as described below, is reacted with a slight molar excess of 1,1'-carbonyldiimidazole in a reaction inert solvent. The reaction is carried out at about 25° C. and is stirred under an inert atmosphere. The reaction is permitted to proceed for about two hours whereupon the entire reaction mixture is added to a mixture comprising an approximately equimolar amount of a substituted 2-oxindole compound of formula IV, prepared as described above, in the presence of a molar excess of a basic agent in a reaction inert solvent under an inert atmosphere. Appropriate reaction inert solvents are those as described above for Reaction Scheme A and a preferred solvent for use herein is N,N-dimethylformamide. An inert atmosphere is obtained by carrying the reaction out under an inert gas such as nitrogen or argon. Appropriate basic agents are those as described above for Reaction Scheme A and preferred basic agents are 4-(N,N-dimethylamino)pyridine and triethylamine.

Another method useful for preparation of compounds of formula I wherein R¹ is H comprises the attachment of the $$Q-(CH_2)_n-\overset{O}{\underset{\|}{C}}-$$

substituent to the 3-position of the requisite 2-oxindole compound of the formula (VI)

by reacting a compound of the formula VI with a derivative of the appropriate acid of formula II, above, according to the methods described in U.S. Pat. No. 4,556,672. The resulting compounds of the formula

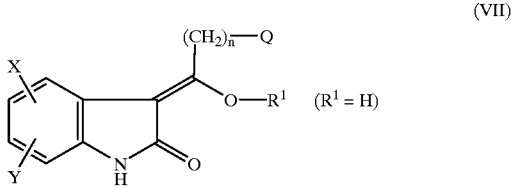

(VII)

are then converted to the corresponding compounds of formula I', above, according to the methods described in U.S. Pat. No. 3,634,453; U.S. Pat. No. 4,556,672; U.S. Pat. No. 4,569,942; U.S. Pat. No. 4,695,571; EP 175551 and the references cited therein.

REACTION SCHEME C

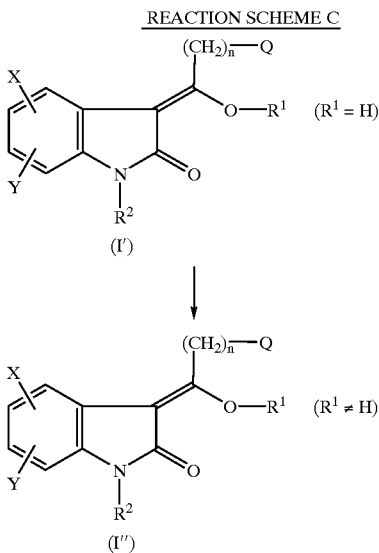

There are two methods which can be employed in the synthesis of compounds of formula I wherein $R^1$ is other than hydrogen (formula I" in Reaction Scheme C). The first method comprises treating a solution of the appropriate substituted-2-oxindole of formula I', above, and an equimolar amount of triethylamine in a reaction-inert solvent such as chloroform, at 0° C. with an equimolar amount, plus a slight excess of the requisite acid chloride, chloroformate, oxonium salt or alkylating agent. After 2 hours, the reaction is allowed to warm to room temperature and remain for about 2–3 hours. If the starting oxindole is not completely reacted the mixture is cooled to 0° C., additional acylating or alkylating agent is added and the process repeated until all the starting oxindole is consumed.

The product is isolated from the reaction solvent by filtration and washed with 1N hydrochloric acid followed by partitioning in an organic solvent and a saturated sodium bicarbonate solution. The organic layer is dried, filtered and concentrated in vacuo. The resulting product is purified by recrystallization or chromatography.

The second procedure, useful in the preparation of the compounds of the present invention wherein $R^1$ is not hydrogen, consists of contacting, in an anhydrous reaction-inert solvent such as acetone, the appropriate substituted-2-oxindole of formula I', a three-fold molar excess of the requisite alpha-chloroalkylcarbonate, a five-fold molar excess of sodium iodide and a two-fold molar excess of anhydrous potassium carbonate (dried under high vacuum at 165° C. for 1 hour) and heating said reaction mixture at reflux for 16 hours.

The reaction mixture is cooled, diluted with water and the product extracted with a water-immiscible solvent, such as diethyl ether or chloroform. The combined extracts are dried, filtered and the filtrate concentrated in vacuo. The resulting crude product is purified by recrystallization and/or chromatography.

Certain of the carboxylic acid compounds of formula II are known and the carboxylic acid compounds of formula II including the novel carboxylic acids of formula II' are prepared according to known methods, or methods analogous to known methods. Such methods may include the preparation of the corresponding esters or nitriles of the respective carboxylic acids in which cases hydrolysis by known procedures yields the carboxylic acid of interest. For such methods, consult: Taylor, E. C., et al., J.O.C. 50:1002 (1985); Noto, R., et al., J. Chem. Soc. P.T. II, 689 (1987); Schick, J. W., et al., J. Am. Chem. Soc. 70:286 (1948); Carpenter, A. J., et al., Tetrahedron 41:3808 (1985); Gronowitz, S., et al., Arkiv. for Kemi. 21:265 (1963); Benkeser, R. A., et al., J.O.C. 38:3660 (1973); Corral, C., et al., Heterocycles 23: 1431 (1985); Iriarte, J., et al., J. Het. Chem. 13:393 (1976); Reinecke, M. G., et al., Synthesis, 327 (1980); Lawesson, S. O., Arkiv. for Kemi. 11:317 (1957); Gronowitz, S., Arkiv. for Kemi. 8:87 (1955); Knight, D. W., et al., J. Chem. Soc. P.T.I., 791 (1983); Gronowitz, S., Arkiv. for Kemi. 12:239 (1958); Sice, J., J. Am. Chem. Soc. 75:3697 (1953); Bohlmann, F., et al., Chem. Ber. 106:497 (1973); Thames, S. F., et al., J. Het. Chem. 3:104 (1966); Arndt, F., et al., Chem. Ber. 94:1757 (1961); Cymerman-Craig, J., et al., J. Chem. Soc.:237 (1954); Lora-Tamayo, M., et al., Anales Real Soc. Espan. Fis. Quim. Ser. B 62:187 (1966); Nemec, N., et al., Coll. Czech. Chem. Comm. 39:3527 (1974); Janda, M., et al., Coll. Czech. Chem. Comm. 27:1191 (1962); Carpenter, A. J., et al., Tetrahedron Letters 26:1777 (1985); Satonaka, H., Bull. Chem. Soc. Japan 56:2463 (1983); Kinoshita, T., et al., Bull. Chem. Soc. Japan 48:1865 (1975); Schwertner, E., et al., CA 88:105790c (1978); Takaya, T., et al., Bull. Chem. Soc. Japan 41:2086 (1968); Kim, H., et al., J. Med. Chem. 29:1374 (1986); Dostert, P., et al., Eur. J. Med. Chem.—Chim. Ther. 17:437 (1982); Sato, N., et al., J. Heterocyclic Chem. 19:407 (1982); Ladruee, D., et al., Heterocycles 22:299 (1984); Leanza, W. J., et al., JACS 75:4086 (1953); Barlin, G. B., et al., Aust. J. Chem. 30:2319 (1977); Gregory, G. I., et al., JCS P.T.1:47 (1973); Moriarty, R. M., et al., JACS 89:5958 (1967); Ross, J. M., et al., JACS 86:2861 (1964); Goerdeler, J., et al., Chem. Ber. 99:1618 (1966); Demaree, P., et al., Can. J. Chem. 55:243 (1977); U.S. Pat. No. 4,001,238; Kawazu, M. et al., J. Med. Chem. 15:914 (1972); Buckle, D. R., et al., JCS P.T.1:627 (1982); Naik, S. R., et al., JOC 38:4353 (1973); Okada, M., et al., Marcomolecules 19:503 (1986); Ondetti, M. A., et al., CA 92:76268p (1980); Neth. Appl. 6,503,440, Sep. 20, 1965; Kenley, R. A., et al., CA101:90841f (1984); Schmidt, U., et al., CA 96:104572m (1982); Lukes, R. et al., Chem. listy 51:1510 (1957); Krowicki, K., et al., JOC 52:3493–3501 (1987); Goya, P., et al., Heterocycles 24:3451 (1986); Montero, J. L., et al., J. Heterocyclic Chem. 15:929 (1978); Yasuda, N., et al., J. Heterocyclic Chem. 24:303 (1987); Hosmane, R. S., et al., Heterocycles 24:2743 (1986); Rapoport, H., et al., Environ. Health Persp. 67:41 (1986); Kravchenko, T. B., et al., CA107:189533t (1987); Stanovnik, B., et al., Heterocycles 12:761 (1979); Smith, R. C., et al., Biochem. Pharmacol. 36:1457 (1987); Bosso, C., et al., Org. Mass Spectrom. 20:263 (1985); Takagi, T., et al., CA83:164172x (1975); Bende, Z., et al., CA98:89254e (1983); Sarodnick, G., et al., CA101:38426k (1984); Fletton, R. A., et al., CA107:39474k (1987); Solomon, D. M., et al., Heterocycles 26:651 (1987); Erlenmeyer, H., et al., Helv. Chim. Acta 27:1432 (1944); CA98:95673g (1983); U.S. Pat. No. 4,437,876; Hundle, B. S., et al., Biochemistry 26:4505 (1987); Marutani, Y., et al., CA104:193202q (1986); Golubev, A. A., et al., CA107:236584x (1987); Higuchi, M., et al., CA104:216392t (1986); Nakagawa, M., et al., Tetrahedron Letters 27:6087–6090 (1986); Pereira, M. A., et al., CA11:165001t (1984); Fujii, S., et al., CA102:45788d (1985); Bredereck, H., et al., Chem. Ber. 97:1414 (1964); Howe, R. K., et al., CA95:80933f (1981); Ibarra, C. A., et al., Tetrahedron Letters 26:243 (1985); Hoppe, D., Justus Liebigs Ann. Chem.:1843 (1976); Evans, D. L., et al., JOC 44:497 (1979); Ozaki, Y., et al., Synthesis (1979) 216; Ehler, K. W., et al., CA87:136361x (1977); Scolastico, C., et al., Synthesis:850 (1985); Corsico Coda, A., et al., Heterocycles 26:745 (1987); Fields, R., et al., CA90:152072w (1979); Farina, F., et al., Heterocycles 24:2587 (1986); Manaev, Y. A., et al., CA98:71993k (1983); Beck, J. R., CA107:23332b (1987); Aoki, I., et al., CA107:176057r (1987); Beck, J. R., et al., J. Heterocyclic Chem. 24:267 (1987); Sato, T., et al., CA107:39807w (1987); Ege, G., et al., Chem. Ber. 120:1375 (1987); Klein, H. J. et al., CA102:203932c (1985); Perevalov, V. P. et al., CA101:171198d (1984); Hamilton, H. W., CA107:59053a (1987); Sabate-Alduy, C., et al., CA87:23137k (1977); Bastide, J., et al., Tetrahedron 30:3355 (1974); Chrzaszcewska, A., Lodz. Tow. Navk. Wydz. III, 12:119 (1967)(CA71:124091r (1969)); British Patent 705,950 (CA49:2233 (1955)); and DeNardo, M., CA87:118063x (1977); and references cited therein. The teachings thereof are incorporated herein by reference.

The compounds of the formula I wherein $R^1$ is H are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, as appropriate, or, in the case of aqueous solutions, by lyophilization. Typical salts of the compounds of formula I which can be prepared are primary, secondary and tertiary amine salts, alkali metal salts and alkaline earth metal salts. Especially valuable are the ethanolamine, diethanolamine and triethanolamine salts.

Basic agents suitably employed in salt formation belong to both the organic and inorganic types, and they include organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides, such as sodium ethoxide and potassium methoxide; hydrides, such as calcium hydride and sodium hydride; and carbonates, such as potassium carbonate and sodium carbonate.

The ability of the compounds of formula I to inhibit interleukin-1 biosynthesis is demonstrated by the assay procedure described below.

C3H/HeN mice (Charles River, Wilmington, Mass.) are sacrificed by cervical dislocation and their abdomens sprayed with 70% ethanol to prevent bacterial contamination of the subsequent cellular preparation. Into the peritoneum of each mouse is injected 8 ml of RPMI[1] containing 5% FCS[2], penicillin-streptomycin (100 units/ml–100 ug/ml) and glutamine (2 mM). The peritoneum is kneaded to help free cells. Then, an incision through the skin of the abdomen is made to expose the underlying muscle layer. The peritoneal fluid is removed with a 20 gauge needle by inserting the needle, bevel down, through the exposed muscle layer just below the sternum. The peritoneal fluid from six mice is pooled in a plastic conical tube and microscopically examined for bacterial contamination. Uncontaminated fluid is centrifuged at about 600×g for six minutes and the supernatant decanted. The pelleted cells from five to six tubes are combined and resuspended in a total of 20 ml of RPMI-FCS[3]. The cell number is then ascertained using a hemacytometer and cell viability determined with Trypan Blue staining also using a hemacytometer. The cells are then diluted to $3 \times 10^6$ cells/ml using RPMI-FCS. To the wells of a 35 mm well plate is added 1 ml of the above cell suspension. The cells are incubated for 2 hours at 37° C. in a 5% $CO_2$ atmosphere to cause adherence of the macrophages to the walls of the wells. The supernatant is removed by swirling the wells vigorously and decanting. The adherent cells (i.e., macrophages) are washed twice with RPMI-SF[4]. To the wells containing adherent cells is added 1 ml of the compound under study at concentrations ranging from 0.1 to 100 ug/ml in RPMI-SF or 1 ml of RPMI-SF as a control. Then, 100 ul of LPS[5] in RPMI-SF (1 mg/5 ml) is added to each well. The plates are incubated at 37° C. in a 5% $CO_2$ atmosphere for 24 hours. The supernatants are removed and either assayed for IL-1 immediately or otherwise refrigerated or frozen for subsequent assay.

[1]RPMI-1640 medium (Hazelton Research Products, Inc., Lenexa, Kans.)
[2]Petal calf serum which has been screened for good responsiveness to IL-1 in the thymocyte assay (Hyclone Laboratories, Logan, Utah) and for low spontaneous proliferation in the absence of IL-1.
[3]RPMI-1640 medium containing 5% fetal calf serum.
[4]RPMI containing penicillin-streptomycin (100 units/ml–100 ug/ml) and glutamine (2 mM).
[5]Refined purified lipopolysaccharide from *Salmonella minnesota* which has been checked to determine that the C3H/HeJ mouse is unresponsive thereto.

The supernatants are assayed quantitatively for IL-1 according to the receptor binding assay described below. A standard curve is generated as follows. EL4-6.1 murine thymoma cells [$10–15 \times 10^6$ cells in 0.4 ml binding buffer (RPMI 1640, 5% FCS, 25 mM HEPES, 0.01% $NaN_3$, pH 7.3)] are added to varying amounts of unlabeled murine rIL-1α [recombinant IL-1α produced in *Escherichia coli* from the published sequence of amino acids 115–270 for IL-1α, Lomedico, P. M., et al., Nature, 312, 458–462 (1984)] (40 pg to 40 ng in 0.5 ml buffer) and incubated for 1 hour at 4° C. with continuous shaking, after which 0.8 ng (0.1 ml) of human $^{125}$I-rIL-1β (New England Nuclear, Boston, Mass.) is added and shaking continued for an additional 3 hours. Samples are filtered with a Yeda apparatus (Linca Co., Tel-Aviv, Israel) through Whatman GF/C2.4 cm glass fiber filters (blocked with 0.5% powdered milk for 2 hours at 37° C.) and washed once with 3 ml of ice-cold buffer. Filters are counted in a Searle gamma counter and non-specific binding is taken as the cpm bound in the presence of 200 ng unlabeled rIL-1α. A Hill calibration curve is constructed by plotting log (Y/100-Y) vs. log C where Y represents the percent of control $^{125}$I-rIL-1β binding and C is the concentration of unlabeled rIL-1α. A linear least-squares line is fitted through Y values between 20 to 80%. Then, to quantitate IL-1 levels in the supernatants obtained as described above, diluted supernatants replace rIL-1α in the above protocol and measured percent binding values are used to determine IL-1 concentrations from a standard Hill plot. Each dilution is assayed in duplicate and generally only dilutions with Y values between 20 to 80% are used to calculate average IL-1 levels.

The ability of the compounds of formula I to inhibit prostaglandin $H_2$ synthase and 5-lipoxygenase is demonstrated by the following assay procedure. By employing the procedure described below the levels of known products of prostaglandin $H_2$ synthase and 5-lipoxygenase are measured for cells treated with the compound under study with inhibition of prostaglandin $H_2$ synthase and/or 5-lipoxygenase being evidenced by a decrease in the amount of, or absence of, the known products of those enzymes.

RBL-1 cells, maintained in monolayer, are grown for 1 to 2 days in Spinner culture in Minimum Essential Medium (Eagle) with *Earle's* Salts plus 15% fetal bovine serum supplemented with antibiotic/antimycotic solution (Gibco) according to the method of Jakschik, B. A., et al., Nature 287:51–52 (1980). The cells are washed twice and resuspended in cold RPMI 1640 to a cell density of $4 \times 10^6$ cells/ml. Then, a 0.25 ml aliquot of the compound under study at the desired concentration in RPMI 1640 is equilibrated at 37° C. for 5 minutes. To the equilibrated aliquot is added a 0.25 ml aliquot of prewarmed cell suspension and the mixture is incubated at 37° C. for 5 minutes. A 10 ul solution containing $^{14}$C-arachidonic acid and A-23187 (calcium ionophore, Sigma Chemical) is added and the mixture is incubated at 37° C. for another 5 minutes. Then, 267 ul of acetonitrile/0.3% acetic acid is added and the mixture is allowed to stand on ice for 30 minutes. The tube containing the mixture is vortexed, clarified by centrifugation (3000 rpm, 10 minutes) and the supernatant is decanted and re-centrifuged for 2 minutes in a microfuge at high speed. A 100 ul aliquot of the supernatant then is analyzed by HPLC on a Perkin Elmer-HS (3 micron) column using a gradient solvent system of acetonitrile/$H_2O$ with 0.1% trifluoroacetic acid and a flow rate of 2 ml/min. Radioactivity detection is accomplished with a Berthold LB504 Radioactivity Monitor equipped with an 800 ul flow cell mixing 2.4 ml/min of Omnifluor (Trademark of New England Nuclear, Boston, Mass.) with the column effluent. Quantitation of the eluted radioactivity is carried out by the use of a Spectra Physics SP4200 computing integrator. The data so obtained is used in a data-reduction program where the integration units for each product are calculated as percent of the total integration units and compared to average control levels.

The compounds of formula I possess analgesic activity. This activity is demonstrated in mice by showing blockage of the abdominal stretching induced by administration of 2-phenyl-1,4-benzoquinone (PBQ). The method used is based on that of Siegmund et al., Proc. Soc. Exp. Biol. Med., 95, 729–731, (1957), as adapted for high throughput (see further Milne and Twomey, Agents and Actions, 10, 31–37, [1980]). All mice were fasted overnight prior to drug administration and testing.

The compounds of formula I are dissolved or suspended in a vehicle consisting of ethanol (5%), emulphor 620 (a mixture of polyoxyethylene fatty acid esters, 5%) and saline (90%). This vehicle also serves as control. Doses were on a logarithmic scale (i.e., . . . 0.32, 1.0, 3.2, 10, 32 . . . mg/kg). The route of administration is oral, with concentrations varied to allow a constant dosage volume of 10 ml/kg of body weight. The aforesaid method of Milne and Twomey is used to determine efficacy and potency. Mice are treated with compounds orally, and one hour later received PBQ, 2 mg/kg, intraperitoneally. Individual mice are then immediately placed in a warmed lucite chamber, and, starting five minutes after PBQ administration, the number of abdominal constrictions during the subsequent 5 minutes is recorded. The degree of analgesic protection (% MPE) is calculated on the basis of suppression of abdominal constriction relative to counts from concurrent control animals run on the same day. At least four such determinations (N=5) provide dose-response data for generation of an $MPE_{50}$, the best estimate of the dose that reduces abdominal constriction to 50% of control levels.

The compounds of formula I also possess antiinflammatory activity. This activity is demonstrated in rats by a method based on the standard carrageenin induced rat foot edema test (Winter et al., Proc. Soc. Exp. Biol. Med., 111, 544 [1963]).

Unanesthetized, adult, male, albino rats of 150 g to 190 g body weight are numbered, weighed, and an ink mark placed on the right lateral malleolus. Each paw is immersed in mercury exactly to the ink mark. The mercury is contained in a glass cylinder, connected to a Statham Pressure Transducer. The output from the transducer is fed through a control unit to a micro-voltameter. The volume of mercury displaced by the immersed paw is read. Drugs are given by gavage. One hour after drug administration, edema is induced by injection of 0.05 ml of 1% solution of carrageenin into the plantar tissue of the marked paws. Immediately thereafter, the volume of the injected foot is measured. The increase in foot volume 3 hours after the injection of carrageenin constitutes the individual inflammatory response.

The analgesic activity of the compounds of formula I makes them useful for acute administration to mammals for the control of pain, e.g., post-operative pain and the pain of trauma. Additionally the compounds of formula I are useful for chronic administration to mammals for the alleviation of the symptoms of chronic diseases, such as the inflammation of rheumatoid arthritis, and the pain associated with osteoarthritis and other musculoskeletal disorders.

The ability of the compounds of formula I to inhibit IL-1 biosynthesis makes them useful as IL-1 biosynthesis inhibitors, per se. It also makes them useful in treating IL-1 mediated disorders and immune dysfunctions in a mammal. Said IL-1 mediated disorders include, but are not limited to bone and connective tissue metabolism disorders such as osteoporosis, periodontal disease and tissue scarring. IL-1 mediated immune dysfunctions include, but are not limited to, allergy and psoriasis.

The ability of the compounds of formula I to inhibit prostaglandin $H_2$ synthase makes them useful as prostaglandin $H_2$ synthase inhibitors, per se, as the functioning of that enzyme is known to be involved with the pathogenesis of arthritic joints in mammals.

When a compound of formula I or a pharmaceutically-acceptable salt thereof is to be used as an inhibitor of IL-1, an inhibitor of prostaglandin $H_2$ synthase, an analgesic agent or an antiinflammatory agent, it can be administered to a mammalian subject either alone, or, preferably, in combination with pharmaceutically-acceptable carriers or diluents in a pharmaceutical composition, according to standard pharmaceutical practice. A compound can be administered orally or parenterally. Parenteral administration includes intravenous, intramuscular, intraperitoneal, subcutaneous and topical administration.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use of a compound of formula I of this invention, the compound can be administered, for example, in the form of tablets or capsules, or as an aqueous solution or suspension. In the case of tablets for oral use, carriers which are commonly used include lactose and corn starch and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solutes should be controlled to render the preparation isotonic.

When a compound of formula I or salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, for acute administration to relieve pain, an effective analgesic response eliciting dose in most instances will be about 5 mg to 500 mg as needed (e.g., every four to twenty-four hours). For chronic administration to alleviate (treat) inflammation and pain, inhibit IL-1 biosynthesis and/or inhibit prostaglandin $H_2$ synthase in most instances an effective dose will be from about 5 mg to 1.0 g per day, and preferably 50 mg to 500 mg per day, in single or divided doses. On the other hand, it may be necessary to use dosages outside these limits in some cases.

The following Examples are illustrative of this invention and are not to be construed as limiting in any way the scope hereof.

EXAMPLE 1

4-Methylsulfinyl-2-thiophenecarboxylic acid

A stirred solution of 2.46 g (14.1 mmoles) of 4-methylthio-2-thiophenecarboxylic acid (prepared as described in Example 28 below) in 150 ml dichloromethane and 10 ml methanol was cooled to icebath temperature. A 120 ml dichloromethane solution of 2.82 g (13.9 mmoles) of m-chloroperoxybenzoic acid (technical grade, 80–85%) was slowly added to the cooled reaction solution. After 1 hour the reaction was essentially complete with a colorless precipitate forming. The precipitate was filtered and dried to give 1.18 g (6.20 mmoles) of desired compound as a colorless solid, m.p. 188–190° C. The concentrated mother liquor was chromatographed (silica gel) to give an additional 0.83 g (4.36 mmoles) of desired 4-methylsulfinyl-2-thiophenecarboxylic acid, total yield 75% (10.56 mmoles).

Analysis: Calculated for $C_6H_6O_3S_2$: C, 37.88; H, 3.18%. Found: C, 37.89; H, 3.18%. EIMS (m/z): 190 ($M^+$, 45%) and 175 ($M^+$—$CH_3$). $^1$HNMR (DMSO-$d_6$) delta, 13.4 (1H, exchangeable), 8.27 (1H, d, J=1.5 Hz), 7.96 (1H, d, J=1.5 Hz) and 2.86 (3H, s). $^{13}$CNMR (DMSO-$d_6$) delta 162.1, 146.4, 137.2, 131.7, 128.9 and 42.2. ir(potassium bromide): 3420, 2550, 1705, 1245, 1015 $cm^{-1}$.

EXAMPLE 2

5-(N-Methylaminosulfonyl)-2-thiophenecarboxylic acid

Lithium diisopropylamide was prepared by slowly adding 17.5 ml (43.8 mmoles) of 2.5M n-butyllithium in hexanes to a cooled (2-propanol/dry ice) tetrahydrofuran (200 ml) solution of diisopropylamine (7.0 ml, 50.0 mmoles) with the reaction temperature maintained below −60° C. After 5 minutes the reaction solution was warmed to room temperature for 30 minutes and then cooled to below −70° C. again. A 100 ml tetrahydrofuran solution of 3.54 g (20.0 mmoles) of 2-(N-methylaminosulfonyl)-thiophene (prepared according to Slocum, D. W., et al., JOC 38, 4189 (1973)) was added slowly with the reaction temperature controlled below −70° C. After complete addition the reaction was stirred for 30 minutes and then excess carbon dioxide was bubbled through the solution. The solution was then warmed to 5° C. and quenched with 50 ml of 1N sodium hydroxide. A 300 ml portion of diethyl ether was added to the aqueous tetrahydrofuran solution and the phases were separated in a separatory funnel. The organic layer was extracted with 50 ml of 1N sodium hydroxide. Both basic aqueous solutions were combined, washed with 50 ml of diethyl ether and acidified with concentrated hydrochloric acid. The acidic aqueous mixture was extracted with diethyl ether (2×100 ml). The ether solution was washed with brine, dried over magnesium sulfate, filtered and concentrated in vacuo to 3.38 g (15.3 mmoles) of desired thiophenecarboxylic acid as a colorless solid, m.p. 145–148° C. Total yield was 76%.

Analysis: Calculated for $C_6H_7NO_4S_2$: C, 32.57; H, 3.19; N, 6.33%. Found: C, 32.43; H, 3.08; N, 6.30%. EIMS (m/z): 221 ($M^+$, base), 191 ($M^+$—NHMe, 98%), 157 (unknown, 95%), 127 (unknown, 45%) and 115 (unknown, 73%). $^1$HNMR (DMSO-$d_6$) delta, 7.92 (1H, exchangeable), 7.74 (1H, d, J=4.0 Hz), 7.58 (1H, d, J=4.0 Hz) and 2.51 (3H, d, J=5.2 Hz); ir(potassium bromide): 3440 br, 3000 br, 1680, 1170 $cm^{-1}$.

EXAMPLE 3

5-Iodo-2-thiophenecarboxylic acid

The title compound has been described by Schick, J. W., et al., J. Am. Chem. Soc. 70:286 (1948), and was prepared according to the following procedure. A 25 ml (62.5 mmoles) volume of a 2.5M hexane solution of n-butyllithium was slowly added by syringe to a cooled (dry ice/2-propanol) 100 ml tetrahydrofuran solution of 9.0 ml (64.2 mmoles) of diisopropylamine. The solution was maintained below −60° C. during n-butyllithium addition. After addition, the cooling bath was removed and the solution allowed to reach room temperature (22° C.), and then cooled again below −60° C. To the cooled reaction vessel, 3.2 g (25.0 mmol) of 2-thiophenecarboxylic acid dissolved in 100 ml of tetrahydrofuran was slowly added. Thirty minutes after complete addition of 2-thiophenecarboxylic acid, approximately 17.2 g (87.8 mmoles) of iodotrifluoromethane was condensed into the reaction. After 5 minutes the cooling bath was removed and the reaction warmed to 0° C. and quenched with 50 ml of water. The basic aqueous solution was washed with 500 ml of diethyl ether. The ether solution was extracted with 50 ml of 1N sodium hydroxide and the two aqueous solutions were combined and washed with ether. The basic solution was acidified and extracted three times with 100 ml of diethyl ether. Drying of the organic solution with anhydrous magnesium sulfate followed by filtration and concentration gave a crude solid product. Partial purification was achieved by reprecipitation of the solid product from hot aqueous ethanol to give 3.79 g of slightly impure desired product as a mixture of dark red solid and yellow crystals. Recrystallization of the solid mixture gave 2.18 g (8.58 mmoles, 34% yield) of pure title compound as light yellow needles, m.p. 132–134° C. (hexanes).

Analysis: Calculated for $C_5H_3IO_2S$: C, 23.64; H, 1.19%. Found: C, 23.86; H, 1.10%. EIMS (m/z): 254 ($M^+$, base), 237 ($M^+$—OH, 79%), 209 ($M^+$—$CO_2H$, 5%), 127 ($M^+$—I, 18%) and 82 ($C_4H_2S$, 36%); $^1$HNMR ($CDCl_3$)delta, 7.50 (1H, d, J=3.9 Hz) and 7.29 (1H, d, J=3.9 Hz); ir ($CHCl_3$): 2977 br, 2565, 1679 and 1410 cm$^{-1}$.

EXAMPLE 4

5-[(N,N-Dimethylamino)carbonyl]-2-thiophenecarboxaldehyde

To a solution of 5-formyl-2-thiophenecarboxylic acid (prepared according to Carpenter, A. J., et al., Tetrahedron 41:3808 (1985)) (2.75 g, 17.61 mmoles) in 75 ml of tetrahydrofuran was added 1,1'-carbonyl-diimidazole (3.71 g, 22.88 mmoles), the solution stirred under dry argon for ½ hours and treated with excess gaseous dimethylamine. The solution was concentrated in vacuo to an oil which was dissolved in ethyl acetate (100 ml) and extracted with 1N hydrochloric acid (2×50 ml) followed by 5% sodium bicarbonate (2×50 ml). Each of the aqueous layers was backwashed with ethyl acetate (2×50 ml) and the combined organic layers were dried (magnesium sulfate). Concentration in vacuo furnished a pale yellow solid (2.42 g, 75%). EIMS (m/z): 183 ($M^+$, 82%), 154 ($M^+$—CHO, 7%), 139 ($M^+$—$(CH_3)_2N$, base) and 111 ($M^+$—$(CH_3)_2NCO$, 59%); $^1$HNMR ($CDCl_3$) delta, 9.91 (1H, s), 7.67 (1H, d, J=4.0 Hz), 7.35 (1H, d, J=4.0 Hz), 3.13 (6H, br s). This material was used directly without further purification.

EXAMPLE 5

5-[(N,N-Dimethylamino)carbonyl]-2-thiophenecarboxylic acid

A 2.39 g (13.04 mmoles) portion of the crude 5-[(N,N-dimethylamino)carbonyl]-2-thiophenecarboxaldehyde was added to a stirred suspension of silver oxide prepared by adding 2.29 g (57.13 mmoles) of sodium hydroxide 5.85 g (34.44 mmoles) of silver nitrate in 100 ml of water. After stirring at ambient temperature for fifteen minutes and filtration through a pad of diatomaceous earth the filtrate was acidified from pH 12 to pH 2 with concentrated hydrochloric acid and extracted with ethyl acetate. The extracts were dried (magnesium sulfate) and concentrated in vacuo to furnish a white solid (2.01 g, 77%). An analytical sample was obtained by trituration with warm ethyl acetate, m.p. 158–159° C.

Analysis: Calculated for $C_8H_9NO_3S$: C, 48.23; H, 4.55; N, 7.03%. Found: C, 48.30; H, 4.42; N, 6.79%. EIMS (m/z): 199 ($M^+$, 68%), 155 ($M^+$—$(CH_3)_2N$, base), 111 ($M^+$—$(CH_3)_2NCO$, 44%); $^1$HNMR (DMSO-$d_6$) delta, 7.66 (1H, d, J=4.0 Hz), 7.46 (1H, d, J=4.0 Hz), 3.09 (6H, s); ir (potassium bromide): 3430, 1710, 1594, 1246 cm$^{-1}$.

EXAMPLE 6

4-[(N,N-Dimethylamino)carbonyl]-2-thiophenecarboxaldehyde

To a solution of 2-formyl-4-thiophenecarboxylic acid (prepared according to Gronowitz, S., et al., Arkiv. for Kemi. 21:265 (1963)) (1.24 g, 7.94 mmoles) in 50 ml of tetrahydrofuran was added 1,1'-carbonyldiimidazole (1.80 g, 11.10 mmoles), the solution stirred under dry argon for 1½ hours and treated with excess gaseous dimethylamine. The solution was concentrated in vacuo to an oil which was dissolved in ethyl acetate (60 ml) and extracted with 1N hydrochloric acid (1×30 ml) followed by 5% sodium bicarbonate (1×30 ml). Each of the aqueous extracts was backwashed with ethyl acetate (2×50 ml) and the combined organic layers were dried (magnesium sulfate). Concentration in vacuo furnished a tan solid (1.15 g, 79%). EIMS (m/z): 183 ($M^+$, 31%), 155 ($M^+$—CO, 38%), 139 ($M^+$—$(CH_3)_2N$, base) and 111 ($M^+$—$(CH_3)_2NCO$, 25%); $^1$HNMR (DMSO-$d_6$) delta, 9.89 (1H, d, J=1.4 Hz), 7.89 (1H, dd, J=1.5, 1.4 Hz), 7.86 (1H, d, J=1.5 Hz), 3.08 (6H, s). This material was used directly without further purification.

EXAMPLE 7

4-[(N,N-Dimethylamino)carbonyl]-2-thiophenecarboxylic acid

A 1.12 g (6.11 mmoles) portion of the crude 4-[(N,N-dimethylamino)carbonyl]-2-thiophenecarboxaldehyde was added to a stirred suspension of silver oxide prepared by adding 1.08 g (26.90 mmoles) of sodium hydroxide to 2.74 g (16.14 mmoles) of silver nitrate in 40 ml of water. After stirring at ambient temperature for fifteen minutes the mixture was filtered through diatomaceous earth, acidified from pH 12 to pH 2 with concentrated hydrochloric acid and saturated with solid sodium chloride. After extraction with ethyl acetate (3×75 ml) the dried (magnesium sulfate) extracts were concentrated in vacuo to a pale yellow crystalline solid (1.10 g, 90%). An analytical sample was obtained by trituration with warm ethyl acetate, m.p. 112–114° C.

Analysis: Calculated for $C_8H_9NO_3S$: C, 48.23; H, 4.55; N, 7.03%. Found: C, 48.07; H, 4.58; N, 6.86%. EIMS (m/z): 199 ($M^+$, 26%), 181 ($M^+$—$H_2O$, 7%), 155 ($M^+$—$(CH_3)_2N$, base): $^1$HNMR (DMSO-$d_6$) delta, 8.09 (1H, d, J=1.8 Hz), 7.74 (1H, d, J=1.8 Hz), 2.98 (6H, d, J=13.0 Hz); ir (potassium bromide): 3388, 1706, 1594, 1250, 1186 cm$^{-1}$.

EXAMPLE 8

Methyl 2-Formyl-4-thiophenecarboxylate

The title compound has been described by Gronowitz, S. et al., Arkiv. for Kemi. 21:265 (1963), and was prepared according to the following procedure. Methyliodide (1.32 g, 9.30 mmoles) was added to a stirred suspension of 2-formyl-4-thiophenecarboxylic acid (prepared according to Gronowitz, S., et al., Arkiv. for Kemi. 21:265 (1963)) (1.21 g, 7.75 mmoles) and sodium carbonate (2.87 g, 27.12 mmoles) in 40 ml of N,N-dimethylformamide. After stirring overnight at room temperature the mixture was poured into water (200 ml), saturated with solid sodium chloride and extracted with ethyl acetate. The combined extracts were washed with brine, dried (magnesium sulfate) and concentrated in vacuo to a light yellow solid (1.20 g, 91%), m.p. 110–112° C. EIMS (m/z): 170 ($M^+$, 84%), 139 ($M^+$—$CH_3O$, base), 111 ($M^+$—$CH_3O_2C$, 29%); $^1$HNMR ($CDCl_3$) delta, 9.90 (1H, d, 1.5 Hz), 8.41 (1H, s), 8.13 (1H, d, J=1.5 Hz), 3.88 (3H, s).

EXAMPLE 9

4-Methoxycarbonyl-2-thiophenecarboxylic acid

A stirred solution of methyl 2-formyl-4-thiophenecarboxylate (823 mg, 4.84 mmoles) in 50 ml of acetone was treated dropwise with Jones' reagent (5 ml). Once addition was complete the mixture was stirred at room temperature for 30 minutes, the excess oxidant was decomposed with isopropanol and the mixture filtered through diatomaceous earth. The acetone was removed in vacuo, the residue dissolved in ethyl acetate (30 ml) and the solution dried over magnesium sulfate. Concentration in vacuo furnished an off-white solid (880 mg, 98%). An analytical sample was obtained by trituration with a small amount of ethyl acetate, m.p. 141–3° C.

Analysis: Calculated for $C_7H_6O_4S$: C, 45.15; H, 3.25%. Found: C, 45.09; H, 3.14%. EIMS (m/z): 186 ($M^+$, 42%), 155 ($M^+$—$CH_3O$, base); $^1HNMR$ (DMSO-$d_6$) delta, 8.59 (1H, d, J=1.2 Hz), 7.91 (1H, d, J=1.2 Hz), 3.81 (3H, s); ir (potassium bromide): 3419, 1706, 1681 $cm^{-1}$.

EXAMPLE 10

Methyl 5-Formyl-2-thiophenecarboxylate

The title compound has been described by Gronowitz, S., et al., Arkiv. for Kemi. 21:265 (1963), and was prepared according to the following procedure. Methyliodide (4.36 g, 30.74 mmoles) was added to a stirred suspension of 5-formyl-2-thiophenecarboxylic acid (prepared according to Carpenter, A. J., et al., Tetrahedron 41:3808 (1985)) (4.00 g, 25.61 mmoles) and sodium carbonate (9.50 g, 89.65 mmoles) in 75 ml of N,N-dimethylformamide. After stirring overnight at room temperature the mixture was poured into water (350 ml), saturated with solid sodium chloride and extracted with ethyl acetate. The combined extracts were washed with brine, dried (magnesium sulfate) and concentrated in vacuo to a gray solid (3.83 g, 88%), m.p. 85–87° C. EIMS (m/z): 170 ($M^+$, 95%), 139 ($M^+$—$CH_3O$, base), 111 ($M^+$—$CH_3O_2C$, 64%); $^1HNMR$ (DMSO-$d_6$) delta, 9.94 (1H, s), 7.81 (1H, d, J=3.9 Hz), 7.71 (1H, d, J=3.9 Hz), 3.91 (3H, s).

EXAMPLE 11

5-Methoxycarbonyl-2-thiophenecarboxylic acid

The title compound has been described by Benkeser, R. A., et al., J.O.C. 38, 3660 (1973) and in British Patent 705950, and was prepared according to the following procedure. A stirred solution of methyl 5-formyl-2-thiophenecarboxylate (2.00 g, 11.75 mmoles) in 100 ml of acetone was treated dropwise with Jones' reagent (9 ml). Once addition was complete the mixture was stirred at room temperature for 1 hour, the excess oxidant decomposed with isopropanol and the mixture filtered through diatomaceous earth. The acetone was removed in vacuo, the residue dissolved in ethyl acetate (75 ml) and the solution dried over magnesium sulfate. Filtration and concentration furnished a yellow solid (1.60 g, 73%). An analytical sample was obtained by trituration with warm ethyl acetate, m.p. 186–189° C.

Analysis: Calculated for $C_7H_6O_4S$: C, 45.15; H, 3.25%. Found: C, 45.12%; H, 3.09%. EIMS (m/z): 186 ($M^+$, 70%), 169 ($M^+$—OH, 7%), 155 ($M^+$—$CH_3O$, base); $^1HNMR$ (DMSO-$d_6$) delta, 7.78 (1H, d, J=4.0 Hz), 7.72 (1H, d, J=4.0 Hz), 3.85 (3H, s); ir (potassium bromide): 3416, 1712, 1666, 1258 $cm^{-1}$.

EXAMPLE 12

5-Methoxycarbonyl-2-thiophenecarboxylic acid hydrazide

A stirred suspension of 5-methoxycarbonyl-2-thiophenecarboxylic acid (1.86 g, 10.0 mmoles) in 20 ml of thionyl chloride was refluxed for two hours. The solution was cooled to room temperature and concentrated in vacuo to an almost colorless oil which crystallized under vacuum. This solid was then dissolved in 25 ml of chloroform and added dropwise to a cooled (5° C.) solution of anhydrous hydrazine (800 mg, 25.0 mmoles) in 25 ml of chloroform under argon. Once addition was complete the mixture was stirred at room temperature for one hour and then evaporated to dryness in vacuo. The residual solid was suspended in 25 ml of water, stirred for fifteen minutes and filtered to furnish an off-white solid (1.79 g, 90%). An analytical sample was prepared by recrystallization from ethanol, m.p. 198–200° C.

Analysis: Calculated for $C_7H_8N_2O_3S$: C, 41.99; H, 4.03; N, 13.99%. Found: C, 41.88; H, 3.91; N, 13.86%. EIMS (m/z): 200 ($M^+$, 26%), 169 ($M^+$—$CH_3O$ or $N_2H_3$, base); $^1HNMR$ (DMSO-$d_6$) delta, 10.05 (1H, br s), 7.77 (1H, d, J=3.9 Hz), 7.71 (1H, d, J=3.9 Hz), 4.56 (2H, br s), 3.82 (3H, s); ir (potassium bromide): 3319, 3285, 1723, 1618, 1264, 746 $cm^{-1}$.

EXAMPLE 13

Methyl 5-(5-Methyl-1,3,4-oxadiazol-2-yl)-2-thiophenecarboxylate

A stirred suspension of 5-methoxycarbonyl-2-thiophenecarboxylic acid hydrazide (548 mg, 2.74 mmoles) and ethyl acetimidate hydrochloride (372 mg, 3.01 mmoles) in 10 ml of pyridine was refluxed for four hours, cooled to room temperature and evaporated in vacuo. The residual oily solid was dissolved in ethyl acetate and washed with water, 1N hydrochloric acid and 5% sodium bicarbonate. The ethyl acetate was dried (magnesium sulfate) and evaporated in vacuo to a pale tan solid (242 mg, 39%), m.p. 142–5° C. This material was used directly without further purification. Exact Mass: 224.0253, Calculated: 224.0256; EIMS (m/z): 224 ($M^+$, base), 193 ($M^+$—$CH_3O$, 33%), 169 ($C_7H_5O_3S$, 83%); $^1HNMR$ (DMSO-$d_6$) delta, 7.88 (1H, d, J=3.9 Hz), 7.80 (1H, d, J=3.9 Hz), 3.87 (3H, s), 2.58 (3H, s); ir (potassium bromide): 1705, 1571, 1291, 1101, 751 $cm^{-1}$.

EXAMPLE 14

5-(5-Methyl-1,3,4-oxadiazol-2-yl)-2-thiophenecarboxylic acid

A mixture of methyl 5-(5-methyl-1,3,4-oxadiazol-2-yl)-2-thiophenecarboxylate (100 mg, 0.45 mmoles) in 3 ml of 2N sodium hydroxide was diluted with 1 ml of methanol and stirred at room temperature for 2 hours. The solution was filtered to remove some trace insolubles and acidified to pH 3 with concentrated hydrochloric acid. The precipitate was collected and air dried to furnish a pale yellow solid (67 mg, 71%), m.p. 281–4° C.

Analysis: Calculated for $C_8H_6N_2O_3S$: C, 45.70; H, 2.88; N, 13.33%. Found: C, 45.81; H, 2.81; N, 13.26%. EIMS (m/z): 210 ($M^+$, base), 193 ($M^+$—OH, 3%), 168 (unknown, 8%), 155 ($C_6H_3O_3S$, 56%); $^1HNMR$ (DMSO-$d_6$) delta, 7.79 (1H, d, J=3.9 Hz), 7.77 (1H, d, J=3.9 Hz), 2.57 (3H, s); ir (potassium bromide): 3443, 1693, 1599, 1574, 1264, 744 $cm^{-1}$.

EXAMPLE 15

Methyl 4-acetyl-2-thiophenecarboxylate

Methyliodide (783 mg, 5.51 mmoles) was added to a stirred suspension of 4-acetyl-2-thiophenecarboxylic acid (prepared according to Satonaka, H., Bull. Chem. Soc. Japan 56:2463 (1983)) (782 mg, 4.59 mmoles) and sodium carbonate (1.70 g, 16.08 mmoles) in 25 ml of N,N-dimethylformamide. After stirring overnight at room temperature the mixture was poured into water (125 ml), saturated with solid sodium chloride and extracted with ethyl acetate (3×50 ml). The combined extracts were washed with brine, dried (magnesium sulfate) and concentrated in vacuo to an off-white solid (761 mg, 90%), m.p. 94–6° C. EIMS (m/z): 184 ($M^+$, 74%), 169 ($M^+$—$CH_3$, base), 153 ($M^+$—$CH_3O$, 51%); $^1$HNMR (DMSO-$d_6$) delta, 8.17 (1H, d, J=1.5 Hz), 8.13 (1H, d, J=1.5 Hz), 3.88 (3H, s), 2.51 (3H, s).

EXAMPLE 16

Methyl 4-Bromoacetyl-2-thiophenecarboxylate

Following the procedure of Japan Kokai Tokkyo Koho JP 60 11,487 CA 103:22580m (1985), a solution of bromine (4.29 g, 26.87 mmoles) in 40 ml of chloroform was added dropwise to a stirred solution of methyl 4-acetyl-2-thiophenecarboxylate, prepared according to Example 15 (4.95 g, 26.87 mmoles) in 150 ml of chloroform containing four drops of 50% (v/v) 48% hydrobromic acid/glacial acetic acid. After 10 minutes at 40° C. the solution was cooled to room temperature, concentrated in vacuo and the residue triturated with methanol (25 ml). Filtration furnished an off-white solid (4.96 g, 63%), m.p. 112–4° C. EIMS (m/z): 264/262 ($M^+$, 11%), 233/231 ($M^+$—$CH_3O$, 11%), 171/169 ($M^+$—$CH_2Br$, base); $^1$HNMR ($CDCl_3$) delta, 8.31 (1H, d, J=1.5 Hz), 8.17 (1H, d, J=1.5 Hz), 4.29 (2H, s), 3.90 (3H, s).

EXAMPLE 17

Methyl 4-(2-methylthiazol-4-yl)-2-thiophenecarboxylate monohydrobromide

A solution of methyl 4-bromoacetyl-2-thiophenecarboxylate, prepared according to Example 16, (398 mg, 1.51 mmoles) and thioacetamide (125 mg, 1.66 mmoles) in 15 ml of acetone was refluxed for 2 hours. The mixture was cooled to room temperature, filtered and the residue dried in vacuo to yield a white solid (375 mg, 77%), m.p. 224–5° C.

Analysis: Calculated for $C_{10}H_9NO_2S_2 \cdot HBr$: C, 37.50; H, 3.15; N, 4.36%. Found: C, 37.53; H, 3.09; N, 4.28%. EIMS (m/z): 239 ($M^+$, base), 208 ($M^+$—$CH_3O$, 65%), 198 ($M^+$—$C_2H_3N$, 76%); $^1$HNMR (DMSO-$d_6$) delta, 8.25 (1H, d, J=1.5 Hz), 8.22 (1H, d, J=1.5 Hz), 7.98 (1H, s), 5.98 (exchangeable), 3.82 (3H, s), 2.68 (3H, s); ir (potassium bromide): 3091, 1703, 1285 $cm^{-1}$.

EXAMPLE 18

4-(2-Methylthiazol-4-yl)-2-thiophenecarboxylic acid

A mixture of methyl 4-(2-methylthiazol-4-yl)-2-thiophenecarboxylate monohydrobromide, prepared according to Example 17, (3.20 g, 10.0 mmoles) in 50 ml of 2N sodium hydroxide was diluted with 15 ml of methanol and refluxed for 1 hour. The methanol was removed in vacuo and the residual aqueous solution was acidified to pH 3 with concentrated hydrochloric acid. The mixture was extracted with ethyl acetate (3×50 ml) and the dried (magnesium sulfate) extracts were concentrated to a white solid (2.12 g, 94%). An analytical sample was obtained by trituration with warm ethyl acetate, m.p. 195–7° C.

Analysis: Calculated for $C_9H_7NO_2S_2$: C, 47.98; H, 3.13; N, 6.22%. Found: C, 47.84; H, 3.01; N, 6.14%. EIMS (m/z): 225 ($M^+$, base), 208 ($M^+$—OH, 1%), 184 ($M^+$—$C_2H_3N$, 90%); ir (potassium bromide): 3103, 1676, 1284 $cm^{-1}$.

EXAMPLE 19

Methyl 5-formyl-2-thiophenecarboxylate oxime

A solution of methyl 5-formyl-2-thiophenecarboxylate, prepared according to Example 10, (6.26 g, 36.78 mmoles), hydroxylamine hydrochloride (3.07 g, 44.14 mmoles) and pyridine (3.49 g, 44.14 imoles) in 200 ml of ethanol was refluxed for 2 hours. The ethanol was removed in vacuo, the residue dissolved in ether and washed with water. The organic layer was dried (magnesium sulfate) and evaporated to a yellow solid. Trituration with a small amount of ether furnished the title compound as a white solid (4.93 g, 72%), m.p. 164–7° C. Oxime Z:E ratio:(82:18).

Analysis: Calculated for $C_7H_7NO_3S$: C, 45.39; H, 3.81; N, 7.56%. Found: C, 45.41; H, 3.69; N,7.48%. EIMS (m/z): 185 ($M^+$, 97%), 154 ($M^+$—$CH_3O$, base); $^1$HNMR (DMSO-$d_6$) delta, Z isomer:12.52 (1H, br s), 7.99 (1H, s), 7.77 (1H; d, J=4.0 Hz), 7.50 (1H, d, J=4.0 Hz), 3.83 (3H, s); E isomer:11.66 (1H, br s), 8.38 (1H, s), 7.74 (1H, d, J=4.0 Hz), 7.34 (1H, d, J=4.0 Hz), 3.82 (3H, s); ir (potassium bromide): 3400, 1649, 918 $cm^{-1}$.

EXAMPLE 20

Methyl 5-cyano-2-thiophenecarboxylate

The title compound has been described by Decroix, B., et al., J. Chem. Res. (M), 1848 (1978), and was prepared according to the following procedure. A stirred mixture of methyl 5-formyl-2-thiophenecarboxylate oxime, prepared according to Example 19, (4.87 g, 26.29 mmoles) was refluxed overnight in 60 ml of acetic anhydride. The solution was cooled to room temperature, poured into 400 ml of water and shaken vigorously. The mixture was extracted with ether (3×100 ml) and the extracts were backwashed with 10% potassium hydroxide (3×50 ml). The combined organic layers were dried (magnesium sulfate) and concentrated to an off-white solid (3.50 g, 80%), m.p. 76–8° C. EIMS (m/z) 167 ($M^+$, 34%) and 136 ($M^+$—$CH_3O$, base); $^1$HNMR (DMSO-$d_6$) delta, 8.03 (1H, d, J=4.2 Hz), 7.88 (1H, d, J=4.2 Hz), 3.87 (3H, s); ir (potassium bromide): 2228, 1726 $cm^{-1}$.

EXAMPLE 21

Methyl 5-(N-hydroxy)carboximidamido-2-thiophenecarboxylate

A stirred mixture of methyl 5-cyano-2-thiophenecarboxylate, prepared according to Example 20, (901 mg, 5.39 mmoles), hydroxylamine hydrochloride (412 mg, 5.93 mmoles) and sodium acetate (553 mg, 6.74 mmoles) in 25 ml of 5:1 ethanol-water was refluxed for 45 minutes. The ethanol was removed in vacuo and the crystalline residue was collected by filtration. Additional material was isolated from the chilled filtrate to ultimately yield 932 mg (86%) of pale yellow crystalline solid, m.p. 144–6° C.

Analysis: Calculated for $C_7H_8N_2O_3S$: C, 41.99; H, 4.03; N, 13.99%. Found: C, 42.24; H, 3.91; N, 13.59%. EIMS (m/z): 200 ($M^+$, base), 185 ($M^+$—$CH_3$, 83%), 169 ($M^+$—$CH_3O$, 60%); $^1$HNMR (DMSO-$d_6$) delta, 9.97 (1H, s), 7.72 (1H, d, J=4.0 Hz), 7.51 (1H, d, J=4.0 Hz), 6.11 (2H, br s), 3.80 (3H, s); ir (potassium bromide) 3491, 1725 and 1636 $cm^{-1}$.

EXAMPLE 22

Methyl 5-(5-methyl-1,2,4-oxadiazol-3-yl)-2-thiophenecarboxylate

A stirred mixture of methyl 5-(N-hydroxy) carboximidamido-2-thiophenecarboxylate, prepared according to Example 21, (734 mg, 3.67 mmoles) and acetic anhydride (1.12 g, 11.0 mmoles) in 25 ml of toluene was refluxed for 24 hours. The solvent was removed in vacuo and the residue triturated with a small portion of toluene to furnish an off-white solid (547 mg, 67%), m.p. 134–6° C. EIMS (m/z): 224 ($M^+$, 99%), 193 ($M^+$—$CH_3O$, base), 183 ($M^-$—$C_2H_3N$, 58%), 152 ($C_6H_2NO_2S$, 89%); $^1$HNMR (DMSO-$d_6$) delta, 7.77 (1H, d, J=4.0 Hz), 7.69 (1H, d, J=4.0 Hz), 3.89 (3H), 2.64 (3H, s); ir (potassium bromide): 1720, 1597 and 887 $cm^{-1}$. This material was used directly without further purification.

EXAMPLE 23

5-(5-methyl-1,2,4-oxadiazol-3-yl)-2-thiophenecarboxylic acid

A mixture of methyl 5-(5-methyl-1,2,4-oxadiazol-3-yl)-2-thiophenecarboxylate, prepared according to Example 22, (86 mg, 0.38 mmoles) in 3 ml of 2N sodium hydroxide was diluted with 1 ml of methanol and warmed to 60° C. for 10 minutes. The solution was cooled to room temperature, diluted with 2 ml of water and acidified to pH 2 with concentrated hydrochloric acid. After standing for 30 minutes the fluffy crystalline solid which slowly separated was collected by filtration and dried in vacuo to furnish the title compound (45 mg, 56%), m.p. 218–20° C.

Analysis: Calculated for $C_8H_6N_2O_3S$: C, 45.70; H, 2.88; N, 13.33%. Found: C, 45.69; H, 2.81; N, 13.06%. EIMS (m/z): 210 ($M^+$, 89%), 169 ($M^+$—$C_2H_3N$, base), 152 ($C_6H_2NO_2S$, 27%); $^1$HNMR (DMSO-$d_6$) delta, 7.77 (2H, 8), 2.65 (3H, s); ir (potassium bromide): 3429, 1668 and 889 $cm^{-1}$.

EXAMPLE 24

Methyl 5-(5-trifluoromethyl-1,2,4-oxadiazol-3-yl)-2-thiophenecarboxylate

A stirred mixture of methyl 5-(N-hydroxy) carboximidamido-2-thiophenecarboxylate, prepared according to Example 21, (833 mg, 4.16 mmoles) and trifluoroacetic anhydride (2.62 g, 12.48 mmoles) in 25 ml of toluene was refluxed for one hour. The solvent was evaporated in vacuo, the residue triturated with a small portion of toluene and filtered to furnish a white crystalline solid (400 mg, 35%), m.p. 126–7° C. The product was used directly without further purification. Exact Mass: 277.9998; Calculated: 277.9974; EIMS (m/z): 278 ($M^+$, 67%), 247 ($M^+$—$CH_3O$, base), 152 ($C_6H_2NO_2S$, 41%); $^1$HNMR ($CDCl_3$) delta, 7.81 (2H, s), 3.91 (3H, s); ir (potassium bromide): 1712, 1255, 912 $cm^{-1}$.

EXAMPLE 25

5-(5-Trifluoromethyl-1,2,4-oxadiazol-3-yl)-2-thiophenecarboxylic acid

A mixture of methyl 5-(5-trifluoromethyl-1,2,4-oxadiazol-3-yl)2-thiophenecarboxylate, prepared according to Example 24, (100 mg, 0.36 mmoles) in 3 ml of 2N sodium hydroxide was diluted with 1 ml of methanol and warmed to 50° C. for ten minutes. The solution was cooled to room temperature, diluted with 3 ml of water and acidified to pH 2 with concentrated hydrochloric acid. After standing for one hour the off-white crystalline solid (41 mg, 43%) was collected by filtration and dried in vacuo, m.p. 175–7° C.

Analysis: Calculated for $C_8H_3F_3N_2O_3S$: C, 36.37; H, 1.14; N, 10.61%. Found: 36.65; H, 1.18; N, 10.24%. EIMS (m/z): 264 ($M^+$, base), 247 ($M^+$—OH, 43%), 169 ($M^+$—$C_2F_3N$, 24%); $^1$HNMR (DMSO-$d_6$) delta, 7.94 (1H, d, J=4.0 Hz), 7.83 (1H, d, J=4.0 Hz); ir (potassium bromide); 3430 br, 1661, 1208, 847 $cm^{-1}$.

EXAMPLE 26

Methyl 4-(thiazol-4-yl)2-thiophenecarboxylate hydrobromide

A solution of methyl 4-(bromoacetyl)-2-thiophenecarboxylate, prepared according to Example 16, (1.25 g, 4.75 mmoles) and thioformamide (436 mg, 7.13 mmoles) in 35 ml of acetone was refluxed for one hour. The mixture was cooled slightly and filtered to furnish a yellow solid (941 mg, 65%). The analytical sample was recrystallized from ethanol, m.p. 201–2° C.

Analysis: Calculated for $C_9H_7NO_2S_2$.HBr: C, 35.30; H, 2.63; N, 4.58%. Found C, 35.31; H, 2.60; N, 4.48%. EIMS (m/z): 225 ($M^+$, base), 194 ($M^+$—$CH_3O$, 92%), 167 ($C_8H_7O_2S$, 25%); $^1$HNMR (DMSO-$d_6$) delta, 9.18 (1H, d, J=1.7 Hz), 8.31 (1H, d, J=1.2 Hz), 8.30 (1H, d, J=1.2 Hz), 8.21 (1H, d, J=1.7 Hz), 4.50 (1H, exchangeable), 3.85 (3H, s); ir (potassium bromide): 3054, 1711, 1272, 778 $cm^{-1}$.

EXAMPLE 27

4-(Thiazol-4-yl)-2-thiophenecarboxylic acid

A mixture of methyl 4-(thiazol-4-yl)-2-thiophenecarboxylate hydrobromide, prepared according to Example 26, (500 mg, 1.63 mmoles) in 8 ml of 2N sodium hydroxide was diluted with 1 ml of methanol and refluxed for thirty minutes. The methanol was removed in vacuo and the residual aqueous solution was acidified to pH 2 with concentrated hydrochloric acid. The mixture was extracted with ethyl acetate and the dried (magnesium sulfate) extracts were concentrated to a pale yellow solid (318 mg, 92%), m.p. 183–5° C.

Analysis: Calculated for $C_8H_5NO_2S_2$: C, 45.48; H 2.39; N, 6.63%. Found: C, 45.42; H, 2.29; N, 6.46%. EIMS (m/z): 211 ($M^+$, base), 194 ($M^+$—OH, 23%) and 184 ($C_7H_4O_2S_2$, 80%); $^1$HNMR (DMSO-$d_6$)delta, 9.16 (1H, d, J=1.2 Hz), 8.23 (2H, br s), 8.16 (1H, d, J=1.2 Hz); ir (potassium bromide): 3440 br, 3110, 1691, 1285 $cm^{-1}$.

EXAMPLE 28

4-Methylthio-2-thiophenecarboxylic acid

Lithium diisopropylamide was prepared by slowly adding 31.0 ml (77.5 mmoles) 2.5M n-butyllithium in hexanes to a cooled (2-propanol/dry ice) tetrahydrofuran (200 ml) solution of diisopropylamine (11.0 ml, 78.5 mmoles) with the reaction temperature maintained below –60° C. After 15 minutes the reaction solution was warmed to room temperature for 30 minutes and then cooled to below –70° C. again. A 100 ml tetrahydrofuran solution of 9.9 g (76.0 mmoles) of 3-methylthiothiophene (prepared according to Henrio, G., et al., Tetrahedron 33, 191 (1977)) was added slowly with the reaction temperature controlled below –70° C. After complete addition the reaction was stirred for 15 minutes and then excess carbon dioxide was bubbled through the solution. The solution was then warmed to 10° C. and quenched with 100 ml of water. After stirring for a few minutes the reaction mixture was poured into a separatory funnel and extracted with a 500 ml portion of diethyl ether. The organic layer was extracted with 100 ml of 1N sodium hydroxide; both basic aqueous solutions were then combined, washed with 100 ml of diethyl ether and acidified with concentrated hydrochloric acid. The acidic aqueous mixture was then extracted with diethyl ether (2×250 ml). The ether solution was washed with brine, dried over magnesium sulfate, filtered and concentrated in vacuo to 11.75 g (67.4 mmoles) of yellow solid which NMR showed to be a 3:2 mixture of isomers (4- vs. 3-) of desired thiophenecarboxylic acid. This crude product was stirred in a 50 ml portion of diethyl ether for thirty minutes, then filtered, and the filtrate concentrated in vacuo to 8.68 g (49.8 mmoles) of solid which contained greater than 80% (estimated by NMR) of the desired 4-methylthio-2-thiophenecarboxylic acid. Recrystallization from chloroform afforded 4.11 g (23.6 mmoles) of pale yellow solid, m.p. 118–120° C. (lit. m.p. 123–124° C.), which was 95% 4-methylthio-2-thiophenecarboxylic acid (purity estimated by NMR). Total yield was 31%.

EXAMPLE 29

5-(N,N-Dimethylaminosulfonyl)-2-thiophenecarboxylic acid

Lithium diisopropylamide was prepared by slowly adding 10.5 ml (26.3 mmoles) of 2.5M n-butyllithium in hexanes to a cooled (2-propanol/dry ice) tetrahydrofuran (200 ml) solution of diisopropylamine (5.0 ml, 35.7 mmoles) with the reaction temperature maintained below −60° C. After 5 minutes the reaction solution was warmed to room temperature for 30 minutes and then cooled to below −70° C. again. A 100 ml tetrahydrofuran solution of 3.4 g (17.8 mmoles) of 2-(N,N-dimethylaminosulfonyl) thiophene (prepared according to Slocum, D. W., et al., JOC 38, 4189 (1973)) was added slowly with the reaction temperature controlled below −70° C. After complete addition the reaction was stirred for 30 minutes and then excess carbon dioxide was bubbled through the solution. The solution was then warmed to 0° C. and quenched with 50 ml of 1N sodium hydroxide. A 300 ml portion of diethyl ether was added to the aqueous tetrahydrofuran solution and the phases were separated in a separatory funnel. The organic layer was extracted with 50 ml of 1N sodium hydroxide. Both basic aqueous solutions were combined, washed with 50 ml of diethyl ether and acidified with concentrated hydrochloric acid. The acidic aqueous mixture was extracted with diethyl ether (2×100 ml). The ether solution was washed with brine, dried over magnesium sulfate, filtered and concentrated in vacuo to 3.66 g (15.6 mmoles) of desired thiophenecarboxylic acid as a colorless solid, m.p. 184–186° C. (lit. m.p.=170–172° C.). Total yield was 87%.

EXAMPLE 30

5-Aminosulfonyl-2-thiophenecarboxylic Acid

Lithium diisopropylamide was prepared by slowly adding 26.5 ml (66.3 mmoles) of 2.5M n-butyllithium in hexanes to a cooled (2-propanol/dry ice) tetrahydrofuran (200 ml) solution of diisopropylamine (11.0 ml, 78.5 mmoles) with the reaction temperature maintained below −60° C. After 5 minutes the reaction solution was warmed to room temperature for 30 minutes and then cooled to below −70° C. again. A 100 ml tetrahydrofuran solution of 3.26 g (20.0 mmoles) of 2-aminosulfonylthiophene (prepared according to Slocum, D. W., et al., JOC 38, 4189 (1973)) was added slowly with the reaction temperature controlled below −70° C. After complete addition the reaction was stirred for 30 minutes and then excess carbon dioxide was bubbled through the solution. The solution was then warmed to 2° C. and quenched with 50 ml of 1N sodium hydroxide. A 300 ml portion of diethyl ether was added to the aqueous tetrahydrofuran solution and the phases were separated in a separatory funnel. The organic layer was extracted with 50 ml of 1N sodium hydroxide. Both basic aqueous solutions were combined, washed with 50 ml of diethyl ether and acidified with concentrated hydrochloric acid. The acidic aqueous mixture was extracted with diethyl ether (2×100 ml). The ether solution was washed with brine, dried over magnesium sulfate, filtered and concentrated in vacuo to 2.56 g (12.4 mmoles) of desired thiophenecarboxylic acid as a colorless solid. Recrystallization from water afforded 1.79 g (8.6 mmoles) of tan solid, m.p. 228–231° C. (lit. m.p. 231–232° C.). Total yield was 43%.

EXAMPLE 31

5-Chloro-3-(3-chloro-2-thenoyl)-2-oxindole-1-carboxamide

Excess thionyl chloride (3.5 ml, 48.0 mmoles) was added to 0.85 g (5.2 mmoles) of 3-Chloro-2-thiophenecarboxylic acid (prepared according to Corral, C., et al., Heterocycles 23:1431 (1985)) dissolved in 50 ml of toluene and stirring at room temperature. After addition the solution was refluxed for 3 hours to form 3-chloro-2-thiophenecarbonyl chloride. Concentration of the reaction solution gave the acid chloride as a white solid. The acid chloride was then dissolved in 4 ml of N,N-dimethylformamide and slowly added to a cooled (ice/water bath) stirring solution of 5-chloro-2-oxindole-1-carboxamide (1.0 g, 4.71 mmoles) and 4-(N,N-dimethylamino)pyridine (1.3 g, 10.5 mmoles) in 10 ml of N,N-dimethylformamide. After 45 minutes the solution was allowed to warm to room temperature and after 2 hours was worked-up by pouring into a mixed ice/6 N hydrochloric acid solution. A yellow precipitate formed. The precipitate was filtered, washed with water and dried to give 1.3 g of impure product as a yellow solid. Recrystallization with acetic acid/heptane (2:1) gave 0.77 g (2.2 mmoles) of pure title compound as yellow needles, m.p. 222–224° C. Total yield of product was 42%.

Analysis: Calculated for $C_{14}H_8Cl_2N_2O_3S$: C, 47.34; H, 2.27; N, 7.89%. Found: C, 47.59; H, 2.20; N, 7.92%. EIMS (m/z): 354/356/358 ($M^+$, 12%), 311/313/315 ($M^+$—CHNO, 31%), 276/278 ($M^+$—CHClNO, 14%), 193/195 ($M^+$—CHNO-$C_4H_3ClS$, base), 145/147 ($C_5H_2ClOS$, 34%). $^1$HNMR (DMSO-$d_6$) delta, 8.18 (1H, br s, exchangeable), 8.11 (1H, d, J=8.5 Hz), 7.91 (1H, d, J=5.3 Hz), 7.80 (1H, d, J=2 Hz), 7.60 (1H, br s, exchangeable), 7.23 (1H, dd, J=8.5 Hz, 2 Hz) and 7.19 (1H, d, J=5.3 Hz). $^{13}$CNMR (DMSO-$d_6$) delta, 167.1, 161.2, 152.5, 134.7, 129.4, 129.3, 127.8, 127.7, 125.7, 125.1, 124.0, 121.2, 116.1 and 104.1. ir (potassium bromide): 3386, 1732, 1618, 1575, 1375, 1274 and 1196 $cm^{-1}$.

EXAMPLE 32

5-Chloro-3-(4-chloro-2-thenoyl)-2-oxindole-1-carboxamide 1.63 g (10.0 mmoles) of 4-chloro-2-thiophenecarboxylic acid (prepared according to Iriarte, J., et al., J. Het. Chem. 13:393 (1976)) was dissolved in 10 ml of thionyl chloride and heated to reflux. After refluxing for 1.5 hours excess thionyl chloride was evaporated, leaving 1.88 g of crude 4-chloro-2-thiophenecarbonyl chloride as a dark brown oil. This acid chloride was dissolved in 10 ml of N,N-dimethylformamide and slowly added to a cooled (ice-water) 40 ml N,N-dimethylformamide solution of 1.75 g (8.33 mmoles) 5-chloro-2-oxindole-1-carboxamide and 3.05 g (25.0 mmoles) of 4-(N,N-dimethylamino)pyridine. The reaction was complete in 1 hour. The mixture was poured into 100 ml of 1N hydrochloric acid causing a precipitate to form. The crude solid was filtered, dried and recrystallized to give 1.89 g (5.3 mmoles, 64% yield) of title compound as yellow needles, m.p. 212–214° C. (2-butanone).

Analysis: Calculated for $C_{14}H_8Cl_2N_2O_3S$: C, 47.34; H, 2.27; N, 7.89%. Found: 47.08; H, 2.22; N, 7.81%. EIMS (m/z): 354/356/358 (M$^+$, 5%), 311/313/315 (M$^+$—CONH, 25%), 193/195 (M$^+$—CONH, $C_4H_3ClS$, base) and 145/147 ($C_5H_2ClOS$). $^1$HNMR (DMSO-d$_6$) delta, 8.38 (1H, d, J=1 Hz), 8.06 (1H, br s), 8.05 (1H, d, J=8.5 Hz), 7.75 (1H, br s), 6.97 (1H, br d, J=8.5 Hz) and 5.94 (1H, br s, exchangeable). ir (potassium bromide): 3380, 3220 br, 1741, 1620, 1540, 1575, 1375, 1270, 1195 and 1180 cm$^{-1}$.

EXAMPLE 33

5-Chloro-3-(5-chloro-2-thenoyl)-2-oxindole-1-carboxamide

A 2.44 g (15.0 mmoles) commercial sample of 5-chloro-2-thiophenecarboxylic acid and 10 ml of thionyl chloride were reacted according to the procedure of Example 32. The crude yield of 5-chloro-2-thiophenecarbonyl chloride was 2.64 g as an oily solid. This material was then coupled to 2.42 g (11.5 mmoles) of 5-chloro-2-oxindole-1-carboxamide in the presence of 3.52 g (28.8 mmoles) 4-(N,N-dimethylamino)pyridine as in Example 32. Workup gave 4.33 g of wet crude product. Drying and recrystallization gave 2.99 g (8.42 mmoles, 73% yield) of title compound as yellow crystalline material, m.p. 220–222° C. (2-butanone).

Analysis: Calculated for $C_{14}H_8Cl_2N_2O_3S$: C, 47.34; H, 2.27; N, 7.89%. Found: C, 47.32; H, 2.21; N, 7.80%. ACE/EIMS (m/z): 354/356/358 (M$^+$, 22%), 311/313/315 (M$^+$—CONH, 60%), 193/195 (M$^+$—CONH—$C_4H_3ClS$, base) and 145/147 ($C_5H_2ClOS$). $^1$HNMR (DMSO-d$_6$) delta, 8.31 (1H, d, J=3.5 Hz), 8.05 (1H, br s), 8.01 (1H, d, J=8 Hz), 7.09 (1H, br d, J=3.5 Hz), 6.89 (1H, br d, J=8 Hz) and 4.86 (1H, br s, exchangeable). ir(potassium bromide): 3640, 1745, 1640, 1565, 1380, 1355, 1280 and 805 cm$^{-1}$.

EXAMPLE 34

5-Chloro-3-(3-bromo-2-thenoyl)-2-oxindole-1-carboxamide

Using the procedure of Example 31, 2.07 g (10.0 mmoles) of 3-bromo-2-thiophenecarboxylic acid (prepared according to Reinecke, M. G., et al., Synthesis, 327 (1980)) was reacted with 1.1 ml (15.0 mmoles) of thionyl chloride to give 2.27 g of crude acid chloride as a solid. A 10 ml N,N-dimethylformamide solution of 2.27 g (10.0 mmoles) of 3-bromo-2-thiophenecarbonyl chloride was reacted, according to Example 32, with 1.75 g (8.33 mmoles) of 5-chloro-2-oxindole-1-carboxamide in the presence of 3.05 g (25.0 mmoles) of 4-(N,N-dimethylamino)pyridine in 40 ml of N,N-dimethylformamide. Reaction workup gave 3.28 g of a dark orange solid. Recrystallization of this solid gave 1.63 g (4.08 mmoles, 41% yield) of the title compound as an orange crystalline solid, m.p. 216–217° C. (2-butanone).

Analysis: Calculated for $C_{14}H_8BrClN_2O_3S$: C, 42.08; H, 2.02; N, 7.01%. Found: C, 42.15; H, 2.05; N, 7.00%. ACE-EIMS (m/z): 398/400/402 (M$^+$, 8%), 355/357/359 (M$^+$—CHNO, 21%), 276/278 (M$^+$—CHNO—Br, 13%), 193/195 (M$^+$—CHNO—$C_4H_3BrS$, 89%) and 69 (unknown, base). $^1$HNMR (DMSO-d$_6$) keto form: delta, 8.25 (1H, br s, exchangeable), 8.10 (1H, d, J=8.5 Hz), 7.87 (1H, d, J=5 Hz), 7.81 (1H, br d, J=1.5 Hz), 7.54 (1H, br s, exchangeable), 7.21 (2H, m) and 5.70 (1H, br s, exchangeable); enol form: delta, 10.27 (1H, br s, exchangeable), 8.19 (1H, br s, exchangeable), 8.13 (1H, d, J=8.5 Hz), 7.91 (1H, d, J=5 Hz), 7.81 (1H, br d, J=1.5 Hz), 7.60 (1H, br s, exchangeable), 7.25 (1H, dd, J=8.5, 1.5 Hz) and 7.23 (1H, d, J=5 Hz); $^{13}$CNMR (DMSO-d$_6$) delta, 167.0, 162.2, 152.4, 134.6, 131.4, 130.2, 129.8, 127.6, 125.5, 124.9, 121.1, 116.0, 111.5 and 103.8; ir (potassium bromide): 3375, 3217 br, 1726, 1617, 1583, 1752, 1374, 1267 and 1196 cm$^{-1}$.

EXAMPLE 35

5-Chloro-3-(4-bromo-2-thenoyl)-2-oxindole-1-carboxamide

According to the procedure of Example 32, 2.48 g (12.0 mmoles) of 4-bromo-2-thiophenecarboxylic acid (prepared according to Lawesson, S. O., Arkiv. for Kemi. 11:317 (1957)) and 10 ml of thionyl chloride were combined and heated. The reaction gave 2.99 g of 4-bromo-2-thiophenecarbonyl chloride as a dark oil. Following the procedure of Example 32, the acid chloride, 2.11 g (10.0 mmoles) of 5-chloro-2-oxindole-1-carboxamide and 3.67 g (30.0 nmoles) of 4-(N,N-dimethylamino)pyridine were reacted in N,N-dimethylformamide to give 4.03 g of a crude orange solid. Recrystallization gave 2.67 g (6.68 mmoles, 66.8% yield) of title compound as a yellow crystalline solid, m.p. 217–219° C. (dec.) (2-butanone).

Analysis: Calculated for $C_{14}H_8BrClN_2O_3S$: C, 42.08; H, 2.02; N, 7.01%. Found: C, 42.07; H, 2.00; N, 7.04%. EIMS (m/z): 398/400/402 (M$^+$, 1%), 355/357/359 (M$^+$—CHNO, 8%), 193/195 (M$^+$—CHNO—$C_4H_3BrS$, base) and 189/191 ($C_5H_2BrOS$, 35%); $^1$HNMR (DMSO-d$_6$) delta, 8.41 (1H, d, J=1.6 Hz), 8.06 (1H, br d, J=1.2 Hz), 8.05 (1H, d, J=8.5 Hz), 7.86 (1H, br s), 6.98 (1H, dd, J=8.5, 1.2 Hz) and 6.05 (br s, exchangeable); ir (potassium bromide): 3384, 3228 br, 1741, 1620, 1588, 1573, 1375, 1269, 1193 and 1180 cm$^{-1}$.

EXAMPLE 36

5-Chloro-3-(5-bromo-2-thenoyl)-2-oxindole-1-carboxamide

Following the procedure of Example 32, 2.07 g (10.0 mmoles) of commercially available 5-bromo-2-thiophenecarboxylic acid was reacted with 10 ml of thionyl chloride to give 2.35 g of crude 5-bromo-2-thiophenecarbonyl chloride as a red oil. The total crude acid chloride was coupled to 1.76 g (8.33 mmoles) of 5-chloro-2-oxindole-1-carboxamide by the procedure in Example 32 using 3.05 g (25.0 mmoles) of 4-(N,N-dimethylamino) pyridine and 50 ml of N,N-dimethylformamide. Acidic workup gave a solid which was recrystallized to give 1.77 g (4.43 mmoles, 53% yield) of title compound as reddish-brown crystals, m.p. 228–229° C. (tetrahydrofuran).

Analysis: Calculated for $C_{14}H_8BrClN_2O_3S$: C, 42.08; H, 2.02; N, 7.01%. Found: C, 42.25; H, 1.97; N, 6.77%. ACE-EIMS (m/z): 397/399/401 (M$^+$, 5%), 354/356/358 (M$^+$—CHNO, 17%) and 193/195 (M$^+$—CONH—$C_4H_3BrS$, base); $^1$HNMR (DMSO-d$_6$) delta, 8.19 (1H, d, J=4 Hz), 8.08

(1H, d, J=8.5 Hz), 8.06 (1H, br s), 7.29 (1H, br d, J=4 Hz), 7.02 (1H, br d, J=8.5 Hz) and 6.24 (1H, br s, exchangeable); ir (potassium bromide): 3386, 3208 br, 1750, 1569, 1375, 1344, 1203 and 794 cm$^{-1}$.

EXAMPLE 37

5-Chloro-3-(5-iodo-2-thenoyl)-2-oxindole-1-carboxamide

Following the procedure of Example 32, 1.96 g (7.72 mmoles) of 5-iodo-2-thiophenecarboxylic acid (prepared as described in Example 3) was mixed with 10 ml of thionyl chloride and heated to reflux. Reaction led to 2.10 g of crude 5-iodo-2-thiophenecarbonyl chloride as a yellow solid. This yellow solid was dissolved in 10 ml of N,N-dimethylformamide and slowly added to a 40 ml N,N-dimethylformamide solution of 1.75 g (8.33 mmoles) of 5-chloro-2-oxindole-1-carboxamide and 3.05 g (25 mmoles) of 4-(N,N-dimethylamino)pyridine according to Example 32. Workup gave 3.18 g of impure product as an orange solid. Recrystallization in tetrahydrofuran gave 1.47 g (3.29 mmoles, 40% yield) of pure title compound as fine orange crystals, m.p. 230–232° C.

Analysis: Calculated for $C_{14}H_8ClIN_2O_3S$: C, 37.65; H, 1.81; N, 6.27%. Found: C, 37.93; H, 1.73; N, 6.13%. EIMS (m/z): 446/448 (M$^+$—CHNO, 13%), 237 ($C_5H_2IOS$, 39%) and 193/195 (M$^+$—CONH—$C_4H_3IS$, base); $^1$HNMR (DMSO-d$_6$) delta, 8.05 (1H, d, J=8.5 Hz), 8.00 (1H, br s), 7.92 (1H, d, J=4.0 Hz), 7.38 (1H, br d, J=4.0 Hz), 7.01 (1H, br d, J=8.5 Hz) and 5.37 (1H, br s, exchangeable); ir (potassium bromide): 3383 br, 3216 br, 1749, 1565 and 1373 cm$^{-1}$.

EXAMPLE 38

5-Chloro-3-(4,5-dibromo-2-thenoyl)-2-oxindole-1-carboxamide

Using the procedure of Example 32, 2.86 g (10.0 mmoles) of commercially available 4,5-dibromo-2-thiophenecarboxylic acid was added to 10 ml of thionyl chloride to give a heterogeneous mixture. Heating the reaction mixture helped the solution become homogenous. Concentration of the reaction solution gave 3.15 g of crude 4,5-dibromo-2-thiophenecarbonyl chloride as a brown oil. The crude acid chloride, dissolved in 10 ml of N,N-dimethylformamide was slowly added to 1.76 g (8.33 nmoles) of 5-chloro-2-oxindole-1-carboxamide and 3.05 g (25.0 mmoles) of 4-(N,N-dimethylamino)pyridine in 40 ml of N,N-dimethylformamide under the conditions of Example 32. Workup gave 2.82 g of orange solid which was recrystallized from 2-butanone to give 1.61 g (3.37 mmoles, 40% yield) of pure title compound as a yellow solid, m.p. 229–31° C.

Analysis: Calculated for $C_{14}H_7Br_2ClN_2O_3S$: C, 35.14; H, 1.47; N, 5.85%. Found: C, 35.34; H, 1.34; N, 5.66%. ACE/EIMS (m/z): 476/478/480/482 (M$^+$, 4%), 433/435/437/439 (M$^+$—CHNO, 23%), 267/269/271 ($C_5HBr_2OS$, 28%) and 193/195 (M$^+$—CONH—$C_4H_2Br_2S$, base); $^1$HNMR (DMSO-d$_6$) delta, 8.62 (1H, s), 8.14 (1H, br s), 8.05 (1H, d, J=8.5 Hz), 6.93 (1H, br d, J=8.5 Hz) and 6.86 (1H, br s, exchangeable); ir (potassium bromide): 3397, 3238 br, 1748, 1614, 1574, 1375, 1193 and 816 cm$^{-1}$.

EXAMPLE 39

5-Chloro-3-(4-methylthio-2-thenoyl)-2-oxindole-1-carboxamide

The title compound was prepared according to the procedure of Example 32. The reaction of 1.74 g (10.0 mmoles) of 4-methylthio-2-thiophenecarboxylic acid (prepared as described in Example 28) with 10 ml of thionyl chloride gave 2.02 g of 4-methylthio-2-thiophenecarbonyl chloride as a yellow solid. The acid chloride was coupled with 1.75 g (8.33 mmoles) of 5-chloro-2-oxindole-1-carboxamide in the presence of 3.05 g (25 mmoles) 4-(N,N-dimethylamino)pyridine as described in Example 32. Workup afforded 4.56 g of orange solid. Recrystallization of the crude orange solid gave 1.40 g (3.82 mmoles, 46%) of pure title compound as yellowish-orange solid, m.p. 216–19° C. (tetrahydrofuran).

Analysis: Calculated for $C_{15}H_{11}ClN_2O_3S_2$: C, 49.11; H, 3.02; N, 7.64%. Found: 49.06; H, 3.09; N, 7.53%. EIMS (m/z): 366/368 (M$^+$, 6%), 323/325 (M$^+$—CONH, 20%), 193/195 (M$^+$—CONH—$C_5H_6S_2$, 43%), 157 ($C_6H_5OS_2$, 66%) and 130 ($C_5H_6S_2$, base); $^1$HNMR (DMSO-d$_6$) delta, 8.09 (1H, d, J=8.5 Hz), 8.05 (1H, br s), 7.96 (1H, br s), 7.51 (1H, br s), 7.08 (1H, br d, J=8.5 Hz), 6.16 (1H, br s, exchangeable) and 2.52 (3H, s); ir (potassium bromide) 3387, 3220 br, 1741, 1616, 1588, 1376, 1195 and 1185 cm$^{-1}$.

EXAMPLE 40

5-chloro-3-(5-methylthio-2-thenoyl)-2-oxindole-1-carboxamide

The title compound was prepared according to the procedure of Example 32. A 1.74 g (10.0 mmoles) sample of 5-methylthio-2-thiophenecarboxylic acid (prepared according to Knight, D. W., et al., J. Chem. Soc. P.T.I, 791 (1983)) was converted to 1.93 g of the corresponding acid chloride by reaction with 10 ml of thionyl chloride. The acid chloride was directly reacted with 1.75 g (8.33 mmoles) of 5-chloro-2-oxindole-1-carboxamide in the presence of 3.05 g (25 mmoles) 4-(N,N-dimethylamino)pyridine as described in Example 32. Aqueous acid workup gave 3.02 g of an orange solid. Recrystallization of the impure orange solid from tetrahydrofuran furnished 1.31 g (3.57 mmole, 43% yield) of pure 5-chloro-3-(5-methylthio-2-thenoyl)-2-oxindole-1-carboxamide as an orange solid. Determination of the melting point showed that the material first melts at 180° C. then resolidified and then melts again at 247–250° C. (dec.)

Analysis: Calculated for $C_{15}H_{11}ClN_2O_3S_2$: C, 49.11; H, 3.02; N, 7.64%. Found: C, 48.92; H, 2.98; N, 7.52%. EIMS (m/z): 366/368 (M$^+$, 16%), 323/325 (M$^+$—CONH, 23%), 193/195 (M$^+$—CONH—$C_5H_6S_2$, 30%), 157 ($C_6H_5OS_2$, 83%) and 130 ($C_5H_6S_2$, base); $^1$HNMR (DMSO-d$_6$) delta, 8.11 (1H, d, J=3.9 Hz), 8.09 (1H, d, J=8.5 Hz), 7.96 (1H, br s), 7.12 (1H, br d, J=3.9 Hz), 7.08 (1H, br m), 5.43 (1H, br s) and 2.63 (3H, s); ir (potassium bromide): 3362, 3191 br, 1729, 1600, 1565, 1374, 1348 and 1190 cm$^{-1}$.

EXAMPLE 41

5-Chloro-3-(3-methoxy-2-thenoyl)-2-oxindole-1-carboxamide

A 2.00 g (12.69 mmoles) sample of 3-methoxy-2-thiophenecarboxylic acid (prepared according to Gronowitz, S., Arkiv. for Kemi. 12:239 (1958)) was reacted with 10 ml of thionyl chloride according to Example 32. Evaporation of excess thionyl chloride left 2.17 g of 3-methoxy-2-thiophenecarbonyl chloride as a crystalline solid, m.p. 86–88° C. The acid chloride was coupled to 2.16 g (10.24 mmoles) of 5-chloro-2-oxindole-1-carboxamide in the presence of 3.30 g (27 mmoles) 4-(N,N-dimethylamino)pyridine according to the procedure in Example 32. Aqueous acid quench followed by filtration gave a yellow solid which was purified by recrystallization to give 1.04 g (2.96 mmoles, 29% yield) of 5-chloro-3-(3-methoxy-2-thenoyl)-2-oxindole-1-carboxamide as a yellow solid, m.p. 272–274° C. (acetic acid).

Analysis: Calculated for $C_{15}H_{11}ClN_2O_4S$: C, 51.36; H, 3.16; N, 7.99%. Found: C, 50.97; H, 3.20; N, 7.81%. EIMS (m/z): 350/352 (M$^+$, 13%), 307/309 (M$^+$—CONH, 21%), 193/195 (M$^+$—CONH—$C_5H_6OS$, 92%), 141 ($C_6H_5O_2S$, 78%) and 114 ($C_5H_6O_2S$, base); $^1$HNMR (DMSO-d$_6$) delta, 8.26 (1H, br s), 8.13 (1H, d, J=8 Hz), 7.92 (1H, d, J=5 Hz), 7.69 (1H, br s), 7.56 (1H, br s, exchangeable), 7.23 (1H, dd, J=8, 1.5 Hz), 7.19 (1H, d, J=5 Hz) and 3.88 (3H, s); ir (potassium bromide): 3375, 3230 br, 1745, 1574, 1383 and 1074 cm$^{-1}$.

EXAMPLE 42

5-Chloro-3-(4-methoxy-2-thenoyl)-2-oxindole-1-carboxamide

The title compound was prepared according to the procedure of Example 32. A 1.30 g (8.22 mmoles) sample of 4-methoxy-2-thiophenecarboxylic acid (prepared according to Gronowitz, S., Arkiv. for Kemi. 12:239 (1958)) was converted to 1.19 g of pure acid chloride (b.p. 58–60° C., 0.03 mm) with 10 ml of thionyl chloride. The acid chloride was coupled to 1.18 g (5.61 mmoles) of 5-chloro-2-oxindole-1-carboxamide in the presence of 1.73 g (14.15 mmoles) 4-(N,N-dimethylamino)pyridine to give 1.88 g of crude product on acidic workup. Recrystallization gave 1.39 g (3.96 mmoles, 71% yield) of pure 5-chloro-3-(4-methoxy-2-thenoyl)-2-oxindole-1-carboxamide as a yellow solid, m.p. 221–223° C. (acetic acid).

Analysis: Calculated for $C_{15}H_{11}ClN_2O_4S$: C, 51.36; H, 3.16; N, 7.99%. Found: C, 51.16; H, 3.11; N, 7.84%. EIMS (m/z): 350/352 (M$^+$, 27%), 307/309 (M$^+$—CONH, 71%), 193/195 (M$^+$—CONH—$C_5H_6OS$, base), 141 ($C_6H_5O_2S$, 52%) and 114 ($C_5H_6O_2S$, 50%); $^1$HNMR (DMSO-d$_6$) delta, 8.08 (1H, d, J=8 Hz), 7.92 (1H, br s), 7.76 (1H, br s), 7.10 (1H, br d, J=8 Hz), 6.93 (1H, br s), 5.36 (1H, br s, exchangeable) and 3.80 (3H, s); ir (potassium bromide): 3388, 3216 br, 1746, 1613, 1588, 1378 and 1189 cm$^{-1}$.

EXAMPLE 43

5-Chloro-3-(5-methoxy-2-thenoyl)-2-oxindole-1-carboxamide

The title compound was prepared according to the procedure of Example 32. The reaction of 10 ml of thionyl chloride with 1.75 g (11.06 mmoles) of 5-methoxy-2-thiophenecarboxylic acid (prepared according to Sice, J., J. Am. Chem. Soc. 75:3697 (1953)) produced 1.83 g of the corresponding acid chloride as a brown oil. Coupling of 5-methoxy-2-thiophenecarbonyl chloride with 1.82 g (8.63 mmoles) of 5-chloro-2-oxindole-1-carboxamide in the presence of 2.66 g (21.76 mmoles) 4-(N,N-dimethylamino) pyridine produced 3.11 g of crude product as a yellow solid. Recrystallization from acetic acid gave 0.87 g of pure 5-chloro-3-(5-methoxy-2-thenoyl)-2-oxindole-1-carboxamide as a yellow solid, m.p. 180–2° C.

Analysis: Calculated for $C_{15}H_{11}ClN_2O_4S$: C, 51.36; H, 3.16; N, 7.99%. Found: C, 51.15; H, 3.07; N, 7.77%. EIMS (m/z): 350/352 (M$^+$, 22%), 307/309 (M$^+$—CONH, 81%), 193/195 (M$^+$—CONH—C H$_6$OS, 75%), 141 ($C_6H_5O_2S$, 98%) and 114 ($C_5H_6O_2S$, base); $^1$HNMR (DMSO-d$_6$) delta, 8.11 (1H, d, J=8.5 Hz), 8.04 (1H, br s), 7.90 (1H, br s), 7.12 (1H, br s), 6.52 (1H, br s), 4.92 (1H, br s) and 4.0 (3H, s); ir (potassium bromide): 3393, 3200 br, 1755, 1605, 1585, 1544, 1489, 1423, 1301 and 1052 cm$^{-1}$.

EXAMPLE 44

5-Chloro-3-(5-ethoxy-2-thenoyl)-2-oxindole-1-carboxamide

The title compound was prepared according to the procedure of Example 32. Reaction of 1.39 g (8.07 mmoles) of 5-ethoxy-2-thiophenecarboxylic acid (prepared according to Sice, J., J. Am. Chem. Soc. 75:3697 (1953)) with 10 ml of thionyl chloride provided 1.05 g (5.51 mmoles, 68% yield) of pure acid chloride after distillation (b.p. 72–75° C./0.1 mm) as a low melting solid. Acylation of 0.94 g (4.46 mmoles) of 5-chloro-2-oxindole-1-carboxamide with 1.02 g (5.35 mmoles) of 5-ethoxy-2-thiophenecarbonyl chloride in the presence of 1.37 g (11.23 mmoles) of 4-(N,N-dimethylamino)pyridine produced 1.50 g of crude yellow solid. Recrystallization of the crude solid in acetic acid furnished 0.20 g (0.55 mmoles, 12% yield) of pure title compound as a yellow solid, m.p. 183–5° C.

Analysis: Calculated for $C_{16}H_{13}ClN_2O_4S$: C, 52.67; H, 3.59; N, 7.68%. Found: C, 52.70; H, 3.49; N, 7.60%. EIMS (m/z): 364/366 (M$^+$, base), 321/323 (M$^+$—CONH, 80%), 193/195 (M$^+$—CONH—$C_6H_8OS$, 74%), 155 ($C_7H_7O_2S$, 72%) and 128 ($C_6H_8OS$, 78%); $^1$HNMR (DMSO-d$_6$) delta, 8.10 (1H, d, J=8.5 Hz), 8.04 (1H, br s), 7.90 (1H, br s), 7.10 (1H, br s), 6.50 (1H, br s), 4.63 (1H, br s, exchangeable), 4.26 (2H, br q, J=7 Hz) and 1.40 (3H, t, J=7 Hz); ir (potassium bromide): 3394, 3209 br, 1752, 1609, 1585, 1481, 1375, 1352 and 1296 cm$^{-1}$.

EXAMPLE 45

5-Chloro-3-(4-acetoxy-2-thenoyl)-2-oxindole-1-carboxamide

The title compound was prepared according to the procedure of Example 32. The reaction of 15 ml of thionyl chloride with 3.58 g (19.23 mmoles) of 4-acetoxy-2-thiophenecarboxylic acid (prepared according to Bohlmann, F., et al., Chem. Ber. 106:497 (1973)) gave a yellow oil. A 3.32 g (16.22 mmoles) sample of 4-acetoxy-2-thiophenecarbonyl chloride was coupled to 2.85 g (13.52 mmoles) of 5-chloro-2-oxindole-1-carboxamide in the presence of 4.16 g (34.07 mmoles) 4-(N,N-dimethylamino) pyridine to give 5.40 g of crude yellow product. Purification by recrystallization gave 4.18 g (11.02 mmoles, 82%) of pure title compound as a yellow solid, m.p. 222–224° C. (acetic acid).

Analysis: Calculated for $C_{16}H_{11}ClN_2O_5S$: C, 50.73; H, 2.93; N, 7.40%. Found: C, 50.53; H, 2.89; N, 7.22%. EIMS (m/z): 378/380 (M$^+$, 3%), 335/337 (M$^+$—CONH, 12%), 293/295 (M$^+$—CONH—COCH$_2$, 9%), 193/195 (M$^+$—CONH—$C_6H_6O_2S$, base), 169 ($C_7H_5O_3S$, 24%) and 127 ($C_5H_3O_2S$, 71%); $^1$HNMR (DMSO-d$_6$) delta, 8.15 (1H, d, J=1.5 Hz), 8.07 (1H, d, J=8.5 Hz), 8.01 (1H, br s), 7.52 (1H, br s), 7.03 (1H, br d, J=8.5 Hz), 5.03 (1H, br s, exchangeable) and 2.29 (3H, s); ir (potassium bromide): 3389, 3217 br, 1773, 1742, 1618, 1589, 1369 and 1210 cm$^{-1}$.

EXAMPLE 46

5-Chloro-3-(5-acetyl-2-thenoyl)-2-oxindole-1-carboxamide

The title compound was prepared according to the procedure of Example 32. In the first step, 2.0 g (11.75 mmoles) of 5-acetyl-2-thiophenecarboxylic acid (prepared according to Thames, S. F., et al., J. Het. Chem. 3:104 (1966)) was treated with 15 ml of thionyl chloride. Evaporation of the excess thionyl chloride gave a gummy residue which was triturated with carbon tetrachloride to give 0.92 g (4.88 mmoles, 42% yield) of 5-acetyl-2-thiophenecarbonyl chloride as a light orange solid, m.p. 78–80° C. Then, 0.90 g (4.77 mmoles) of acid chloride was reacted with 0.83 g (3.95 mmoles) of 5-chloro-2-oxindole-1-carboxamide in the presence of 1.22 g (9.97 mmoles) 4-(N,N-dimethylamino) pyridine to give 1.42 g (3.91 mmoles, 99%) of pure title compound, after aqueous acid workup and drying, as an orange-yellow solid, m.p. 218–21° C.

Analysis: Calculated for $C_{16}H_{11}ClN_2O_4S$: C, 52.97; H, 3.06; N, 7.72%. Found: C, 52.76; H, 3.01; N, 7.58%. EIMS (m/z): 362/364. ($M^+$, 1%), 319/321 ($M^+$—CONH, 7%), 193/195 ($M^+$—CONH—$C_6H_6OS$, 58%) and 153 ($C_7H_5O_2S$, base); $^1$HNMR (DMSO-$d_6$) delta, 8.08 (1H, d, J=8.5 Hz), 8.07 (1H, d, J=4 Hz), 8.01 (1H, br d, J=1.5 Hz), 7.92 (1H, d, J=4 Hz), 7.07 (1H, dd, J=8.5, 1.5 Hz), 5.22 (1H, br s, exchangeable) and 2.60 (3H, s); ir (potassium bromide): 3379, 3170 br, 1734, 1672, 1607, 1599, 1573, 1354, 1263 and 1194 cm$^{-1}$.

EXAMPLE 47

5-Chloro-3-(4-methylsulfonyl-2-thenoyl)-2-oxindole-1-carboxamide

The title compound was prepared according to the procedure of Example 32. The reaction of 10 ml of thionyl chloride with 1.39 g (6.7 mmoles) of 4-methylsulfonyl-2-thiophenecarboxylic acid (prepared according to Arndt, F., et al., Chem. Ber. 94:1757 (1961)) gave 1.54 g of the crude acid chloride as a solid. The entire amount of 4-methylsulfonyl-2-thiophenecarbonyl chloride was coupled to 1.28 g (6.1 mmoles) of 5-chloro-2-oxindole-1-carboxamide in the presence of 2.24 g (18.3 mmoles) 4-(N,N-dimethylamino)pyridine. Acidic workup gave 2.28 g of crude product as an orange solid. Recrystallization from 2-butanone gave two crops of slightly impure yellow crystalline solid which had a combined mass of 2.18 g. Further purification by recrystallization provided 1.19 g (2.98 mmoles, 49% yield) of pure 5-chloro-3-(4-methylsulfonyl-2-thenoyl)-2-oxindole-1-carboxamide as a yellow crystalline solid, m.p. 228–30° C. (acetic acid).

Analysis: Calculated for $C_{15}H_{11}ClN_2O_5S_2$: C, 45.17; H, 2.78; N, 7.02%. Found: C, 45.05; H, 2.68; N, 6.83%. EIMS (m/z): 398/400 ($M^+$, 3%), 355/357 ($M^+$—CHNO, 24%), 193/195 ($M^+$—CHNO—$C_5H_6O_2S_2$, base) and 189 ($C_6H_5O_3S_2$, 39%); $^1$HNMR (DMSO-$d_6$) delta, 8.83 (1H, d, J=1Hz), 8.43 (1H, br s), 8.12 (1H, br d, J=1.5 Hz), 8.03 (1H, d, J=8.5 Hz), 6.91 (1H, dd, J=8.5, 1.5 Hz), 5.05 (1H, exchangeable) and 3.24 (3H, s); ir (potassium bromide): 3380, 3206 br, 3084, 1732, 1574, 1311 and 1138 cm$^{-1}$.

EXAMPLE 48

5-Chloro-3-(5-methylsulfonyl-2-thenoyl)-2-oxindole-1-carboxamide

The title compound was prepared according to the procedure of Example 32. A 2.06 g (10.0 mmoles) sample of 5-methylsulfonyl-2-thiophenecarboxylic acid (prepared according to Cymerman-Craig, J., et al., J. Chem. Soc.:237 (1954)) reacted with 10 ml of thionyl chloride to give 2.14 g of crude acid chloride as a solid. The reaction of 1.75 g (8.33 mmoles) of 5-chloro-2-oxindole-1-carboxamide with 5-methylsulfonyl-2-thiophenecarbonyl chloride in the presence of 3.05 g (25.0 mmoles) of 4-(N,N-dimethylamino) pyridine gave 3.17 g of crude product after acidic workup. A single recrystallization from acetic acid gave 2.31 g (5.80 mmoles, 70% yield) of pure 5-chloro-3-(5-methylsulfonyl-2-thenoyl)-2-oxindole-1-carboxamide as a deep-orange solid, m.p. 212–14° C.

Analysis: Calculated for $C_{15}H_{11}ClN_2O_5S_2$: C, 45.17; H, 2.78; N, 7.02%. Found: C, 45.15; H, 2.78; N, 6.75%. EIMS (m/z): 398/400 ($M^+$, 2%), 355/357 ($M^+$—CHNO, 21%), 193/195 ($M^+$—CHNO—$C_5H_6O_2S_2$, base) and 189 ($C_6H_5O_3S_2$, 23%); $^1$HNMR (DMSO-$d_6$) delta, 8.34 (1H, d, J=4 Hz), 8.06 (1H, d, J=1.5 Hz), 7.99 (1H, d, J=8.5 Hz), 7.69 (1H, br d, J=4.0 Hz), 6.89 (1H, dd, J=8.5, 1.5 Hz), 5.76 (1H, br s, exchangeable) and 3.32 (3H, s); ir (potassium bromide): 3363, 3162 br, 1732, 1580, 1318 and 1148 cm$^{-1}$.

EXAMPLE 49

5-Chloro-3-(5-(N,N-dimethylsulfonamido)-2-thenoyl)-2-oxindole-1-carboxamide

The title compound was prepared according to the procedure of Example 32. Reaction of 10 ml of thionyl chloride with 2.35 g (10.0 mmoles) of 5-(N,N-dimethylsulfonamido)-2-thiophenecarboxylic acid (prepared as described in Example 29) gave 2.58 g of impure acid chloride as a solid. A 2.54 g sample of 5-(N,N-dimethylsulfonamido)-2-thiophenecarbonyl chloride was coupled to 1.75 g (8.33 mmoles) of 5-chloro-2-oxindole-1-carboxamide using excess (3.05 g, (25.0 mmoles)) of 4-(N,N-dimethylamino)pyridine to give 3.55 g of crude product as an orange solid. Recrystallization of the crude product gave 2.40 g (5.61 mmoles, 67% yield) of pure title compound as a yellowish-orange solid, m.p. 227–30° C. (2-butanone).

Analysis: Calculated for $C_{16}H_{14}ClN_3O_5S_2$: C, 44.91; H, 3.30; N, 9.82%. Found: C, 45.02; H, 3.26; N, 9.62%. EIMS (m/z): 427/429 ($M^+$, 2%), 384/386 ($M^+$—CHNO, 18%), 218 ($C_7H_8NO_3S$, 26%) and 193/195 ($M^+$—CHNO—$C_6H_9NO_2S_2$, base); $^1$HNMR (DMSO-$d_6$) delta, 8.50 (1H, d, J=3.9 Hz), 8.13 (1H, d, J=1.5 Hz), 8.06 (1H, d, J=8.5 Hz), 7.60 (1H, d, J=3.9 Hz), 6.96 (1H, dd, J=8.5, 1.5 Hz), 5.65 (1H, br s, exchangeable) and 2.71 (6H, s); ir (potassium bromide): 3454 br, 3336, 1729, 1595, 1566, 1335, 1209 and 1155 cm$^{-1}$.

EXAMPLE 50

5-Chloro-3-(4-methoxymethyl-2-thenoyl)-2-oxindole-1-carboxamide

The title compound was prepared according to the procedure of Example 32. A 1.40 g (8.13 mmoles) sample of 4-methoxymethyl-2-thiophenecarboxylic acid (prepared according to Nemec, N., et al., Coll. Czech. Chem. Comm. 39:3527 (1974)) was treated with 10 ml of thionyl chloride to give the crude acid chloride. Fractional distillation separated 0.89 g of pure 4-methoxymethyl-2-thiophenecarbonyl chloride, b.p. 65–67° C. (0.05 mm). Reaction of 0.88 g (4.61 mmoles) of acid chloride with 0.81 g (3.84 mmoles) of 5-chloro-2-oxindole-1-carboxamide in the presence of 1.18 g (9.67 mmoles) 4-(N,N-dimethylamino)pyridine gave 1.27 g of isolated orange solid after aqueous acid workup. Recrystallization of the orange solid followed by silica gel chromatography provided 0.32 g (0.88 mmoles, 23% yield) of pure 5-chloro-3-(4-methoxymethyl-2-thenoyl)-2-oxindole-1-carboxamide as a greenish-yellow solid, m.p. 193–5° C.

Analysis: Calculated for $C_{16}H_{13}ClN_2O_4S$: C, 52.67; H, 3.59; N, 7.68%. Found: C, 51.56; H, 3.38; N, 7.51%. EIMS (m/z): 364/366 (M+, 21%), 332/334 (M+—CH₃OH, 12%), 321/323 (M+—CHNO, 20%), 289/291 (M+—CHNO, —CH₃OH, 56%), 193/195 (M+—CHNO—C₆H₈OS, base) and 155 (C₇H₇O₂S, 44%); ¹HNMR (DMSO-d₆) delta, 8.09 (1H, d, J=8.5 Hz), 7.98 (1H, br s), 7.90 (1H, br s), 7.71 (1H, br s), 7.10 (1H, br ds, J=8.5 Hz), 4.86 (1H, br s, exchangeable), 4.42 (2H, s) and 3.30 (3H, s); ir (potassium bromide): 3391, 3222 br, 1744, 1615, 1587, 1574, 1380 and 1195 cm⁻¹.

EXAMPLE 51

5-Chloro-3-(5-methoxymethyl-2-thenoyl)-2-oxindole-1-carboxamide

The title compound was prepared according to the procedure of Example 32. A 2.06 g (11.96 mmoles) sample of 5-methoxymethyl-2-thiophenecarboxylic acid (prepared according to Janda, M., et al., Coll. Czech. Chem. Comm. 27:1191 (1962)) was heated with 20 ml of thionyl chloride. On completion of the reaction excess thionyl chloride was evaporated and the residue distilled to give 1.83 g (9.60 mmoles, 80% yield) of pure 5-methoxymethyl-2-thiophenecarbonyl chloride as a colorless oil, b.p. 62–7° C. (0.05 mm). Reaction of the entire acid chloride with 1.68 g (8.00 mmoles) of 5-chloro-2-oxindole-1-carboxamide in the presence of 2.46 g (20.16 mmoles) 4-(N,N-dimethylamino)pyridine provided 2.61 g of orange solid after acidic workup. Recrystallization of the product gave 0.98 g (2.69 mmoles, 34% yield) of pure title compound as a brown solid, m.p. 203–5° C. (2-butanone).

Analysis: Calculated for $C_{16}H_{13}ClN_2O_4S$: C, 52.67; H, 3.59; N, 7.68%. Found: C, 52.88; H, 3.64; N, 7.55%. EIMS (m/z): 364/366 (M+, 19%), 321/323 (M+—CHNO, 27%), 289/291 (M+—CHNO—CH₃OH, 20%), 193/195 (M+—CHNO—C₆H₈OS, base) and 155 (C₇H₇O₂S, 76%); ¹HNMR (DMSO-d₆) delta, 8.08 (1H, d, J=8.5 Hz), 7.87 (1 or 2H, br s), 7.10 (1 or 2H, br s), 4.89 (1H, br s, exchangeable), 4.63 (2H, s) and 3.32 (3H, s); ir (potassium bromide): 3382, 3205 br, 1752, 1605, 1584 and 1287 cm⁻¹.

EXAMPLE 52

5-Chloro-3-(5-N,N-dimethylcarbamido-2-thenoyl)-2-oxindole-1-carboxamide

Following the procedure of Example 32, 1.25 g (6.27 mmoles) of 5-[(N,N-dimethylamino)carbonyl]-2-thiophenecarboxylic acid (prepared as described in Example 5) was converted to 1.32 g (6.08 mmoles, 97% yield) of the corresponding acid chloride, m.p. 109–11° C., by reaction with excess thionyl chloride. Coupling of 5-[(N,N-dimethylamino)carbonyl]-2-thiophenecarbonyl chloride to 1.06 g (5.05 mmoles) of 5-chloro-2-oxindole-1-carboxamide in the presence of 1.56 g (12.73 mmoles) 4-(N,N-dimethylamino)pyridine gave an orange solid after acidic workup. Recrystallization of the solid provided 0.80 g (2.05 mmoles, 40% yield) of pure title compound as an orange solid, m.p. 219–20° C. (acetic acid).

Analysis: Calculated for $C_{17}H_{14}ClN_3O_4S$: C, 52.11; H, 3.60; N, 10.72%. Found: C, 51.85; H, 3.49; N, 10.42%. EIMS (m/z) 391/393 (M+, 6%), 348/350 (M+—CONH, 10%), 193/195 (M+—CONH—C₇H₈NOS, base) and 182 (C₈H₈NO₂S, 56%); ¹HNMR (DMSO-d₆) delta, 8.08 (1H, d, J=8.5 Hz), 8.00 (1H, d, J=4.0 Hz), 7.96 (1H, br s), 7.48 (1H, d, J=4.0 Hz), 7.08 (1H, d, J=8.5 Hz), 6.20 (1H, br s, exchangeable) and 3.13 (6H, br s); ir (potassium bromide): 3372, 3224, 1726, 1603, 1392 and 1193 cm⁻¹.

EXAMPLE 53

5-Chloro-3-(3-fluoro-2-thenoyl)-2-oxindole-1-carboxamide

Excess thionyl chloride (3.0 ml, 41.1 mmoles) and 0.89 g (6.10 mmoles) of 3-fluoro-2-thiophenecarboxylic acid (prepared according to Corral, C., et al., Heterocycles 23:1431 (1985)) were mixed in 10 ml of toluene and reacted according to the procedure of Example 31. This gave the corresponding acid chloride as a yellow oil after workup. The yellow acid chloride was dissolved in 3 ml of N,N-dimethylformamide and reacted with 1.28 g (6.10 mmoles) of 5-chloro-2-oxindole-1-carboxamide in the presence of 1.64 g (13.42 mmoles) of 4-(N,N-dimethylamino)pyridine in 5 ml of N,N-dimethylformamide. Workup gave 1.7 g of yellow solid. Recrystallization of this material gave 0.65 g (31% yield) of title compound as yellow needles, m.p. 235–240° C. (acetic acid).

Analysis Calculated for $C_{14}H_8ClFN_2O_3S$: C, 49.64; H, 2.38; N, 8.27%. Found: 49.64; H, 2.32; 8.43%. ACE/EIMS (m/z): 338/340 (M+, 10%), 295/297 (M+—CHNO, 45%), 193/195 (M+—CHNO—C₄H₃FS, base) and 129 (C₅H₂FOS, 70%). HNMR (DMSO-d₆) delta, 9.15 (1H, br s, exchangeable), 8.28 (1H, br s, exchangeable), 8.10 (1H, d, J=8.5 Hz), 7.88 (1H, dd, J=5.2, 4.3 Hz), 7.81 (1H, d, J=1.5 Hz), 7.60 (1H, br s, exchangeable), 7.21 (1H, dd, J=8.5, 1.5 Hz) and 7.11 (1H, d, J=5.2 Hz). ¹³CNMR (DMSO-d₆) delta, 167.1, 160.2, 158.1 and 154.6, 152.6, 134.2, 129.2, 127.6, 125.4, 125.2, 120.8, 117.4, 115.9, 114.9 and 114.7, and 103.0. ir (potassium bromide): 3400, 3240 br, 1750, 1625, 1585, 1390, 1290, 1205 and 820 cm⁻¹.

EXAMPLE 54

5-Chloro-3-(3-methylthio-2-thenoyl)-2-oxindole-1-carboxamide

3-Methylthio-2-thiophenecarboxylic acid (prepared according to Carpenter, A. J., et al., Tetrahedron Letters 26:1777 (1985)) (2.61 g, 15.0 mmoles) was reacted with 10 ml of thionyl chloride to give 2.83 g of crude 3-methylthio-2-thiophenecarbonyl chloride as a light yellow solid. The acid chloride was then coupled to 2.57 g (12.2 mmoles) 5-chloro-2-oxindole-1-carboxamide in the presence of 4.47 g (36.6 mmoles) 4-(N,N-dimethylamino)pyridine as described in Example 32 to give 3.73 g of crude product as an orange solid. The product was partially purified by recrystallization from 2-butanone to give 1.44 g of greenish-yellow solid. Pure title compound was obtained by a second recrystallization from ethyl acetate to give 0.92 g (2.51 mmoles, 21% yield) as a yellow solid. The pure compound initially melts at 178° C. then resolidifies and melts again above 275° C. (dec.).

Analysis: Calculated for $C_{15}H_{11}ClN_2O_3S_2$: C, 49.11; H, 3.02; N, 7.64%. Found: C, 49.22; H, 2.98; N, 7.57%. EIMS (m/z): 366/368 (M+, 8%), 193/195 (M+—CONH—C₅H₆S₂, 48%), 157 (C₆H₅OS₂, 92%) and 130 (C₅H₆S₂, base); ¹HNMR (DMSO-d₆) delta, 8.26 (1H, br s, exchangeable), 8.11 (1H, d, J=8.5 Hz), 7.87 (1H, d, J=4.5 Hz), 7.71 (1H, br s), 7.58 (1H, br s, exchangeable), 7.26 (1H, d, J=4.5 Hz), 7.21 (1H, br d, J=8.5 Hz) and 2.43 (3H, s); ir (potassium bromide): 3388, 3198 br, 1727, 1670, 1611, 1571, 1367, 1265, 1191 and 805 cm⁻¹.

EXAMPLE 55

5-Chloro-3-(4-acetyl-2-thenoyl)-2-oxindole-1-carboxamide

A 0.78 g (4.59 mmoles) sample of 4-acetyl-2-thiophenecarboxylic acid (prepared according to Satonaka, H., Bull. Chem. Soc. Japan 56:2463 (1983)) was combined with 0.95 g (5.85 mmoles) of 1,1'-carbonyldiimidazole in 10 ml of N,N-dimethylformamide and stirred at room temperature under argon atmosphere. After two hours the reaction contents were transferred to an addition funnel and slowly added to a slurry of 0.88 g (4.18 mmoles) of 5-chloro-2-oxindole-1-carboxamide and 1.38 g (11.28 mmoles) of 4-(N,N-dimethylamino)pyridine in 30 ml of N,N-dimethylformamide stirring at 5° C. (ice bath) under an inert atmosphere. The reaction contents were stirred for fifteen minutes at 5° C. after complete addition followed by twenty-four hours at room temperature. Pouring the reaction mixture into 110 ml of 0.3N hydrochloric acid cause the precipitation of a greenish-yellow solid. Filtration followed by sequential washing with 3N hydrochloric acid and water, provided the crude product which was recrystallized twice from acetic acid to give 0.34 g (0.94 mmoles, 22% yield) of pure 5-chloro-3-(4-acetyl-2-thenoyl)-2-oxindole-1-carboxamide as a greenish-yellow solvated complex with 0.2 equivalents of acetic acid, m.p. 230–233° C.

Analysis Calculated for $C_{16}H_{11}ClN_2O_4S \times 0.2\ C_2H_4O_2$: C, 52.55; H, 3.17; N, 7.47%. Found: C, 52.24; H, 2.88; N, 7.61%. EIMS(m/z): 362/364 (M$^+$, 9%), 319/321 (M$^+$—CONH, 43%), 193/195 (M$^+$—CONH—$C_6H_6OS$, base) and 153 ($C_7H_5O_2S$, 79%); $^1$NMR (DMSO-$d_6$) delta, 8.64 (1H, br s), 8.47 (1H, d, J=1.3 Hz), 8.07 (1H, d, J=8.5 Hz), 8.00 (1H, br s), 7.07 (1H, br d, J=8.5 Hz), 5.94 (1H, br s, exchangeable) and 2.52 (3H, s); ir (potassium bromide): 3387, 3230 br, 1743, 1692, 1623, 1592, 1577, 1384, 1272 and 1192 cm$^{-1}$.

EXAMPLE 56

5-Chloro-3-(4-methylsulfinyl-2-thenoyl)-2-oxindole-1-carboxamide

The title compound was prepared according to the procedure of Example 55. Acyl activation of 1.64 g (8.6 mmoles) of 4-methylsulfinyl-2-thiophenecarboxylic acid (prepared as described in Example 1) with 1.65 g (10.0 mmoles) of 1,1'-carbonyldiimidazole yielded the corresponding reactive acylimidazole intermediate which was used directly and coupled with 1.65 g (7.8 mmoles) of 5-chloro-2-oxindole-1-carboxamide in the presence of 2.87 g (23.5 mmoles) 4-(N,N-dimethylamino)pyridine to give a crude yellow product. Trituration of the yellow solid with 2-butanone gave 1.67 g (4.36 mmoles, 56% yield) of pure 5-chloro-3-(4-methylsulfinyl-2-thenoyl)-2-oxindole-1-carboxamide as a yellow solid, m.p. 204–206° C.

Analysis: Calculated for $C_{15}H_{11}ClN_2O_4S_2$: C, 47.06; H, 2.90; N, 7.32%. Found: C, 47.11; H, 2.91; N, 7.27%. EIMS (m/z): 382/384 (M$^+$, 7%), 339/341 (M$^+$—CHNO, 16%), 193/195 (M$^+$—CHNO—$C_5H_6OS_2$, base) and 173 ($C_6H_5O_2S_2$, 31%); $^1$HNMR (DMSO-$d_6$) delta, 8.36 (1H, br s), 8.27 (1H, br s), 8.11 (1H, d, J=8.5 Hz), 7.99 (1H, br s), 7.13 (1H, br d, J=8.5 Hz) and 2.88 (3H, s); ir (potassium bromide): 3385, 3220 br, 1721, 1612, 1573, 1376 and 1193 cm$^{-1}$.

EXAMPLE 57

5-Chloro-3-(5-sulfonamido-2-thenoyl)-2-oxindole-1-carboxamide

A 1.48 g (7.2 mmoles) sample of 5-sulfonamido-2-thiophenecarboxylic acid (prepared as described in Example 30) was transformed to the acyl imidazole by reaction with 1.39 g (8.6 mmoles) of 1,1'carbonyldiimidazole. The intermediate acylimidazole was coupled directly with 1.26 g (6.0 mmoles) of 5-chloro-2-oxindole-1-carboxamide in the presence of 2.2 g (18.0 mmoles) of 4-(N,N-dimethylamino)pyridine to give 2.34 g of a crude orange solid. Recrystallization gave 1.22 g (3.05 mmoles, 51% yield) of pure 5-chloro-3-(5-sulfonamido-2-thenoyl)-2-oxindole-1-carboxamide as a yellow-green solid, m.p. 227–229° C. (acetic acid).

Analysis: Calculated for $C_{14}H_{10}ClN_3O_5S_2$: C, 42.06; H, 2.52; N, 10.51%. Found: C, 41.78; H, 2.48; N, 10.15%. EIMS (m/z); 399/401 (M$^+$, 2%), 356/358 (M$^+$—CHNO, 23%), 193/195 (M$^+$—CHNO—$C_4H_5NO_2S_2$, base) and 190 ($C_5H_4NO_3S_2$, 53%); $^1$HNMR (DMSO-$d_6$) delta, 8.23 (1H, d, J=4 Hz), 8.05 (1H, br d, J=1.5 Hz), 8.02 (1H, d, J=8.5 Hz), 7.71 (br s, exchangeable), 7.49 (1H, d, J=4 Hz), 6.95 (1H, dd, J=8.5, 1.5 Hz) and 5.56 (br s, exchangeable); ir (potassium bromide): 3393, 3250, 3109 br, 1722, 1600, 1569, 1345, 1203 and 1150 cm$^{-1}$.

EXAMPLE 58

5-Chloro-3-(5-(N-methylsulfonamido)-2-thenoyl)-2-oxindole-1-carboxamide

The title compound was prepared according to the procedure of Example 55. Acyl activation of 2.21 g (10.0 mmoles) of 5-(N-methylsulfonamido)-2-thiophenecarboxylic acid (prepared as described in Example 2) with 1.95 g (12.0 mmoles) of 1,1'-carbonyldiimidazole generated the corresponding acylimidazole intermediate in 20 ml of N,N-dimethylformamide. This solution was transferred and slowly added to 1.75 g (8.33 mmoles) of 5-chloro-2-oxindole-1-carboxamide in 40 ml of N,N-dimethylformamide with 3.05 g (25.0 mmoles) of 4-(N,N-dimethylamino)pyridine. Acidic workup of the reaction furnished 2.96 g of a yellowish-orange solid. Recrystallization from acetic acid gave 1.90 g (4.59 mmoles, 55% yield) of pure title compound as a yellow solid, m.p. 225–227° C.

Analysis: Calculated for $C_{15}H_{12}ClN_3O_5S_2$: C, 43.53; H, 2.92; N, 10.15%. Found: C, 43.49; H, 2.86; N, 10.15%. EIMS (m/z): 413/415 (M$^+$, 2%), 370/372 (M$^+$—CHNO, 20%), 205 ($C_6H_7NO_3S_2$, 68%) and 193/195 (M$^+$—CHNO—$C_5H_7NO_2S_2$, base); $^1$HNMR (DMSO-$d_6$) delta, 8.32 (1H, d, J=4 Hz), 8.08 (1H, d, J=1.5 Hz), 8.05 (1H, d, J=8.5 Hz), 7.71 (br s, exchangeable), 7.53 (1H, d, J=4 Hz), 6.97 (1H, dd, J=8.5, 1.5 Hz), 5.77 (1H, br s, exchangeable) and 2.54 (3H, s); ir (potassium bromide): 3433 br, 3323 br, 1731, 1607, 1566 and 1151 cm$^{-1}$.

EXAMPLE 59

5-Chloro-3-(5-carboxy-2-thenoyl)-2-oxindole-1-carboxamide

The title compound was prepared according to the procedure of Example 55. A 1.00 g (5.81 mmoles) sample of commercial 2,5-thiophenedicarboxylic acid was reacted with 1.88 g (11.62 mmoles) of 1,1'-carbonyldiimidazole in 15 ml of N,N-dimethylformamide to give the activated acylimidazole. Slow addition of the acylimidazole to 1.11 g (5.28 mmoles) of 5-chloro-2-oxindole-1-carboxamide and 1.92 g (15.68 mmoles) of 4-(N,N-dimethylamino)pyridine in N,N-dimethylformamide gave a yellow-green solid after acidic workup. Final purification was achieved from a hot slurry of the title compound in acetic acid. This provided 1.51 g (4.14 mmoles, 78% yield) of 5-chloro-3-(5-carboxy-2-thenoyl)-2-oxindole-1-carboxamide as a yellow solid, m.p. 274–278° C.

Analysis: Calculated for $C_{15}H_9ClN_2O_5S$: C, 49.39; H, 2.49; N, 7.68%. Found: C, 49.19; H, 2.45; N, 7.38%. EIMS (m/z): 364/366 (M$^+$, 17%), 321/323 (M$^+$—CHNO, 73%), 193/195 (M$^+$—CHNO—$C_5H_4O_2S$, 98%) and 186 (unknown, base); $^1$HNMR (DMSO-$d_6$) delta, 8.10 (1H, d, J=4 Hz), 8.09 (1H, d, J=8.5 Hz), 8.03 (1H, br d, J=1.5 Hz), 7.74 (1H, d, J=4 Hz) and 7.08 (1H, dd, J=8.5, 1.5 Hz); ir (potassium bromide): 3388, 3276 br, 1718, 1695, 1551 and 1273 cm$^{-1}$.

EXAMPLE 60

5-Chloro-3-(4-methoxycarbonyl-2-thenoyl)-2-oxindole-1-carboxamide

The title compound was prepared according to the procedure of Example 55. To a solution of 1.50 g (8.06 mmoles) of 4-methoxycarbonyl-2-thiophenecarboxylic acid (prepared as described in Example 9) in 15 ml of N,N-dimethylformamide was added 1.57 g (9.67 mmoles) of 1,1'-carbonyldiimidazole. After two hours the reaction contents were slowly added to 1.54 g (7.32 mmoles) of 5-chloro-2-oxindole-1-carboxamide and 2.66 g (21.75 mmoles) of 4-(N,N-dimethylamino)pyridine in N,N-dimethylformamide. Acidic workup of this reaction followed by filtration, drying and trituration with hot acetic acid furnished 1.88 g (4.97 mmoles, 68% yield) of title compound as a yellow solid, m.p. 244–246° C.

Analysis: Calculated for $C_{16}H_{11}ClN_2O_5S$: C, 50.73; H, 2.93; N, 7.40%. Found: C, 50.52; H, 2.86; N, 7.12%. EIMS (m/z): 378/380 (M$^+$, 1%), 335/337 (M$^+$—CONH, 7%), 193/195 (M$^+$—CONH—$C_6H_5O_2S$, base), 169 ($C_7H_5O_3S$, 35%); $^1$HNMR (DMSO-$d_6$) delta, 8.59 (1H, d, J=1.4 Hz), 8.48 (1H, br s), 8.06 (1H, d, J=8.5 Hz), 8.05 (1H, br s), 7.02 (br d, J=8.5 Hz), 4.64 (1H, br s, exchangeable) and 3.82 (3H, s); ir (potassium bromide): 3383, 3217 br, 1746, 1590, 1375, 1279 and 745 cm$^{-1}$.

EXAMPLE 61

5-Chloro-3-(5-methoxycarbonyl-2-thenoyl)-2-oxindole-1-carboxamide

Following the procedure of Example 55, an N,N-dimethylformamide solution of 1.25 g (6.71 mmoles) of 5-methoxycarbonyl-2-thiophenecarboxylic acid (prepared as described in Example 11) was added to 1.19 g (7.35 mmoles) of 1,1'-carbonyldiimidazole to give an activated acyl intermediate. The reaction solution of this intermediate was slowly added to 1.29 g (6.10 mmoles) of 5-chloro-2-oxindole-1-carboxamide and 2.02 g (16.54 mmoles) of 4-(N,N-dimethylamino)pyridine also in N,N-dimethylformamide. Acidic workup followed by filtration, drying and recrystallization gave 1.29 g (3.41 mmoles, 56% yield) of title compound as a yellow solid, m.p. 219–221° C. (acetic acid).

Analysis: Calculated for $C_{16}H_{11}ClN_2O_5S$: C, 50.73; H, 2.93; N, 7.40%. Found: 50.76; H, 2.84; N, 7.38%. EIMS (m/z): 378/380 (M$^+$, 2%), 335/337 (M$^+$—CONH, 11%), 193/195 (M$^+$—CONH—$C_6H_5O_2S$, base) and 169 ($C_7H_5O_3S$, 46%); $^1$HNMR (DMSO-$d_6$) delta, 8.16 (1H, J=3.9 Hz), 8.05 (1H, d, J=8.5 Hz), 8.03 (1H, br s), 7.78 (1H, d, J=3.9 Hz), 7.02 (1H, dd, J=8.5, 2.3 Hz), 5.55 (1H, br s, exchangeable) and 3.84 (3H, s); ir (potassium bromide): 3388, 3216 br, 1730, 1589, 1290 and 745 cm$^{-1}$.

EXAMPLE 62

5-Chloro-3-(4-N,N-dimethylcarbamido-2-thenoyl)-2-oxindole-1-carboxamide

The title compound was prepared according to the procedure of Example 55. A 1.70 g (8.56 mmoles) sample of 4-[(N,N-dimethylamino)carbonyl]-2-thiophenecarboxylic acid (prepared as described in Example 5) was reacted with 1.77 g (10.90 mmoles) of 1,1'-carbonyldiimidazole to give an acylimidazole intermediate which was slowly added to an N,N-dimethylformamide solution of 1.64 g (7.80 mmoles) of 5-chloro-2-oxindole-1-carboxamide and 2.57 g (21.02 mmoles) of 4-(N,N-dimethylamino)pyridine. Acidic workup followed by filtration gave an orange solid which was recrystallized twice from acetic acid to give 0.86 g (2.19 mmoles, 28% yield) of pure title compound as a yellow solvated complex with 0.2 equivalents of acetic acid, m.p. 240–243° C.

Analysis: Calculated for $C_{17}H_{14}ClN_3O_4S \times 0.2\ C_2H_4O_2$: C, 51.75; H, 3.69; N, 10.41%. Found: C, 51.58; H, 3.46; N, 10.42%. EIMS (m/z): 391/393 (M$^+$, 26%), 348/350 (M$^+$—CONH, 20%), 193/195 (M$^+$—CONH—$C_7H_8NOS$, base) and 182 ($C_8H_8NO_2S$, 46%); $^1$HNMR (DMSO-$d_6$) delta, 8.16 (1H, br s), 8.08 (1H, d, J=8.5 Hz), 8.04 (1H, br s), 7.95 (1H, br s), 7.10 (1H, br d, J=8.5 Hz), 6.38 (1H, br s, exchangeable), 3.07 (3H, br s) and 2.98 (3H, br s); ir (potassium bromide): 3390, 3233, 1744, 1622, 1375 and 1195 cm$^{-1}$.

EXAMPLE 63

5-Chloro-3-(4-(2-methyl-4-thiazolyl)-2-thenoyl)-2-oxindole-1-carboxamide

The title compound was prepared according to the procedure of Example 55. A 1.25 g (5.55 mmoles) sample of 4-(2-methyl-4-thiazolyl)-2-thiophenecarboxylic acid (prepared as described in Example 18) was converted to the acyl imidazole by reaction with 0.98 g (6.05 mmoles) of 1,1'-carbonyldiimidazole in 15 ml of N,N-dimethylformamide. After complete reaction this solution was transferred to an addition funnel and slowly added 1.06 g (5.04 mmoles) of 5-chloro-2-oxindole-1-carboxamide and 1.66 g (13.59 mmoles) of 4-(N,N-dimethylamino)pyridine in 50 ml of N,N-dimethylformamide. Acidic workup followed by filtration and trituration with 2-butanone gave 0.50 g (1.20 mmoles) of title compound as a yellow solid, m.p. 238–241° C.

Analysis: Calculated for $C_{18}H_{12}ClN_3O_3S_2$: C, 51.73; H, 2.90; N, 10.06%. Found: C, 51.63; B, 2.95; N, 9.75%. EIMS (m/z): 417/419 (M$^+$, 1%), 374/376 (M$^+$—CONH, 8%), 208 ($C_9H_6NOS_2$, 34%), 193/195 (M$^+$—CONH—$C_8H_7NS_2$, 20%) and 181 ($C_8H_7NS_2$, base); $^1$HNMR (DMSO-$d_6$) delta, 8.44 (1H, br s), 8.13 (1H, br s), 8.09 (1H, d, J=8.4 Hz), 7.94 (1H, br s), 7.79 (1H, s), 7.10 (1H, d, J=8.4 Hz), 4.88 (1H, br s, exchangeable) and 2.71 (3H, s); ir (potassium bromide): 3385, 2919, 1747, 1587, 1374, 1196 and 729 cm$^{-1}$.

EXAMPLE 64

5-Chloro-3-(5-bromo-2-furanoyl)-2-oxindole-1-carboxamide

Using the procedure of Example 32, 1.91 g (10.0 mmoless) of commercially available 5-bromo-2-furancarboxylic acid was dissolved in 10 ml of thionyl chloride and heated to reflux under nitrogen for 1 hour and the acid chloride product was recovered. A 40 ml N,N-dimethylformamide solution of 1.75 g (8.3 mmoles) of 5-chloro-2-oxindole-1-carboxamide and 3.05 g (25 mmoles) of 4-(N,N-dimethylamino)pyridine was reacted with 2.09 g (10 mmoles) of 5-bromo-2-furan carbonyl chloride in 10 ml of N,N-dimethylformamide. After a reaction time of about 45 minutes, the mixture was acidified by pouring into 250 ml of 1N HCl. The product was recrystallized from acetic acid, washed with acetic acid, then hexane and dried overnight in vacuo at room temperature. The resulting product then was dried over refluxing isopropanol under high vacuum to yield 1.37 g of the title compound.

Analysis: Calculated for $C_{14}H_8BrClN_2O_4$: C, 43.84; H, 2.10; N, 7.30. Found: C, 43.94, H, 2.02, N, 7.16%; EIMS (m/z): 382/384 (M$^+$, 10%), 339/341 (M$^+$—CONH, 35%) and 193/195 (M$^+$—CONH—$C_4H_3$BrO, base); $^1$HNMR (DMSO-d$_6$) delta 8.50 (exchangeable), 8.08 (1H, d, J=8.5 Hz), 8.00 (1H, br s), 7.81 (1H, d, J=3.5 Hz), 7.63 (1H, exchangeable), 7.16 (1H, br d, J=8.5 Hz), 6.90 (1H, d, J=3.5 Hz) and 5.04 (exchangeable); IR (potassium bromide) 3382, 3220, 1735, 1723, 1620, 1587, 1533, 1464, 1379 and 1022 cm$^{-1}$.

EXAMPLE 65

5-Chloro-3-(6-chloronicotinoyl)-2-oxindole-1-carboxamide

The title compound was prepared according to the procedure of Example 55. Acyl activation of 823 mg (5.22 mmoles) of a commercial sample of 6-chloronicotinic acid with 924 mg (5.70 mmoles) of 1,1'-carbonyldiimidazole yielded the corresponding reactive acylimidazole intermediate which was used directly and coupled with 1.00 g (4.75 mmoles) of 5-chloro-2-oxindole-1-carboxamide in the presence of 1.57 g (12.85 mmoles) 4-(N,N-dimethylamino) pyridine to give a crude greenish-brown solid. Recrystallization of this solid gave 400 mg (1.14 mmole, 24% yield) of greenish-yellow solid, m.p. 236–8° C. (acetic acid).

Analysis: Calculated for $C_{15}H_9Cl_2N_3O_3$: C, 51.45; H, 2.59; N, 12.00%. Found: C, 51.54; H, 2.54; N, 11.69%. EIMS (m/z): 349/351/353 (M$^+$, 8%), 306/308/310 (M$^+$—CONH, 64%), 193/195 (M$^+$—CONH—$C_5H_4$ClN, base) and 140/142 ($C_6H_3$ClNO, 61%). $^1$H-NMR (DMSO-d$_6$) delta, 8.56 (1H, d, J=2.3 Hz), 8.37 (br s, exchangeable), 8.07 (1H, d, J=8.5 Hz), 8.01 (1H, dd, J=8.2, 2.3 Hz), 7.94 (1H, d, J=2.3 Hz), 7.60 (1H, d, J=8.2 Hz), 7.41 (br s, exchangeable), 7.11 (1H, dd, J=8.5, 2.3 Hz) and 4.93 (br s, exchangeable). ir (potassium bromide): 3390, 3210 (br), 1730, 1580, 1380, 1290, 1110 and 820 cm$^{-1}$.

EXAMPLE 66

5-Fluoro-3-(4-chloro-2-thenoyl)-2-oxindole-1-carboxamide

The title compound was prepared according to the procedure of Example 55. A 329 mg (2.02 mmole) portion of 4-chloro-2-thiophenecarboxylic acid (prepared according to Iriarte, J., et al., J. Het. Chem., 13, 393 (1976)) was combined with 358 mg (2.21 mmole) of 1,1'-carbonyldiimidazole in 5 ml of N,N-dimethylformamide and the intermediate imidazolide coupled directly with 357 mg (1.84 mmole) of 5-chloro-2-oxindole-1-carboxamide in the presence of 607 mg (4.96 mmole) 4-(N,N-dimethylamino) pyridine. The resulting crude yellow product was recrystallized to furnish 189 mg (0.558 mmole, 30% yield) of yellow solid, m.p. 224–6° C. (acetic acid).

Analysis: Calculated for $C_{14}H_8ClFN_2O_3S$: C, 49.64; H, 2.38; N, 8.27%. Found: C, 49.41; H, 2.28; N, 8.12%. EIMS (m/z): 338/340 (M$^+$, 4%), 295/297 (M$^+$—CONH, 19%), 177 (M$^+$—CONH—$C_4H_3$ClS, base) and 145/147 ($C_5H_2$ClOS, 39%); $^1$H-NMR (DMSO-d$_6$) delta, 8.80 (br s, exchangeable), 8.42 (1H, d, J=1.8 Hz), 8.04 (1H, dd, J=9.0, 5.8 Hz), 7.80 (1H, dd, J=10.5, 2.1 Hz), 7.74 (1H, br s), 7.30 (br s, exchangeable), 6.74 (1H, ddd, J=10.1, 9.0, 2.1 Hz) and 5.00 (br s, exchangeable); ir (potassium bromide): 3392, 3242 (br), 3112, 1743, 1588, 1381, 1182 and 838 cm$^{-1}$.

EXAMPLE 67

5-Trifluoromethyl-3-(4-chloro-2-thenoyl)-2-oxindole-1-carboxamide

The experimental procedure used to produce the title compound was adopted from Example 55. A 388 mg (2.39 mmole) sample of 4-chloro-2-thiophenecarboxylic acid (prepared according to Iriarte, J., et al., J. Het. Chem., 13, 393 (1976)) was transformed into the acyl imidazole by reaction with 420 mg (2.59 mmole) of 1,1'-carbonyldiimidazole. The intermediate 4-chloro-2-thiophene-(1-imidazo)carboxamide coupled directly with 486 mg (1.99 mmole) of 5-trifluoromethyl-2-oxindole-1-carboxamide in the presence of 657 mg (5.37 mmole) of 4-(N,N-dimethylamino)pyridine to give 634 mg (1.63 mmole, 82%) of the title compound as a yellow solid m.p. 164–6° C.

Analysis: Calculated for $C_{15}H_8ClF_3N_2O_3S$: C, 46.34; H, 2.07; N, 7.21%. Found: C, 46.29; H, 2.07; N, 7.79%. EIMS (m/z): 388/390 (M$^+$, 7%), 345/347 (M$^+$—CONH, 25%), 227 (M$^+$—CONH—$CH_4H_3$ClS, base) and 145/147 ($C_5H_2$ClOS, 26%); $^1$H-NMR (DMSO-d$_6$) delta, 9.10 (br s, exchangeable), 8.63 (1H, d, J=1.1 Hz), 8.46 (1H, s), 8.20 (1H, d, J=8.4 Hz), 7.69 (1H, d, J=1.1 Hz), 7.30 (br s, exchangeable), 7.20 (1H, dd, J=8.4, 1.4 Hz) and 5.28 (br s, exchangeable); ir (potassium bromide): 3397, 3233 (br), 1747, 1583, 1324, 1270, 1188 and 1122 cm$^{-1}$.

EXAMPLE 68

6-Chloro-3-(4-chloro-2-thenoyl)-2-oxindole-1-(N-ethyl)carboxamide

The title compound was prepared according to the experimental procedure described in Example 55. Acyl activation of 381 mg (2.34 mmoles) of 4-chloro-2-thiophenecarboxylic acid (prepared according to Iriarte, J., et al., J. Het. Chem., 13, 393 (1976)) with 412 mg (2.54 mmoles) of 1,1'-carbonyldiimidazole yielded the corresponding reactive acylimidazole which was used directly and coupled with 466 mg (1.95 mmoles) of 6-chloro-2-oxindole-1-(N-ethyl)carboxamide in the presence of 644 mg (5.27 mmole) of 4-(N,N-dimethylamino)pyridine to give 445 mg (59%) of a crude yellow solid. Recrystallization furnished the pure title compound (200 mg, 0.522 mmole, 27% yield) as a yellow crystalline solid, m.p. 164–6° C. (acetic acid).

Analysis: Calculated for $C_{16}H_{12}Cl_2N_2O_3S$: C, 50.14; H, 3.16; N, 7.31%. Found: C, 49.95; H, 3.01; N, 7.21%. EIMS (m/z): 382/384/386 (M$^+$, 5%), 311/313/315 (M$^+$—$C_3H_5$NO, 21%), 193/195 (M$^+$—$C_3H_5$NO, $C_4H_3$ClS, base) and 145/147 ($C_5H_2$ClOS, 40%). $^1$H-NMR (DMSO-d$_6$) delta, 9.43 (br s, exchangeable), 8.34 (1H, d, J=1.8 Hz), 8.12 (1H, d, J=1.9 Hz), 8.04 (1H, d, J=8.2 Hz), 7.74 (1H, br s), 7.04 (1H, dd, J=8.2, 1.9 Hz), 4.92 (br s, exchangeable), 3.29 (2H, br q, J=7.3 Hz) and 1.13 (3H, t, J=7.3 Hz). ir (potassium bromide): 3336, 3084, 1720, 1530, 1375, 1196 and 809 cm$^{-1}$.

EXAMPLE 69

5-Fluoro-3-(4-chloro-2-thenoyl)-2-oxindole-1-(N-t-butyl)carboxamide

The experimental procedure of Example 55 was used for the preparation of the title compound. A 390 mg (2.40 mmole) sample of 4-chloro-2-thiophenecarboxylic acid (prepared according to Iriarte, J., et al., J. Het. Chem., 13, 393 (1976)) reacted with 481 mg (2.60 mmole) of 1,1'-carbonyldiimidazole to give an acyl imidazole intermediate which was slowly added to an N,N-dimethylformamide solution of 500 mg (2.00 mmole) of 5-fluoro-2-oxindole-1-(N-t-butyl)carboxamide and 659 mg (5.39 mmole) of 4-(N,N-dimethylamino)pyridine. Acidic workup followed by recrystallization gave the title compound (260 mg, 0.66 mmole, 33% yield) as a yellow solid, m.p. 202–5° C. (acetic acid).

Analaysis: Calculated for $C_{18}H_{16}ClFN_2O_3S$: C, 54.75; H, 4.08; N, 7.10%. Found: C, 54.21; H, 3.76; N, 6.94%. EIMS (m/z): 394/396 ($M^+$, 1%), 295/297 ($M^+$—$C_5H_9NO$, 28%), 177 ($M^+$—$C_5H_9NO$—$C_4H_3ClS$, base) and 145/147 ($C_5H_2ClOS$, 24%). $^1$H-NMR (DMSO-$d_6$) delta, 9.55 (br s, exchangeable), 8.37 (1H, d, J=1.1 Hz), 8.05 (1H, dd, J=9.0, 5.2 Hz), 7.81 (1H, dd, J=10.5, 2.0 Hz), 7.73 (1H, br s), 6.73 (1H, ddd, J=10.5, 9.0, 2.0 Hz), 4.13 (br s, exchangeable) and 1.38 (9H, s). ir (potassium bromide): 3305, 3075, 2988, 1721, 1615, 1548, 1193 and 835 $cm^{-1}$.

EXAMPLE 70

6-Chloro-3-(4-chloro-2-thenoyl)-2-oxindole-1-carboxamide

The experimental procedure used to produce the title compound was adopted from Example 55. A 463 mg (2.85 mmole) portion of 4-chloro-2-thiophenecarboxylic acid (prepared according to Iriarte, J., et al., J. Het. Chem., 13, 393 (1976)) was transformed into the acyl imidazole by reaction with 500 mg (3.09 mmole) of 1,1'-carbonyldiimidazole. The intermediate 4-chloro-2-thiophene-(1-imidazo)carboxamide coupled directly with 500 mg (2.37 mmole) of 6-chloro-2-oxindole-1-carboxamide in the presence of 783 mg (6.41 mmole) of 4-(N,N-dimethylamino)pyridine to give 665 mg of crude greenish-yellow solid. Recrystallization gave 450 mg (1.27 mmole, 53% yield) of pure title compound as a yellow solid, m.p. 231–3° C. (acetic acid).

Analysis: Calculated for $C_{14}H_8Cl_2N_2O_3S$: C, 47.34; H, 2.27; N, 7.89%. Found: C, 47.11; H, 2.11; N, 7.73%. EIMS(m/z): 354/356/358 ($M^+$, 5%), 311/313/315 $M^+$—CONH, 15%), 193/195 ($M^+$—CONH—$C_4H_3ClS$, base) and 145/147 ($C_5H_2ClOS$, 49%). $^1$H-NMR (DMSO-$d_6$) delta, 8.80 (br s, exchangeable), 8.31 (1H, d, J=1.1 Hz), 8.10 (1H, d, J=2.2 Hz), 8.03 (1H, d, J=8.2 Hz), 7.74 (1H, br s), 7.36 (br s, exchangeable) 7.04 (1H, dd, J=8.2, 2.2 Hz) and 5.32 (br s, exchangeable). ir (potassium bromide): 3398, 3191 (br), 1749, 1726, 1587, 1368, 1196 and 807 $cm^{-1}$.

EXAMPLE 71

3-(4-Chloro-2-thenoyl)-2-oxindole-1-carboxamide

The title compound was prepared according to the procedure of Example 55. An 831 mg (5.11 mmole) portion of 4-chloro-2-thiophenecarboxylic acid (prepared according to Iriarte, J., et al., J. Het. Chem., 13, 393 (1976)) was combined with 897 mg (5.53 mmole) of 1,1'-carbonyldiimidazole in 5 ml of N,N-dimethylformamide and the intermediate imidazolide coupled directly with 750 mg (4.26 mmole) of 2-oxindole-1-carboxamide in the presence of 1.40 g (11.49 mmole) of 4-(N,N-dimethylamino)pyridine. The resulting crude yellow solid (803 mg, 59% yield) was recrystallized from acetic acid to furnish 376 mg (1.17 mmole, 27% yield) of fluffy yellow crystals, m.p. 221–3° C.

Analysis: Calculated for $C_{14}H_9ClN_2O_3S$: C, 52.42; H, 2.83; N, 8.74%. Found: C, 52.04; H, 2.62; N, 8.51%. EIMS (m/z): 320/322 ($M^+$, 3%), 277/279 ($M^+$—CONH, 6%), 159 ($M^+$—CONH—$C_4H_3ClS$, base) and 145/147 ($C_5H_2ClOS$, 50%). $^1$H-NMR (DMSO-$d_6$) delta, 8.10 (1H, br s), 8.09 (1H, d, J=8.5 Hz), 7.95 (br s), 7.83 (br s), 7.75 (br s), 7.30 (br), 7.08 (br) and 4.92 (br s, exchangeable); ir (potassium bromide): 3392, 3243 (br), 3117, 1744, 1591, 1379, 1268 and 1183 $cm^{-1}$.

EXAMPLE 72

5-Fluoro-6-chloro-3-(4-chloro-2-thenoyl)-2-oxindole-1-carboxamide

The title compound was prepared using the procedure from Example 55. A 427 mg (2.62 mmole) sample of 4-chloro-2-thiophenecarboxylic acid (prepared according to Iriarte, J., et al., J. Het. Chem., 13, 393 (1976)) was reacted with 461 mg (2.84 mmole) of 1,1'-carbonyldiimidazole in 5 ml of N,N-dimethylformamide to give the activated acylimidazole. Slow addition of the acylimidazole to 500 mg (2.19 mmole) of 5-fluoro-6-chloro-2-oxindole-1-carboxamide and 721 mg (5.90 mmole) of 4-(N,N-dimethylamino)pyridine in N,N-dimethylformamide gave a crude yellow solid (635 mg, 78% yield) after acidic workup. Recrystallization from acetic acid furnished a tan crystalline solid (390 mg, 1.05 mmole, 48% yield), m.p. 235–7° C.

Analysis: Calculated for $C_{14}H_7Cl_2FN_2O_3S$: C, 45.05; H, 1.89; N, 7.51%. Found: C, 44.81; H, 1.87; N, 7.44%. EIMS (m/z): 372/374/376 ($M^+$, 7%), 329/331/333 ($M^+$—CONH, 23%), 211/213 ($M^+$—CONH—$C_4H_3ClS$, base) and 145/147 ($C_5H_2ClOS$, 33%). $^1$H-NMR (DMSO-$d_6$) delta, 9.00 (br s, exchangeable), 8.62 (1H, d, J=1.2 Hz), 8.14 (1H, d, J=7.2 Hz), 8.02 (1H, d, J=11.2 Hz), 7.69 (1N, d, J=1.2 Hz), 7.25 (br s, exchangeable) and 4.32 (br s, exchangeable). ir (potassium bromide): 3386, 3231, 1715, 1610, 1580, 1464, 1366 and 1183 $cm^{-1}$.

EXAMPLE 73

6-Chloro-3-(5-bromo-3-furoyl)-2-oxindole-1-carboxamide

The experimental procedure used to produce the title compound was adopted from Example 55. A 750 mg (3.93 mmole) portion of 5-bromo-3-furoic acid (prepared according to Amaral, L., et al., J.O.C., 41, 2350 (1976)) was transformed into the acyl imidazole by reaction with 690 mg (4.25 mmole) of 1,1'-carbonyldiimidazole. The intermediate 5-bromo-3-furan-(1-imidazo)carboxamide coupled directly with 689 mg (3.27 mmole) of 6-chloro-2-oxindole-1-carboxamide in the presence of 1.08 g (8.83 mmole) of 4-(N,N-dimethylamino)pyridine to give 500 mg (40% yield) of crude greenish-yellow solid. Recrystallization gave 143 mg (0.37 mmole, 11% yield) of pure title compound as a greenish solid, m.p. 232–4° C. (acetic acid).

Analysis: Calculated for $C_{14}H_8BrClN_2O_4$: C, 43.83; H, 2.10; N, 7.30%. Found: C, 43.54; H, 2.00; N, 7.19%. EIMS (m/z): 382/384/386 ($M^+$, 11%), 339/341/343 ($M^+$—CONH, 30%), 260/262 ($M^+$—CONH—Br, 90%), 232/234 (unknown, 90%), 193/195 ($M^+$—CONH—$C_4H_3BrO$, 92%) and 173/175 ($C_5H_2BrO_2$, base). $^1$H-NMR (DMSO-$d_6$) delta, 8.43 (br s, exchangeable), 8.40 (1H, br s), 8.14 (1H, d, J=1.8 Hz), 7.92 (1H, d, J=8.2 Hz), 7.54 (br s, exchangeable), 7.15 (1H, dd, J=8.2, 1.9 Hz), 6.96 (1H, d, J=1.8 Hz) and 4.04 (br s, exchangeable); ir (potassium bromide): 3470, 3389, 3305 (br), 1757, 1718, 1579, 1387, 1198, 1122 and 915 $cm^{-1}$.

EXAMPLE 74

5-Fluoro-3-(5-bromo-3-furoyl)-2-oxindole-1-(N-t-butyl)carboxamide

The experimental procedure of Example 55 was used for the preparation of the title compound. A 641 mg (3.36 mmole) sample of 5-bromo-3-furoic acid (prepared according to Amaral, L., et al., J.O.C., 41, 2350 (1976)) reacted with 590 mg (3.64 mmole) of 1,1'-carbonyldiimidazole to give an acyl imidazole intermediate which was slowly added to an N,N-dimethylformamide solution of 700 mg (2.80 mmole) of 5-fluoro-2-oxindole-1-(N-t-butyl)carboxamide and 923 mg (7.56 mmole) of 4-(N,N-dimethylamino)pyridine. Acidic workup gave the crude title compound (777 mg, 66% yield) as a tan solid. Recrystallization furnished 256 mg (0.60 mmole, 22% yield) of an off-white crystalline solid, m.p. 190–2° C. (acetonitrile).

Analysis: Calculated for $C_{18}H_{16}BrFN_2O_4$: C, 51.08; H, 3.81; N, 6.62. Found: C, 50.98; H, 3.57; N, 6.61%. EIMS (m/z): 423/425 ($M^+$, 1%), 323/325 ($M^+$—$C_5H_{10}NO$, 35%), 244 ($M^+$—$C_5H_{10}NO$—Br, base), 216 (unknown, 95% and 57 ($C_4H_9$, 99%); $^1$H-NMR (DMSO-$d_6$) delta, 9.07 (br s, exchangeable), 8.44 (1H, d, J=1.4 Hz), 8.10 (1H, dd, J=9.0, 4.1 Hz), 7.67 (1H, dd, J=9.5, 2.8 Hz), 6.96 (1H, d, J=1.4 Hz), 6.91 (1H, ddd, J=9.5, 9.0, 2.8 Hz), 3.93 (br s, exchangeable) and 1.36 (9H, s); ir (potassium bromide): 3300, 3205, 2960, 1720, 1550, 1179 and 820 cm$^{-1}$.

EXAMPLE 75

5-Chloro-3-(5-bromo-3-thenoyl)-2-oxindole-1-carboxamide

The title compound was prepared according to the procedure of Example 55. A 1.00 g (4.83 mmole) portion of 5-bromo-3-thiophenecarboxylic acid (prepared as described in J. Am. Chem. Soc., 76, 2445 (1954)) was combined with 848 mg (5.23 mmole) of 1,1'-carbonyldiimidazole in 5 ml of N,N-dimethylformamide and the intermediate imidazolide coupled directly with 848 mg (4.02 mmole) of 5-chloro-2-oxindole-1-carboxamide in the presence of 1.33 g (10.89 mmole) of 4-(N,N-dimethylamino)pyridine. The resulting crude green product (1.22 g, 76% yield) was recrystallized to furnish 540 mg (1.35 mmole, 34% yield) of yellow solid, m.p. 238–40° C. (acetic acid).

Analysis: Calculated for $C_{14}H_8BrClN_2O_3S$: C, 42.07; H, 2.02; N, 7.01%. Found: C, 42.26; H, 1.98; N, 6.99%. EIMS (m/z): 398/400/402 ($M^+$, 39%), 355/357/359 ($M^+$—CONH, base), 276/278 ($M^+$—CONH—Br, 30%) and 193/195 ($M^+$—CONH—$C_4H_3BrS$, 75%); $^1$H-NMR (DMSO-$d_6$) delta, 8.36 (br s, exchangeable), 8.09 (1H, d, J=8.5 Hz), 8.08 (1H, d, J=1.6 Hz), 7.85 (1H, d, J=2.0 Hz), 7.52 (br s, exchangeable) 7.49 (1H, d, J=1.6 Hz), 7.16 (1H, dd, J=8.5, 2.0 Hz) and 3.73 (br s, exchangeable); ir (potassium bromide): 3389, 3218 (br), 1744, 1585, 1391, 1272 and 1194 cm$^{-1}$.

EXAMPLE 76

5-Chloro-3-(5-chloro-2-thiopheneacetyl)-2-oxindole-1-carboxamide

The title compound was prepared using the procedure from Example 55. A 1.00 g (5.66 mmole) sample of 5-chloro-2-thiopheneacetic acid (prepared according to Ford, et al., J. Am. Chem. Soc., 72, 2109 (1950)) was reacted with 995 mg (6.13 mmole) of 1,1'-carbonyldiimidazole in 5 ml of N,N-dimethylformamide to give the activated acylimidazole. Slow addition of the acylimidazole to 994 mg (4.72 mmole) of 5-chloro-2-oxindole-1-carboxamide and 1.44 g (11.79 mmole) of 4-(N,N-dimethylamino)pyridine in N,N-dimethylformamide gave a crude brownish-gray solid (1.52 g, 87% yield). Recrystallization from acetic acid furnished the title compound as a gray crystalline solid (387 mg, 1.05 mmole, 22% yield), m.p. 238–41° C.

Analysis: Calculated for $C_{15}H_{10}Cl_2O_3S$: C, 48.74; H, 2.68; N, 7.51%. Found: C, 48.79; H, 2.73; N, 7.59%. EIMS (m/z): 368/370/372 ($M^+$, 4%), 324/326/328 ($M^+$—CONH, 4%), 237/239 ($M^+$—$C_5H_4ClS$, 49%) and 194/195 ($M^+$—CONH—$C_5H_4ClS$, base); $1^1$H-NMR (DMSO-$d_6$)delta, 8.52 (br s, exchangeable), 8.07 (1H, d, J=8.5 Hz), 7.80 (1H, d, J=2.6 Hz), 7.12 (1H, dd, J=8.5, 2.6 Hz), 6.94 (1H, d, J=4.1 Hz), 6.90 (1H, d, J=4.1 Hz), 4.43 (2H, s) and 3.71 (br s, exchangeable); ir (potassium bromide): 3392, 3249 (br), 1724, 1695, 1664, 1582, 1381, 1287, 1202, 995 and 847 cm$^{-1}$.

EXAMPLE 77

5-Chloro-3-(5-methylthio-1,3,4-oxadiazol-2-yl)-2-oxindole-1-carboxamide

Using the procedure of Example 32, a 30 ml N,N-dimethylformamide solution of 958 mg (4.55 mmoles) of 5-chloro-2-oxindole-1-carboxamide and 1.50 g (12.28 mmoles) of 4-(N,N-dimethylamino)pyridine was reacted with 975 mg (5.46 mmoles) of 5-methylthio-1,3,4-oxadiazol-2-carbonyl chloride (U.S. Pat. No. 4,001,238). After acidic workup a crude orange solid (1.25 g, 78% yield) was obtained. Suspension in hot glacial acetic acid followed by filtration furnished the pure title compound (710 mg, 2.01 mmole, 44%) as a bright yellow solid, m.p. 297–9° C.

Analysis: Calculated for $C_{13}H_9ClN_4O_4S$: C, 44.26; H, 2.57; N, 15.88%. Found: C, 44.37; H, 2.52; N, 15.66%. EIMS (m/z): 352/354 ($M^+$, 4%), 309/311 ($M^+$—CONH, 12%) and 193/195 ($M^+$—CONH—$C_3H_4N_2OS$, base); $^1$H-NMR (DMSO-$d_6$) delta, 8.54 (br s, exchangeable), 8.00 (1H, d, J=8.6 Hz), 7.86 (1H, d, J=2.5 Hz), 7.18 (br s, exchangeable), 6.95 (1H, dd, J=8.6, 2.5 Hz), 4.04 (br s, exchangeable) and 2.72 (3H, s); ir (potassium bromide): 3496, 3348, 3107, 1728, 1551, 1442, 1306, 1216 and 849 cm$^{-1}$.

EXAMPLE 78

Methyl 3-ethoxy-5-isoxazolecarboxylate

A stirred suspension of 3.53 g (24.67 mmole) of a commercial sample of methyl 3-hydroxy-5-isoxazolecarboxylate in 50 ml of methylene chloride was treated dropwise with a solution of triethyloxonium tetrafluoroborate (5.62 g, 29.60 mmole) dissolved in 30 ml of methylene chloride at room temperature. After stirring overnight the solution was washed with water (2×30 ml), 5% sodium bicarbonate (2×30 ml) and water once again. The organic layer was dried (magnesium sulfate) and evaporated in vacuo to furnish the title compound (3.61 g, 86% yield) as a light yellow solid, m.p. 77–9° C. $^1$H-NMR (DMSO-$d_6$)delta, 6.65 (1H, s), 3.93 (2H, q, J=7.4 Hz), 3.87 (3H, s) and 1.21 (3H, t, J=7.4 Hz); EIMS (m/z): 171 ($M^+$, 48%), 156 ($M^+$—$CH_3$, 4%), 143 ($C_5H_5NO_4$, 31%), 112 ($C_4H_2NO_3$, 12%) and 69 ($C_3H_3NO$, base); ir (potassium bromide): 3105, 1744, 1611, 1441, 1241, 1106, 974 and 797 cm$^{-1}$.

EXAMPLE 79

3-Ethoxy-5-isoxazolecarboxylic Acid

A stirred solution of methyl 3-ethoxy-5-isoxazolecarboxylate, prepared according to Example 78, (3.00 g, 17.53 mmole) in 75 ml of 2N sodium hydroxide was stirred at room temperature for ten minutes, cooled in an icebath and acidified to pH 3 with concentrated hydrochloric acid. The precipitated solid was collected by filtration. The remaining desired product was isolated by saturating the aqueous filtrate with solid sodium chloride and extracting with ethyl acetate (3×100 ml). A total of 2.46 g (89% yield) of title compound was obtained in this way. The sample was recrystallized from acetonitrile, m.p. 210–13° C.

Analysis: Calculated for $C_6H_7NO_4$: C, 45.86; H, 4.49; N, 8.92%. Found: C, 45.80; H, 4.32; N, 8.87%. EIMS (m/z): 157 ($M^+$—$CH_3$, 22%), 129 ($C_4H_3NO_4$, 70%), 112 ($C_4H_2NO_3$, 15%) and 69 ($C_3H_3NO$, base); $^1$H-NMR (DMSO-6) delta, 6.51 (1H, s), 3.91 (2H, q, J=7.4 Hz) and 1.20 (3H, t, J=7.4 Hz); ir (potassium bromide): 3136 (br), 1726, 1626, 1238 and 984 $cm^{-1}$.

EXAMPLE 80

5-Chloro-3-(3-ethoxyisoxazo-5-yl)-2-oxindole-1-carboxamide

The experimental procedure of Example 55 was used for the preparation of the title compound. A 1.50 g (9.55 mmole) portion of 3-ethoxy-5-isoxazolecarboxylic acid, prepared according to Example 79, was reacted with 1.68 g (10.34 mmole) of 1,1'-carbonyldiimidazole to give an acyl imidazole intermediate which was slowly added to an N,N-dimethylformamide solution of 1.68 g (7.96 mmole) of 5-chloro-2-oxindole-1-carboxamide and 2.62 g (21.48 mmole) of 4-(N,N-dimethylamino)pyridine. Acidic workup gave the crude title compound as an orange-yellow solid (2.43 g, 87% yield). Suspension in hot glacial acetic acid followed by filtration furnished the pure title compound as a bright yellow solid (1.75 g, 5.00 nmnole, 63% yield) m.p. 260–2° C.

Analysis: Calculated for $C_{15}H_{12}ClN_3O_5$: C, 51.51; H, 3.46; N, 12.01%. Found: C, 51.57; H, 3.22; N, 11.89%. EIMS (m/z): 349/351 ($M^+$, 10%), 306/308 ($M^+$—CONH, 45%), 235/237 ($M^+$—$C_5H_8NO_2$, 20%) and 193/195 $M^+$—CONH, $C_5H_7NO_2$, 44%); $^1$H-NMR (DMSO-$d_6$)delta, 8.76 (br s, exchangeable), 8.01 (1H, d, J=8.6 Hz), 7.97 (1H, d, J=2.2 Hz), 7.30 (br s, exchangeable), 6.96 (1H, dd, J=8.6, 2.2 Hz), 6.30 (1H, s), 4.98 (br s, exchangeable), 3.86 (2H, q, J=7.4 Hz) and 1.21 (3H, t, J=7.4 Hz); ir (potassium bromide): 3315, 3228 (br), 1748, 1673, 1549, 1370, 843 and 819 $cm^{-1}$.

EXAMPLE 81

Methyl 5-(3-methyl-1,2,4-oxadiazol-5-yl)-2-thiophenecarboxylate

A stirred suspension of 5-methoxycarbonyl-2-thiophenecarboxylic acid (1.50 g, 8.06 mmole) in 15 ml of thionyl chloride was refluxed for two hours. The solution was cooled to room temperature and concentrated in vacuo to an almost colorless oil which crystallized under vacuum. This solid was dissolved in 5 ml of chloroform and added dropwise at room temperature to a stirred mixture of acetamide oxime (prepared according to Eloy, et al., Helv. Chim. Acta., 45, 441 (1962)) (657 mg, 8.86 mmole) and triethylamine (897 mg, 1.24 ml, 8.86 mmole) in 30 ml of chloroform. Once addition was complete the solution was stirred at room temperature for one hour and washed with water (2×20 ml). The organic layer was dried (magnesium sulfate), evaporated and the residue triturated with toluene to furnish the intermediate O-(2-methoxycarbonyl-5-thenoyl) acetamide oxime, 1.55 g (80% yield), as a white solid, m.p. 150–2° C. $^1$H-NMR (DMSO-$d_6$) delta, 8.03 (1H, d, J=3.9 Hz), 7.83 (1H, d, J=3.9 Hz), 6.54 (br s, exchangeable), 3.85 (3H, s) and 1.80 (3H, s). This material was used without additional purification.

A 1.43 g (5.90 mmole) portion of O-(2-methoxycarbonyl-5-thenoyl)acetamide oxime was suspended in 75 ml of toluene and warmed to reflux overnight. The solvent was removed in vacuo and the residue triturated with a small portion of toluene to furnish 1.10 g (83%) of the title compound as an off-white crystalline solid, m.p. 154–6° C. This material was used directly without further purification. Exact Mass: 224.0241, Calculated: 224.0256. EIMS (m/z): 224 ($M^+$, 98%) and 193 ($M^+$—$CH_3O$, base; $^1$H-NMR (DMSO-$d_6$) delta, 8.01 (1H, d, J=4.3 Hz), 7.92 (1H, d, J=4.3 Hz), 3.88 (3H, s) and 2.41 (3H, s).

EXAMPLE 82

5-(3-Methyl-1,2,4-oxadiazol-5-yl)-2-thiophenecarboxylic acid

A mixture of methyl 5-(3-methyl-1,2,4-oxadiazol-5-yl)-2-thiophenecarboxylate, prepared according to Example 81, (1.09 g, 4.86 mmole) in 35 ml of 2N sodium hydroxide was diluted with 5 ml of ethanol and warmed to 65° C. for thirty minutes. The solution was cooled in an ice bath and acidified to pH 2 with concentrated hydrochloric acid. Filtration and drying furnished 870 mg (85% yield) of the title compound as an off-white solid. The analytical sample was recrystallized from methanol, m.p. 226–8° C.

Analysis: Calculated for $C_8H_6N_2O_3S$: C, 45.70; H, 2.88; N, 13.33%. Found: C, 45.57; H, 2.75; N, 13.37%. EIMS (m/z): 210 ($M^+$, base) and 153 ($M^+$—$C_2H_3NO$, 99%); $^1$HMR (DMSO-$d_6$) delta, 7.97 (1H, d, J=3.9 Hz), 7.82 (1H, d, J=3.9 Hz) and 2.40 (3H, s); ir (potassium bromide): 3112 (br), 1699, 1289, 1112 and 840 $cm^{-1}$.

What is claimed is:
1. A compound of the formula

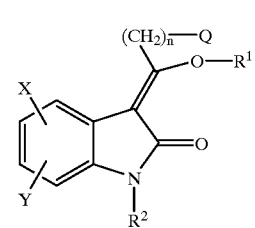

(I)

and the pharmaceutically-acceptable salts thereof, wherein
X is H, F, Cl, Br, ($C_1$–$C_6$)alkyl, ($C_3$–$C_8$)cycloalkyl, $NO_2$, $CF_3$, CN, SH, $S(O)_mR^3$, $OR^4$, $COR^4$ or $CONR^4R^5$;
Y is H, F, Cl, Br, ($C_1$–$C_6$)alkyl, ($C_3$–$C_8$)cycloalkyl, $NO_2$, $CF_3$, CN, SH, $S(O)_qR^{17}$, $OR^{18}$, $COR^{18}$ or $CONR^{18}R^{19}$;
$R^1$ is H, alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omega-alkoxycarbonylalkanoyl, said alkoxy having one to three carbon atoms and said alkanoyl having three to five carbon atoms, alkoxy carbonyl of two to ten carbon atoms, phenoxycarbonyl, 1-(acyloxy)alkyl wherein acyl has one to four carbon atoms and said alkyl has two to four carbon atoms, 1-(alkoxycarbonyloxy)alkyl wherein said alkoxy has two to five carbon atoms and said alkyl has one to four carbon atoms, alkyl of one to three carbon atoms, alkylsulfonyl of one to three carbon atoms, methylphenylsulfonyl or dialkylphosphonate wherein each of said alkyl is one to three carbon atoms;

$R^2$ is $COR^6$, $CONR^7R^8$, $(C_1-C_6)$alkyl, $(C_3-C_8)$ cycloalkyl, phenyl or mono- or disubstituted phenyl wherein the substituent or substituents are each Cl, F, Br, $(C_1-C_6)$alkyl, $(C_1-C_6)$alkoxy or $CF_3$;

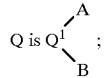

Q is $Q^1$ ;

A is H, F, Cl, Br, I, $CF_3$, $OR^9$, $S(O)_pR^{10}$, $COOR^{11}$, $CONR^9R^{11}$, CN, $NO_2$, $COR^{10}$, $CH_2OR^{11}$, $OCOR^{10}$, $NR^9R^{11}$, $N(R^9)COR^{11}$, $SO_2NR^9R^{11}$,

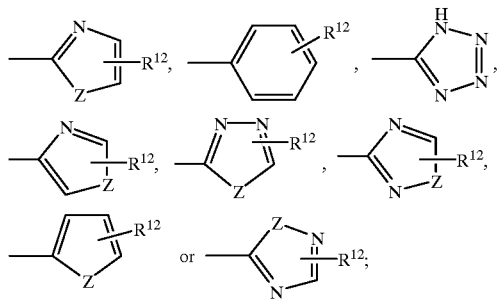

B is H, F, Cl, Br, I, $CF_3$, $OR^{13}$, $S(O)_qR^{14}$, $COOR^{15}$, $CONR^{13}R^{15}$, CN, $NO_2$, $COR^{14}$, $CH_2OR^{15}$, $OCOR^{14}$, $NR^{13}R^{15}$, $N(R^{13})COR^{15}$ or $SO_2NR^{13}R^{15}$; provided that A and B cannot both be H, or A and B are taken together, bonded to the same ring carbon of $Q^1$ and equal oxo, or when A is not H, B is as defined above or $(C_1-C_4)$alkyl;

$Q^1$ is

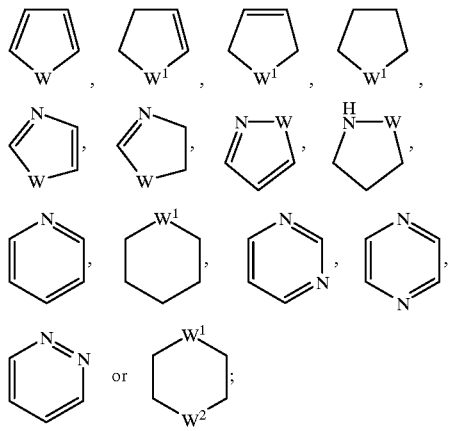

m, n, p, q and t are each zero, one or two;
W and Z are each O, S or $NR^{11}$;
$W^1$ and $W^2$ are each O, S or $NR^{10}$ provided that when one of $W^1$ and $W^2$ is O, S or $NR^{10}$, the other is O or S;
$R^3$, $R^6$, $R^{10}$, $R^{14}$ and $R^{17}$ are each $(C_1-C_6)$alkyl or phenyl; $R^5$, $R^8$, $R^{11}$, $R^{15}$ and $R^{19}$ are each H, $(C_1-C_6)$alkyl or phenyl; $R^4$, $R^7$, $R^9$, $R^{13}$ and $R^{18}$ are each H or $(C_1-C_6)$alkyl; and $R^{12}$ is H, F, Cl, Br, $CF_3$ or $(C_1-C_6)$ alkyl; provided that when $Q^1$ is

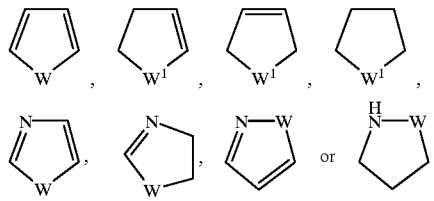

then A is not H, F, Cl, Br, I, $CF_3$, $OR^9$, $S(O)_pR^{10}$, $COOR^{11}$, $CONR^9R^{11}$, CN, $NO_2$, $COR^{10}$, $CH_2OR^{11}$, $OCOR^{10}$, $NR^9R^{11}$, $N(R^9)COR^{11}$, $SO_2NR^9R^{11}$ or

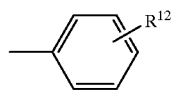

and A and B are not taken together to equal oxo.

2. A compound according to claim 1 wherein $R^1$ is H.
3. A compound according to claim 1 wherein X and Y are each H, F, Cl, $NO_2$, $(C_1-C_3)$alkyl or $CF_3$.
4. A compound according to claim 3 wherein $R^1$ is H.
5. A compound according to claim 4 wherein $R^2$ is $COR^6$, $CONR^7R^8$ or $(C_1-C_6)$alkyl.
6. A compound according to claim 3 wherein $R^2$ is $COR^6$, $CONR^7R^8$ or $(C_1-C_6)$alkyl.
7. A compound according to claim 5 wherein $R^1$ is H.
8. A compound according to claim 6 wherein $R^1$ is H.
9. A compound according to claim 1 wherein $Q^1$ is

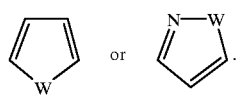

10. A compound according to claim 9 wherein $R^1$ is H.
11. A compound according to claim 9 wherein X and Y are each H, F, Cl, $NO_2$, $(C_1-C_3)$alkyl or $CF_3$.
12. A compound according to claim 11 wherein $R^1$ is H.
13. A compound according to claim 9 wherein $R^2$ is $COR^6$, $CONR^7R^8$ or $(C_1-C_6)$alkyl.
14. A compound according to claim 11 wherein $R^2$ is $COR^6$, $CONR^7R^8$ or $(C_1-C_6)$alkyl.
15. A compound according to claim 13 wherein $R^1$ is H.
16. A compound according to claim 14 wherein $R^1$ is H.
17. A compound according to claim 1 wherein $Q^1$ is

and W is O or S.

18. A compound according to claim 17 wherein $R^1$ is H.
19. A compound according to claim 17 wherein X and Y are each H, F, Cl, $NO_2$, $(C_1-C_3)$alkyl or $CF_3$.
20. A compound according to claim 19 wherein $R^1$ is H.
21. A compound according to claim 17 wherein $R^2$ is $COR^6$, $CONR^7R^8$ or $(C_1-C_6)$alkyl.
22. A compound according to claim 19 wherein $R^2$ is $COR^6$, $CONR^7R^8$ or $(C_1-C_6)$alkyl.
23. A compound according to claim 21 wherein $R^1$ is H.

24. A compound according to claim 22 wherein $R^1$ is H.

25. A compound according to claim 17 wherein W is S; $R^2$ is $CONR^7R^8$; and $R^7$ and $R^8$ are H.

26. A compound according to claim 25 wherein n is zero.

27. A compound according to claim 25 wherein $R^1$ is H.

28. A compound according to claim 27 wherein n is zero.

29. A compound according to claim 26 wherein X is Cl; and Y is H.

30. A compound according to claim 29 wherein A is Cl, Br, F, $CF_3$, $SCH_3$, $OCH_3$, $COCH_3$ or $CH_2OCH_3$; and B is H.

31. A compound according to claim 30 wherein $R^1$ is H.

32. A compound according to claim 29 wherein A and B are Br.

33. A compound according to claim 32 wherein $R^1$ is H.

34. A compound according to claim 26 wherein X is Cl; and Y is F.

35. A compound according to claim 34 wherein A is Cl; and B is H.

36. A compound according to claim 35 wherein $R^1$ is H.

37. A compound according to claim 34 wherein A is Cl; and B is $CH_3$.

38. A compound according to claim 37 wherein $R^1$ is H.

39. A compound according to claim 26 wherein X is $CF_3$; and Y is H.

40. A compound according to claim 39 wherein A is Cl; and B is H.

41. A compound according to claim 40 wherein $R^1$ is H.

42. A compound according to claim 1 wherein $Q^1$ is

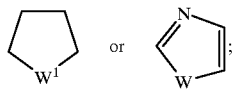

W is O or S; and $W^1$ is O or S.

43. A compound according to claim 42 wherein $R^1$ is H.

44. A compound according to claim 42 wherein X and Y are each H, F, Cl, $NO_2$, $(C_1-C_3)$alkyl or $CF_3$.

45. A compound according to claim 44 wherein $R^1$ is H.

46. A compound according to claim 42 wherein $R^2$ is $COR^6$, $CONR^7R^8$ or $(C_1-C_6)$alkyl.

47. A compound according to claim 44 wherein $R^2$ is $COR^6$, $CONR^7R^8$ or $(C_1-C_6)$alkyl.

48. A compound according to claim 45 wherein $R^1$ is H.

49. A compound according to claim 47 wherein $R^1$ is H.

50. A compound according to claim 6 wherein n is zero or one.

51. A compound according to claim 8 wherein n is zero or one.

52. A compound according to claim 14 wherein n is zero or one.

53. A compound according to claim 16 wherein n is zero or one.

54. A compound according to claim 24 wherein n is zero or one.

55. A compound according to claim 47 wherein n is zero or one.

56. A compound according to claim 49 wherein n is zero or one.

57. A compound according to claim 1 wherein A is H, F, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, or A and B are taken together, bonded to the same ring carbon of $Q^1$ and equal oxo or when A is not H, B is as defined above or $(C_1-C_3)$alkyl.

58. A compound according to claim wherein 50 is H, F, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, or A and B are taken together, bonded to the same ring carbon of $Q^1$ and equal oxo or when A is not H, B is as defined above or $(C_1-C_3)$alkyl.

59. A compound according to claim 51 wherein A is H, F, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, or A and B are taken together, bonded to the same ring carbon of $Q^1$ and equal oxo or when A is not H, B is as defined above or $(C_1-C_3)$alkyl.

60. A compound according to claim 52 wherein A is H, F, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, or A and B are taken together, bonded to the same ring carbon of $Q^1$ and equal oxo or when A is not H, B is as defined above or $(C_1-C_3)$alkyl.

61. A compound according to claim 53 wherein A is H, F, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, or A and B are taken together, bonded to the same ring carbon of $Q^1$ and equal oxo or when A is not H, B is as defined above or $(C_1-C_3)$alkyl.

62. A compound according to claim 54 wherein A is H, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, or A and B are taken together, bonded to the same ring carbon of $Q^1$ and equal oxo or when A is not H, B is as defined above or $(C_1-C_3)$alkyl.

63. A compound according to claim 55 wherein A is H, F, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, or A and B are taken together, bonded to the same ring carbon of $Q^1$ and equal oxo or when A is not H, B is as defined above or $(C_1-C_3)$ alkyl.

64. A compound according to claim 56 wherein A is H, F, Cl, Br, $CF_3$, $OR^9$, CN, $NO_2$, $COR^{10}$, $CH_2OR^{11}$ or $N(R^9)COR^{11}$ and B is H, F, Cl, Br, $CF_3$, $OR^{13}$, CN, $NO_2$, $COR^{14}$, $CH_2OR^{15}$ or $N(R^{13})COR^{15}$, or A and B are taken together, bonded to the same ring carbon of $Q^1$ and equal oxo or when A is not H, B is as defined above or $(C_1-C_3)$alkyl.

65. A compound according to claim 5 wherein $R^6$ is $CH_3$; $R^7$ is H; and $R^8$ is H or $(C_1-C_4)$alkyl.

66. A compound according to claim 6 wherein $R^6$ is $CH_3$; $R^7$ is H; and $R^8$ is H or $(C_1-C_4)$alkyl.

67. A compound according to claim 58 wherein $R^6$ is $CH_3$; $R^7$ is H; and $R^8$ is H or $(C_1-C_4)$alkyl.

68. A compound according to claim 59 wherein $R^6$ is $CH_3$; $R^7$ is H; and $R^8$ is H or $(C_1-C_4)$alkyl.

69. A compound according to claim 60 wherein $R^6$ is $CH_3$; $R^7$ is H; and $R^8$ is H or $(C_1-C_4)$alkyl.

70. A compound according to claim 61 wherein $R^6$ is $CH_3$; $R^7$ is H; and $R^8$ is H or $(C_1-C_4)$alkyl.

71. A compound according to claim 62 wherein $R^6$ is $CH_3$; $R^7$ is H; and $R^8$ is H or $(C_1-C_4)$alkyl.

72. A compound according to claim 63 wherein $R^6$ is $CH_3$; $R^7$ is H; and $R^8$ is H or $(C_1-C_4)$alkyl.

73. A compound according to claim 64 wherein $R^6$ is $CH_3$; $R^7$ is H; and $R^8$ is H or $(C_1-C_4)$alkyl.

74. A method of treating an inflammatory disease in a mammal which comprises administering to said mammal an inflammatory disease treating amount of a compound according to claim 1.

75. The method according to claim 74 wherein the inflammatory disease is rheumatoid arthritis.

76. The method according to claim 74 Wherein the inflammatory disease is osteoarthritis.

77. The method according to claim 74 wherein the inflammatory disease is psoriasis.

78. A pharmaceutical composition useful as an analgesic agent in a mammal which comprises a pharmaceutically-acceptable carrier and an analgesic response eliciting amount of a compound according to claim 1.

79. A pharmaceutical composition useful as an antiinflammatory agent in a mammal which comprises a pharmaceutically-acceptable carrier and an analgesic response eliciting amount of a compound according to claim 1.

80. A method of inhibiting prostaglandin $H_2$ synthase in a mammal in need thereof which comprises administering to said mammal a prostaglandin $H_2$ synthase inhibiting amount of a compound according to claim 1.

81. A method of inhibiting interleukin-1 biosynthesis in a mammal in need thereof which comprises administering to said mammal an interleukin-1 biosynthesis inhibiting amount of a compound according to claim 1.

82. A method of treating interleukin-1 mediated bone-metabolism disorders in a mammal which comprises administering to said mammal an interleukin-1- mediated bone metabolism disorder treating amount of a compound according to claim 1.

83. The method according to claim 82 wherein the bone metabolism disorder is osteoporosis.

84. A method of treating interleukin-1 mediated connective tissue metabolism disorder in a mammal which comprises administering to said mammal an interleukin-1 mediated connective tissue metabolism disorder treating amount of a compound according to claim 1.

85. The method according to claim 84 wherein the connective tissue metabolism disorder is periodontal disease or tissue scarring.

86. A method of treating interleukin-1 mediated immune dysfunction in a mammal which comprises administering to said mammal an interleukin-1 mediated immune dysfunction treating amount of a compound according to claim 1.

87. The method according to claim 86 wherein the immune dysfunction is allergy or psoriasis.

88. A pharmaceutical composition useful as an inhibitor of prostaglandin $H_2$ synthase in a mammal which comprises a pharmaceutically acceptable carrier and a prostaglandin $H_2$ synthase inhibiting amount of a compound according to claim 1.

89. A pharmaceutical composition useful as an inhibitor of interleukin-1 biosynthesis in a mammal which comprises a pharmaceutically acceptable carrier and an interleukin-1 biosynthesis inhibiting amount of a compound according to claim 1.

90. A pharmaceutical composition useful in treating interleukin-1 mediated bone metabolism disorder in a mammal which comprises a pharmaceutically-acceptable carrier and an interleukin-1 mediated bone metabolism disorder treating amount of a compound according to claim 1.

91. A pharmaceutical composition useful in creating interleukin-1 mediated connective tissue metabolism disorders in a mammal which comprises a pharmaceutically-acceptable carrier and an interleukin-1 mediated connective tissue metabolism disorder treating amount of a compound according to claim 1.

92. A pharmaceutical composition useful in treating interleukin-1 mediated immune dysfunction in a mammal which comprises a pharmaceutically-acceptable carrier and an interleukin-1 mediated immune dysfunction treating amount of a compound according to claim 1.

93. A method of eliciting an analgesic response in a mammal which comprises administering to said mammal an analgesic response eliciting amount of a compound of the formula

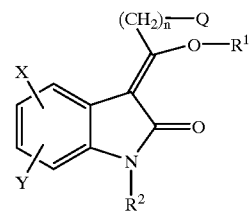

or a pharmaceutically-acceptable salt thereof, wherein

X is H, F, Cl, Br, $(C_1-C_6)$alkyl, $(C_3-C_8)$cycloalkyl, $NO_2$, $CF_3$, CN, SH, $S(O)_mR^3$, $OR^4$, $COR^4$ or $CONR^4R^5$;

Y is H, F, Cl, Br, $(C_1-C_6)$alkyl, $(C_3-C_8)$cycloalkyl, $NO_2$, $CF_3$, CN, SH, $S(O)_qR^{17}$, $OR^{18}$, $COR^{18}$ or $CONR^{18}R^{19}$;

$R^1$ is H, alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omega-alkoxycarbonylalkanoyl, said alkoxy having one to three carbon atoms and said alkanoyl having three to five carbon atoms, alkoxy carbonyl of two to ten carbon atoms, phenoxycarbonyl, 1-(acyloxy)alkyl wherein acyl has one to four carbon atoms and said alkyl has two to four carbon atoms, 1-(alkoxycarbonyloxy)alkyl wherein said alkoxy has two to five carbon atoms and said alkyl has one to four carbon atoms, alkyl of one to three carbon atoms, alkylsulfonyl of one to three carbon atoms, methylphenylsulfonyl or dialkylphosphonate wherein each of said alkyl is one to three carbon atoms;

$R^2$ is $COR^6$, $CONR^7R^8$, $(C_1-C_6)$alkyl, $(C_3-C_8)$cycloalkyl, phenyl or mono- or disubstituted phenyl wherein the substituent or substituents are each Cl, F, Br, $(C_1-C_6)$alkyl, $(C_1-C_6)$alkoxy or $CF_3$;

Q is 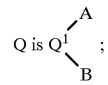

A is H, F, Cl, Br, I, $CF_3$, $OR^9$, $S(O)_pR^{10}$, $COOR^{11}$, $CONR^9R^{11}$, CN, $NO_2$, $COR^{10}$, $CH_2OR^{11}$, $OCOR^{10}$, $NR^9R^{11}$, $N(R^9)COR^{11}$, $SO_2NR^9R^{11}$,

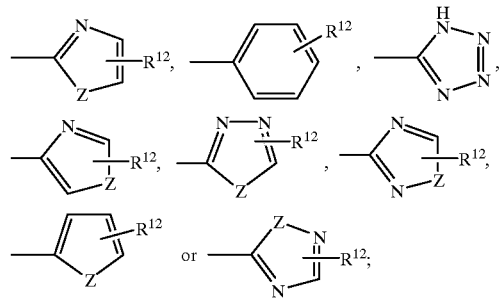

B is H, F, Cl, Br, I, $CF_3$, $OR^{13}$, $S(O)_rR^{14}$, $COOR^{15}$, $CONR^{13}R^{15}$, CN, $NO_2$, $COR^{14}$, $CH_2OR^{15}$, $OCOR^{14}$, $NR^{13}R^{15}$, $N(R^{13})COR^{15}$ or $SO_2NR^{13}R^{15}$;

provided that A and B cannot both be H, or A and B are taken together, bonded to the same ring carbon of $Q^1$ and equal oxo, or when A is not H, B is as defined above or $(C_1-C_4)$alkyl;

$Q^1$ is

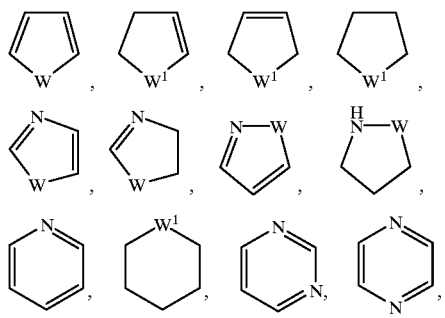

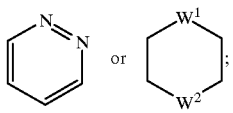

m, n, p, q and t are each zero, one or two;
W and Z are each O, S or $NR^{11}$;
$W^1$ and $W^2$ are each O, S or $NR^{10}$ provided that when one of $W^1$ and $W^2$ is O, S or $NR^{10}$, the other is O or S;
$R^3$, $R^6$, $R^{10}$, $R^{14}$ and $R^{17}$ are each $(C_1-C_6)$alkyl or phenyl; $R^5$, $R^8$, $R^{11}$, $R^{15}$ and $R^{19}$ are each H, $(C_1-C_6)$alkyl or phenyl; $R^4$, $R^7$, $R^9$, $R^{13}$ and $R^{18}$ are each H or $(C_1-C_6)$alkyl; and $R^{12}$ is H, F, Cl, Br, $CF_3$ or $(C_1-C_6)$alkyl.

* * * * *